United States Patent [19]

He et al.

[11] Patent Number: 6,071,700
[45] Date of Patent: Jun. 6, 2000

[54] HETEROLOGOUS POLYPEPTIDE PRODUCTION IN THE ABSENCE OF NONSENSE-MEDIATED MRNA DECAY FUNCTIONS

[75] Inventors: Feng He, Worcester; Allan S. Jacobson, Grafton, both of Mass.

[73] Assignee: University of Massachusetts, Boston, Mass.

[21] Appl. No.: 09/177,431

[22] Filed: Oct. 21, 1998

Related U.S. Application Data

[63] Continuation-in-part of application No. 08/955,472, Oct. 21, 1997, abandoned, which is a continuation-in-part of application No. 08/375,300, Jan. 20, 1995, Pat. No. 5,679,566.

[51] Int. Cl.$^7$ .............................. C12Q 1/68; C12N 1/15; C12N 15/12; C12N 15/31
[52] U.S. Cl. .......................... 435/6; 435/254.2; 536/23.5; 536/23.7
[58] Field of Search ................... 435/6, 254.2; 536/23.5, 536/23.6, 23.7

[56] References Cited

U.S. PATENT DOCUMENTS 5,679,566  10/1997  He et al. ............................... 435/240.2

FOREIGN PATENT DOCUMENTS

WO 97/12617  4/1997  WIPO .

OTHER PUBLICATIONS

Darling et al., "Premature Termination Codons are Present on both Alleles of the Bullous Pemphigoid . . . " J. Invest. Dermatol. 108(4):463–468, 1997.
Altamura et al., "NAM7 nuclear gene encodes a novel member of a family of helicases with Zn–Ligand motif and is involved in mitochondrial functions in *Saccharomyces cerevisae*" J. Mol. Biol. 224:575–587, 1992.
Barker et al., "Nonsense Codons within the Rouse Sarcoma Virus gag Gene Decrease the Stability of Unspliced viral RNA" Mol. and Cell. Biol., vol. II, No. 5, pp. 2760–2768, 1991.
Cui et al., "Identification and characterization of gene that are required for the accelerated degredation of mRNAs containing a premature transnational termination codon" Genes & Dev. 9:423–436, 1995.
Daar et al., "Premature Translation Termination Mediates Triosephosphate Isomerase mRNA Degredation" Mol. and Cell. Biol. 8(2):802–811, 1988.
Fields et al., "A novel genetic system to detect protein–protein interaction" Nature 340:245–246, 1989.
Gozalbo et al., "Nonsense suppressors partially revert the decrease of the nRNA Level of a nonsense mutant allele in yeast" Current Genetics 17(1):77–79, 1990.
He et al., "Upf1p, Nmd2p, and UPf3p are interacting components of the yeast nonsense–mediated mRNA decay pathway" Mol. and Cell. Biol. 17(3):1580–1594, 1997.
He et al., "Identification of a novel component of the nonsense–mediated mRNA decay pathway by use of an interacting protein screen" Genes &Devel. 9:437–454, 1995.

He et al.,"stabilization and ribosome association of unspliced pre–mRNA's in a yeast upf1 mutant" Proc. Nat'l. Acad. Sci. USA 90:7034–7038, 1993.
Johnston et al., "Complete nucleotide sequence of *saccharomyces cervisae* chromosome VIII" Science 265:2077–1082, 1994.
Johnston et al., "The complete sequence or *Saccharomyces cerevisae* chromosome VIII" Genbank, Accession No. U10556, 1994.
Lee et al. "A genetic screen identifies cellular factors involved in retroviral—1 frameshifting" Proc. Nat'l Acad. Sci. USA 92:6587–6591, 1995.
Lee et al., "Identification of an additional gene required for eukaryotic nonsense mRNA turnover" Proc. Nat'l. Acad. Sci. USA 92:10354–10538, 1995.
Leeds et al., "Gene products that promote mRNA turnover in *Saccharomyces cerevisae*" Mol. and Cell. Biol. 12(5):2165–2177, 1992.
Losson et al., "Interference of nonsense mutations with eukaryotic messenger RNA stability" Proc. Nat'l. Acad. Sci. USA 76:5134–5137, 1979.
Ma et al., "Converting a eukaryotic transcriptional inhibitor into an activator" Cell 55:443–446, 1988.
Maquat, "When cells stop making sense: Effects of nonsense codons on RNA metabolism in vertebrate cells" RNA 1:453–465, 1995.
Peltz et al., "Nonsense–mediated mRNA decay in yeast" Prog. Nucl. Acids Res. and Mol. Biol. 47:271–97, 1994.
Peltz et al., "mRNA destabilization triggered by premature transnational termination depends on at least three cis–acting sequence elements . . . " Genes & Dev., Cold Spring Harbor Lab. Press. 7:1737–1754, 1993.
Sambrook et al., "Molecular Cloning: A laboratory Mannual" Cold Spring Harbor Laboratory Press, p.3.18, 1989.

(List continued on next page.)

*Primary Examiner*—John S. Brusca
*Attorney, Agent, or Firm*—Fish & Richardson, P.C.

[57] ABSTRACT

The invention relates to the discovery of a gene, NMD2, named after its role in the Nonsense-Mediated mRNA Decay pathway, and the protein, Nmd2p, encoded by the NMD2 gene. The amino acid sequence of Nmd2p and the nucleotide sequence of the NMD2 gene encoding it are disclosed. Nmd2p is shown herein to bind to another protein in the decay pathway, Upf1p. A C-terminal fragment of the protein is also shown to bind Upf1p and, when overexpressed in the host cell, the fragment inhibits the function of Upf1p, thereby inhibiting the nonsense-mediated mRNA decay pathway. The invention also relates to methods of inhibiting the nonsense-mediated mRNA decay pathway to stabilize mRNA transcripts containing a nonsense codon which normally would cause an increase in the transcript decay rate. Such stabilization of a transcript is useful for the production of a recombinant protein or fragment thereof. The invention also relates to methods of identifying molecules that inhibit the nonsense-mediated mRNA decay pathway, and the use of such molecules for treatment of disorders associated with nonsense mutations.

14 Claims, 11 Drawing Sheets

OTHER PUBLICATIONS

Weng et al., "Identification and characterization of mutations in the UPF1 gene that affect nonsense suppression and the formation of . . . " Mol. and Cell. Biol. 16(10):5491–5506, 1996.

Zhang et al., "Polysome–associated mRNAs are substrates for the non–sense–mediated mRNA decay pathway in *Saccharomyces cerevisiae*" 3:234–244, 1997.

Pulak et al., "mRNA surveillance by the Caenorhabditis elegans smg genes" *Genes & Development*, 7:1885–1897, (1193).

Applequist "Clining & Characterization of HUPFI . . . ", Nucl. Acid Res. 25 814–821 (1997).

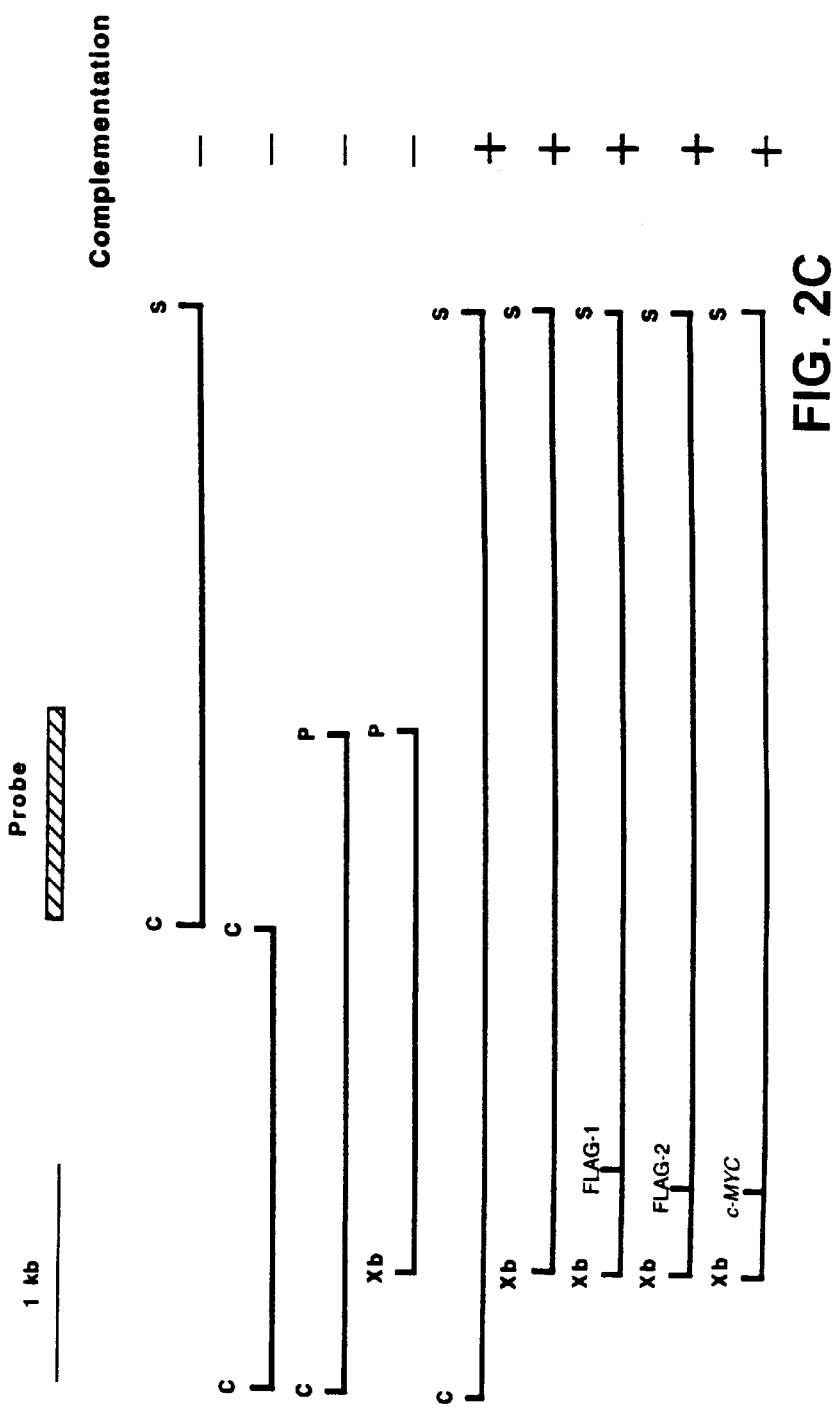

```
gaattcatga acgggaaata agaaaaacaa aaagaaaata tacatagtta gttactatcc
actcaataat attaaacgag tgaatgcttt tacttttaac tttagtttaa tcttaattta
cattatttta gtatcatcag tttccctttg cttacttgat ttgggaggga cacctttata
cgctttcgta ctaactgatc aaatgaaaag cttaccagaa acttacgatg ctattgtgaa
ggagaaaaaa aaagcgaaaa gaggcatcgt tttaacgcac actaacagaa gactctattt
ctcttgtcag ccaacaaacg ttgaagattt catcaggaaa gaaggaaggg cagcaagacc
gaatatactt tttatattac atcaatcatt gtcattatca aatggtcggt tccggttctc
acactcctta tgatatatca aactctccat ctgatgtaaa tgtccaaccc gcaacacaac
taaattccac cttggtggag gatgacgatg tagataatca gctatttgaa gaggctcaag
tcactgagac tggattccgt tcgccttcag cttcagacaa ttcatgtgcg tattgtggta
tagattctgc aaagtgtgtc atcaaatgta attcatgtaa gaaatggttt tgtaacacta
aaaacggtac aagcagctcc cacattgtta atcacttagt tttatcccac cataacgtag
tttctttaca tccagattct gacttagggg ataccgtttt ggaatgttat aactgtggac
gtaagaacgt gtttttattg ggatttgttt ccgctaaaag tgaggccgtg gttgttttac
tttgtagaat accttgtgcc cagacgaaaa atgcgaactg ggatactgat caatggcaac
cattaattga agacagacaa cttttatcat gggtcgcaga gcaaccaact gaagaagaaa
aattgaaagc tcgtttaatc actcctagcc aaatttccaa gttggaggca aaatggagat
ccaataaaga cgctacaatt aatgatattg acgcccaga ggaacaggaa gcaatcccac
ctttactatt gagatatcaa gacgcctacg aataccaaag atcttacggg cctttaatca
aattggaggc cgactatgat aaacaactca aggaatctca agctttagaa catatttctg
tttcatggtc cttagcttta aataataggc atttagcatc tttcacttta tctactttcg
aatctaacga gttgaaagtt gccatcggtg atgaaatgat actatggtac tctggcatgc
aacatcctga ttgggaaggt cgtggttaca ttgttcggtt accaaatagc ttccaggaca
cattcacatt agagttaaaa ccaagtaaaa cgccacctcc aacacatttg accactggtt
ttactgctga gttcatctgg aaaggtacct cttatgacag gatgcaagac gcattgaaaa
aatttgccat tgataaaaaa tctatttcag gttatttgta ctataaaatt ttaggccatc
aagtggttga catttcattt gatgtcccat tacctaagga gttttcaatt ccgaattttg
cacaattaaa ctcatcccag tcgaacgctg ttagtcatgt attacaacgt ccgttatctt
taattcaagg cccaccaggc actggtaaaa cagttacttc agcaacgatt gtgtatcacc
tttccaaaat acacaaggat agaatattgg tgtgtgcccc atcaaacgtt gctgtagatc
atttggctgc caaattacgt gacttgggtt taaaagttgt tagacttacc gcgaaaagta
gagaagatgt ggagagttcc gtctccaact tagcattgca taatttggtt ggccgtggtg
ctaaagggga attaaaaaac ctattaaagt taaaggatga agttggcgaa ttatctgctt
ctgatacaaa acggtttgtt aaattagtaa ggaaaacaga agcagaaatt ctcaataagg
cagatgtcgt atgttgcaca tgtgttggtg ctggtgataa gcgcttagac actaaattta
ggactgtgtt aattgatgaa agtactcaag cttctgagcc ggaatgttta atcccaatcg
ttaaaggtgc gaaacaagtt atacttgttg gtgatcacca gcaactgggc ccagtcatat
tggaacgaaa ggcggcagac gctggtttga aacaatctct ctttgaaaga ttaatctctc
taggccacgt accgattcgt ttggaagttc aataccgtat gaatccttat ttgagtgagt
ttccaagtaa catgttttat gaaggcagcc tacaaaatgg tgtaacgatt gaacagcgta
ccgttcccaa cagcaaattc ccatggccaa ttcgcggtat accaatgatg ttttgggcca
attacggtag agaggagatt tctgctaacg gtacttcctt cttaaacaga attgaagcca
tgaattgtga acgaatcatc actaaacttt tcagagacgg tgtcaagccc gagcaaattg
gtgttatcac accatatgag ggacaaagag cttatatttt acaatatatg caaatgaatg
gttcattgga taaggatttg tatatcaaag tggaagttgc ctcagttgat gcattccaag
gtcgtgaaaa ggattacata atcttatcgt gtgttcgtgc caatgaacaa caggccattg
gtttcttacg tgatcctcgt cgtctaaacg tgggtctaac ccgtgccaaa tatggtctag
ttattcttgg taatcctaga tctttggcaa gaaacacatt atggaaccat ctgttaatcc
acttcagaga gaagggttgt ttagtcgaag gtacgttgga taacttacag ttatgcactg
ttcaattagt tcgtcctcag ccaagaaaga ctgaacgcc aatgaacgct caatttaacg
tagaatctga aatgggtgac tttccgaagt tccaggattt tgatgcacag agtatggtgt
cattcagtgg tcaaattggg gactttggta atgcatttgt tgacaacaca gaactttctt
```

FIG. 5A

```
cttacatcaa taatgaatat tggaattttg agaattttaa aagtgctttt tctcaaaagc
aaaatcgcaa tgaaattgac gatagaaatt tgtaccagga ggaggcttct catttgaact
ctaacttcgc gagagagtta cagagagaag aacaaaagca tgaattgtca aaagacttca
gcaatttggg aatataattc ggtgaaccct gttaaaataa aatgttaaac ttggcttgtg
atacaaaacg gctcaaccgt gaaatgagcg ctgcaaaatt attcgagata gactcgcaat
ttgcacaatt gtaacctgaa aaattttttt acttttccgg aggtgcatct atcattacag
tatgtgataa aggggcatgg acttgatatc ctagcctact aatctctttg ctaaaacatg
ttgcaa    (SEQ ID NO:7)
```

FIG. 5B

MVGSGSHTPYDISNSPSDVNVQPATQLNSTLVEDDDVDNQLFEE
AQVTETGFRSPSASDNSCAYCGIDSAKCVIKCNSCKKWFCNTKNGTSSSHIVNHLVLS
HHNVVSLHPDSDLGDTVLECYNCGRKNVFLLGFVSAKSEAVVVLLCRIPCAQTKNANW
DTDQWQPLIEDRQLLSWVAEQPTEEEKLKARLITPSQISKLEAKWRSNKDATINDIDA
PEEQEAIPPLLLRYQDAYEYQRSYGPLIKLEADYDKQLKESQALEHISVSWSLALNNR
HLASFTLSTFESNELKVAIGDEMILWYSGMQHPDWEGRGYIVRLPNSFQDTFTLELKP
SKTPPPTHLTTGFTAEFIWKGTSYDRMQDALKKFAIDKKSISGYLYYKILGHQVVDIS
FDVPLPKEFSIPNFAQLNSSQSNAVSHVLQRPLSLIQGPPGTGKTVTSATIVYHLSKI
HKDRILVCAPSNVAVDHLAAKLRDLGLKVVRLTAKSREDVESSVSNLALHNLVGRGAK
GELKNLLKLKDEVGELSASDTKRFVKLVRKTEAEILNKADVVCCTCVGAGDKRLDTKF
RTVLIDESTQASEPECLIPIVKGAKQVILVGDHQQLGPVILERKAADAGLKQSLFERL
ISLGHVPIRLEVQYRMNPYLSEFPSNMFYEGSLQNGVTIEQRTVPNSKFPWPIRGIPM
MFWANYGREEISANGTSFLNRIEAMNCERIITKLFRDGVKPEQIGVITPYEGQRAYIL
QYMQMNGSLDKDLYIKVEVASVDAFQGREKDYIILSCVRANEQQAIGFLRDPRRLNVG
LTRAKYGLVILGNPRSLARNTLWNHLLIHFREKGCLVEGTLDNLQLCTVQLVRPQPRK
TERPMNAQFNVESEMGDFPKFQDFDAQSMVSFSGQIGDFGNAFVDNTELSSYINNEYW
NFENFKSAFSQKQNRNEIDDRNLYQEEASHLNSNFARELQREEQKHELSKDFSNLGI
(SEQ ID NO:8)

FIG. 6

```
gaattctact tgataggatt ttattgccgt ctttttctat aagttctata tcctcagtat
cgtcttcttc ctcgtcttcc tcctcatgac tagtagagtg agaagatgaa tgatcagaat
tattgatgat ttcgttatct tctaaagtca ccaaatcccc atgtaaatca tccaatgcag
tgttcatatt aatgattgag tagattggta catatgctat ttcggaagac ttttgttatt
ctatggttta tcatcccttt atttattttg tgtattgttt gctgatcaaa agttgaaaat
ttttcgccta aaaagtaaga tacaaaagaa aatattgtcg atgattattg catgaatata
tcagcaaaga ggaaaggaaa acctactgag ggacttacat ttctgctgaa atatatagta
atctatcatg agcaatgtgg ctggggaatt gaagaatagt gaggggaaaa agaaaggcag
gggaaatagg tatcataaca agaacagagg aaaaagtaag aatgagacgg tagatcctaa
aaagaatgag aataaggtta ataatgctac taatgctacc cacaacaata gcaaaggcag
aaggaataac aagaaaagga acagagagta ttataactat aaaagaaagg ctagattggg
taaatcaacc gagaatgaag gatttaagct tgttattaga ttgctacctc caaatttgac
tgcagatgaa tttttgcca tcttacgaga taataataac gatgatggtg ataagcaaga
tatccagggt aaactcaagt acagtgactg gtgttttttt gaaggtcatt attctagtaa
agtattcaaa aactcgacat attctcggtg caatttcttg ttcgacaact tatcagactt
ggaaaaatgc gcaaatttca ttaaaacttg taaattcatt gataataagg ataatattac
aattccagat atgaaactgt cgccctacgt aaagaaattc actcaaacat caaaaaagga
tgccgcgcta gtaggaacaa ttgaagaaga cgaaattttt aaaacattta tgaattcaat
gaaacagctg aatgaaaatg acgagtactc attccaagat tttagcgtat tgaaatcttt
agaaaaagaa ttctcaaaaa gcatagagtt agaaaataaa atagcagaaa gaacagaaag
ggtgttaaca gagctggttg gaactggtga taaggtcaag aataagaaca aaaagaagaa
aaataaaaac gccaaaaaga aattcaaaga agaggaagca tccgctaaga taccaaagaa
aaaacggaac agaggcaaga agaagcgtga aaatcgtgaa aaaagcacca tttctaagac
caagaacagt aatgtggtta ttattgagga agcgggtaaa gaggttttga aacaaaggaa
gaagaaaatg cttttgcaag agaagttaaa aatatcaaac tcctctcagc ctcagtcatc
atccgctcaa acccagccgt cgttccaacc taaagaaaac cttttcgtac cacgggtaaa
aattttgcat cgtgatgata ccaagaagta gtaaaagctc atggcttctt atatattata
tatggaatac atttataata aataataag aattatatat tttatgatta tattattaca
taaagtattc cccattataa attctgagtt tcgtatttaa tgattttca atgaatattt
aaaataataa aatatatgaa atgttcatat acaatgaaat tgtcatgaag aaagatgact
ccaagtatcg tttataaatc gtcgagaaaa agattatgaa gttggttaac ttttaaaaa
acgtgcgcaa tgagcaggtt accatagaac taaaaacgg taccaccgtt tggggtacac
tgcagtcggt atcaccacaa atgaatgcta tcttaactga     (SEQ ID NO:9)
```

FIG. 7

MSNVAGELKNSEGKKKGRGNRYHNKNRGKSKNETVDPKKNENKV
NNATNATHNNSKGRRNNKKRNREYYNYKRKARLGKSTENEGFKLVIRLLPPNLTADEF
FAILRDNNNDDGDKQDIQGKLKYSDWCFFEGHYSSKVFKNSTYSRCNFLFDNLSDLEK
CANFIKTCKFIDNKDNITIPDMKLSPYVKKFTQTSKKDAALVGTIEEDEIFKTFMNSM
KQLNENDEYSFQDFSVLKSLEKEFSKSIELENKIAERTERVLTELVGTGDKVKNKNKK
KKNKNAKKKFKEEEASAKIPKKKRNRGKKKRENREKSTISKTKNSNVVIIEEAGKEVL
KQRKKKMLLQEKLKISNSSQPQSSSAQTQPSFQPKENLFVPRVKILHRDDTKK
(SEQ ID NO:10)

FIG. 8

SEQUENCE LISTING (1) GENERAL INFORMATION:

(iii) NUMBER OF SEQUENCES: 18

(2) INFORMATION FOR SEQ ID NO:1:

(i) SEQUENCE CHARACTERISTICS:
      (A) LENGTH: 4080 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
CCTGAATGAC CTTTATCTTA ATTATGCACC ATCATATAGC GTTTCTATGA TCACTACGGG      60

ATATTATGAT ATTGTTAGGG GGTTATATTG AATATTTCTT AGGGCATGAG GATGATATTA     120

GGGTTATTAA TAGGTTTACA ATTATATAAT TTATGTGATA ATTATCACTT GATACGAATT     180

GATGGAGCCT GCTTCTTTTT TTTTTTTTCA CTTTCTTGGC AGTCACTGAA AAACTGCATT     240
```

```
-continued

CGAATACAGG TTTGAGAAAC TAATGAGGCC CATATTACTT TACAATGAAC AGTAACAATC      300

AACTTAAATG CTTAAATAAT CTAATATTGT ATCTGCATTG ATAATACATT GGACAGAAAT      360

TATGGACGTA TGTTTGATTT ATCTTACTGT GGCCAGATCG GCCTTTCAGT ACTTCTAAGG      420

TTTTATACTA ACTTCTTTTA TTGATCGTTG TAAACTACGG TAACAATTAT GTATCAACAG      480

GATGGACGGA AAAAAGAATT GCATGATTTG AACACCCGAG CTTGGAATGG CGAAGAAGTC      540

TTTCCCCTGA AAAGTAAAAA ACTGGATTCC AGTATAAAGA GAAACACTGG CTTTATAAAA      600

AAACTAAAGA AGGGTTTTGT GAAAGGTTCA GAATCTTCAT TATTGAAAGA TTTAAGTGAG      660

GCGTCCTTGG AAAAGTACCT ATCAGAGATA ATAGTGACGG TAACAGAATG TCTGCTAAAT      720

GTTTTGAATA AAAATGATGA CGTAATTGCC GCTGTTGAGA TCATAAGTGG ACTTCATCAA      780

AGGTTCAATG GCCGATTTAC TAGTCCGCTT TTAGGAGCTT TTTTACAAGC TTTTGAGAAC      840

CCCTCTGTTG ACATTGAATC CGAAAGAGAT GAGCTTCAAA GGATAACCAG AGTTAAAGGT      900

AATCTTCGGG TATTTACCGA GCTTTATTTA GTTGGAGTTT TTAGAACATT GGATGATATT      960

GAGTCGAAAG ATGCTATTCC AAACTTCCTA CAGAAGAAAA CTGGGCGAAA GGATCCGTTG     1020

TTATTCAGTA TTCTCAGAGA GATTCTTAAT TATAAGTTCA AATTGGGCTT TACTACCACT     1080

ATTGCGACCG CATTTATTAA GAAATTTGCA CCTTTGTTTC GCGACGATGA TAATTCTTGG     1140

GATGATTTAA TATATGACTC GAAGTTAAAA GGTGCGTTAC AGTCTCTGTT TAAGAATTTT     1200

ATAGACGCCA CTTTTGCGAG GGCCACAGAA CTGCATAAGA AGGTCAATAA ACTGCAAAGA     1260

GAACATCAGA AATGCCAAAT AAGAACGGGA AAATTGAGAG ATGAGTACGT AGAGGAGTAC     1320

GACAAGTTAC TTCCAATATT CATTAGGTTC AAGACATCTG CAATTACTTT GGGAGAATTT     1380

TTTAAGTTAG AAATTCCGGA GCTTGAAGGT GCCTCTAATG ATGATCTGAA AGAAACAGCT     1440

TCTCCAATGA TCACGAATCA GATATTGCCA CCCAACCAAC GATTATGGGA AAATGAAGAT     1500

ACAAGGAAAT TTTATGAAAT CTTACCAGAT ATCTCAAAAA CAGTAGAAGA ATCACAATCT     1560

TCTAAAACAG AAAAAGATTC AAACGTTAAC TCAAAAAATA TCAATCTATT CTTTACGGAT     1620

TTGGAAATGG CAGATTGTAA AGATATAATC GATGACCTTT CAAATAGATA TTGGTCATCA     1680

TATTTGGACA ACAAAGCCAC AAGAAATCGA ATATTGAAAT TTTTCATGGA AACACAAGAT     1740

TGGAGCAAAC TGCCAGTGTA TTCCAGATTT ATTGCAACAA ATAGCAAATA TATGCCGGAA     1800

ATTGTTTCTG AGTTTATTAA CTACCTAGAC AATGGCTTCA GGAGTCAATT ACATTCTAAT     1860

AAGATTAACG TTAAAAACAT CATCTTCTTC AGTGAAATGA TTAAATTTCA ATTAATACCA     1920

TCGTTTATGA TTTTTCATAA GATTAGAACA TTAATCATGT ATATGCAAGT TCCAAATAAC     1980

GTAGAAATTT TGACGGTTTT GTTGGAGCAC TCAGGGAAAT TTCTGCTAAA TAAGCCAGAA     2040

TATAAGGAAT TAATGGAAAA AATGGTCCAA CTAATCAAGG ATAAAAAAAA TGATAGGCAA     2100

TTGAACATGA ACATGAAAAG CGCCTTAGAA AACATAATTA CTTTACTTTA TCCCCCTTCT     2160

GTAAAATCAT TAAATGTTAC GGTAAAAACA ATAACGCCTG AACAACAGTT TTATCGCATA     2220

TTAATTAGAA GTGAACTAAG TAGCCTAGAC TTCAAACACA TTGTCAAGTT GGTTCGGAAA     2280

GCTCACTGGG ACGATGTAGC TATTCAGAAA GTGCTGTTTT CTCTGTTTTC AAAACCACAT     2340

AAGATTAGCT ATCAAAATAT TCCCTTATTA ACAAAAGTTC TAGGCGGTCT ATACAGTTAC     2400

CGCCGCGATT TCGTCATCAG ATGTATAGAC CAAGTACTGG AAAACATTGA GCGAGGCTTA     2460

GAAATTAACG ATTATGGACA AAACATGCAT AGAATATCAA ATGTCAGATA CTTAACTGAA     2520

ATATTCAACT TTGAAATGAT AAAATCCGAT GTTTTGTTAG ATACTATCTA CCACATTATT     2580

CGGTTTGGTC ATATCAACAA TCAACCCAAT CCATTTTATT TAAACTACTC AGATCCACCG     2640
```

-continued

```
GATAATTATT TCAGGATTCA ACTAGTCACT ACAATTCTGT TAAATATCAA CAGGACCCCT    2700

GCAGCTTTTA CTAAGAAATG CAAACTTTTG CTGAGGTTTT TCGAGTATTA TACTTTTATT    2760

AAAGAACAAC CTTTACCCAA GGAAACAGAA TTCAGAGTTT CAAGCACATT TAAAAAATAT    2820

GAGAATATTT TCGGAAACAC TAAATTTGAA AGGTCAGAAA ATTTGGTAGA AAGTGCCTCA    2880

AGGTTGGAAA GTTTACTGAA ATCATTAAAC GCAATAAAAA GTAAGACGA CAGAGTGAAG     2940

GGATCTTCTG CAAGCATTCA AACGGTAAG GAGAGTGCTG TTCCTATCGA GTCAATCACC     3000

GAAGATGATG AGGATGAAGA TGATGAAAAC GACGATGGTG TCGATTTACT AGGAGAAGAT    3060

GAAGACGCGG AGATAAGTAC ACCGAACACA GAGTCAGCGC CAGGAAAACA TCAGGCAAAG    3120

CAAGACGAAA GTGAAGATGA AGACGATGAG GACGATGACG AGGATGATGA CGATGACGAT    3180

GACGATGATG ATGATGATGG AGAAGAAGGC GATGAGGATG ATGATGAAGA TGATGATGAT    3240

GAGGATGATG ATGATGAAGA AGAAGAAGAC AGCGACTCTG ATTTGGAGTA TGGTGGTGAT    3300

CTTGACGCAG ACAGAGATAT TGAAATGAAA CGAATGTATG AAGAGTACGA GAGAAAACTA    3360

AAGGATGAGG AAGAAAGGAA AGCGGAAGAA GAATTGGAAA GGCAATTTCA GAAAATGATG    3420

CAAGAATCCA TAGACGCAAG GAAAAGCGAA AAGGTTGTTG CCAGTAAAAT TCCAGTAATT    3480

TCGAAGCCAG TCAGCGTTCA AAAACCTTTA TTATTAAAAA AGAGTGAAGA ACCTTCTTCA    3540

AGCAAGGAGA CCTACGAAGA GTTATCCAAG CCAAAGAAGA TTGCATTTAC GTTCTTGACT    3600

AAAAGCGGTA AGAAGACACA ATCAAGAATT TTACAATTAC CAACGGATGT GAAATTTGTC    3660

TCTGATGTCC TTGAAGAAGA AGAGAAACTA AAAACCGAGC GAAACAAGAT TAAAAAGATT    3720

GTTTTAAAAC GTTCTTTCGA CTGAGATTCT TTGCGAATAT AGTTCTTTAA ATTTTTACTA    3780

TATATGCCCA CTTATGTTTG GCTCTATTAA ATGGCTACGT GTTTATATAG TACCGTTTAT    3840

GACGCTGTAT TTTTATTTAC ACTGCTTTCC AGGAGATTAA AGAGCGGAGT GTTAGTCAAC    3900

TCTCACGACA ACAACAGTTA TATCGTCTTC TTTACCACCG CTGTAGTTTT TGCCAGTTAG    3960

CTTAGAAATC TCTTGCGCAA AAACACTGGG GTAATTGGGG TCCTTGCTTA AACTGACAAC    4020

ATTGTCCACA AACTTCTGGG ATAATAGCTG TAACTCATCG TTTGTTCTCG CAGCGTTATC    4080
```

(2) INFORMATION FOR SEQ ID NO:2:

(i) SEQUENCE CHARACTERISTICS:
        (A) LENGTH: 1089 amino acids
        (B) TYPE: amino acid
        (D) TOPOLOGY: linear (ii) MOLECULE TYPE: protein (xi) SEQUENCE DESCRIPTION: SEQ ID NO:2:

```
Met Asp Asp Gly Arg Lys Lys Glu Leu His Asp Leu Asn Thr Arg Ala
  1               5                  10                  15

Trp Asn Gly Glu Glu Val Phe Pro Leu Lys Ser Lys Lys Leu Asp Ser
                 20                  25                  30

Ser Ile Lys Arg Asn Thr Gly Phe Ile Lys Leu Lys Lys Gly Phe
             35                  40                  45

Val Lys Gly Ser Glu Ser Ser Leu Leu Lys Asp Leu Ser Glu Ala Ser
         50                  55                  60

Leu Glu Lys Tyr Leu Ser Glu Ile Ile Val Thr Val Thr Glu Cys Leu
 65                  70                  75                  80

Leu Asn Val Leu Asn Lys Asn Asp Asp Val Ile Ala Ala Val Glu Ile
                 85                  90                  95
```

-continued

```
Ile Ser Gly Leu His Gln Arg Phe Asn Gly Arg Phe Thr Ser Pro Leu
            100                 105                 110

Leu Gly Ala Phe Leu Gln Ala Phe Glu Asn Pro Ser Val Asp Ile Glu
            115                 120                 125

Ser Glu Arg Asp Glu Leu Gln Arg Ile Thr Arg Val Lys Gly Asn Leu
            130                 135                 140

Arg Val Phe Thr Glu Leu Tyr Leu Val Gly Val Phe Arg Thr Leu Asp
145                 150                 155                 160

Asp Ile Glu Ser Lys Asp Ala Ile Pro Asn Phe Leu Gln Lys Lys Thr
                165                 170                 175

Gly Arg Lys Asp Pro Leu Leu Phe Ser Ile Leu Arg Glu Ile Leu Asn
            180                 185                 190

Tyr Lys Phe Lys Leu Gly Phe Thr Thr Ile Ala Thr Ala Phe Ile
            195                 200                 205

Lys Lys Phe Ala Pro Leu Phe Arg Asp Asp Asn Ser Trp Asp Asp
            210                 215                 220

Leu Ile Tyr Asp Ser Lys Leu Lys Gly Ala Leu Gln Ser Leu Phe Lys
225                 230                 235                 240

Asn Phe Ile Asp Ala Thr Phe Ala Arg Ala Thr Glu Leu His Lys Lys
                245                 250                 255

Val Asn Lys Leu Gln Arg Glu His Gln Lys Cys Gln Ile Arg Thr Gly
            260                 265                 270

Lys Leu Arg Asp Glu Tyr Val Glu Tyr Asp Lys Leu Leu Pro Ile
            275                 280                 285

Phe Ile Arg Phe Lys Thr Ser Ala Ile Thr Leu Gly Glu Phe Phe Lys
            290                 295                 300

Leu Glu Ile Pro Glu Leu Gly Ala Ser Asn Asp Asp Leu Lys Glu
305                 310                 315                 320

Thr Ala Ser Pro Met Ile Thr Asn Gln Ile Leu Pro Pro Asn Gln Arg
                325                 330                 335

Leu Trp Glu Asn Glu Asp Thr Arg Lys Phe Tyr Glu Ile Leu Pro Asp
            340                 345                 350

Ile Ser Lys Thr Val Glu Glu Ser Gln Ser Ser Lys Thr Glu Lys Asp
            355                 360                 365

Ser Asn Val Asn Ser Lys Asn Ile Asn Leu Phe Phe Thr Asp Leu Glu
            370                 375                 380

Met Ala Asp Cys Lys Asp Ile Ile Asp Asp Leu Ser Asn Arg Tyr Trp
385                 390                 395                 400

Ser Ser Tyr Leu Asp Asn Lys Ala Thr Arg Asn Arg Ile Leu Lys Phe
                405                 410                 415

Phe Met Glu Thr Gln Asp Trp Ser Lys Leu Pro Val Tyr Ser Arg Phe
            420                 425                 430

Ile Ala Thr Asn Ser Lys Tyr Met Pro Glu Ile Val Ser Glu Phe Ile
            435                 440                 445

Asn Tyr Leu Asp Asn Gly Phe Arg Ser Gln Leu His Ser Asn Lys Ile
            450                 455                 460

Asn Val Lys Asn Ile Ile Phe Phe Ser Glu Met Ile Lys Phe Gln Leu
465                 470                 475                 480

Ile Pro Ser Phe Met Ile Phe His Lys Ile Arg Thr Leu Ile Met Tyr
                485                 490                 495

Met Gln Val Pro Asn Asn Val Glu Ile Leu Thr Val Leu Leu Glu His
            500                 505                 510

Ser Gly Lys Phe Leu Leu Asn Lys Pro Glu Tyr Lys Glu Leu Met Glu
```

-continued

```
            515                 520                 525
Lys Met Val Gln Leu Ile Lys Asp Lys Lys Asn Asp Arg Gln Leu Asn
    530                 535                 540

Met Asn Met Lys Ser Ala Leu Glu Asn Ile Ile Thr Leu Leu Tyr Pro
545                 550                 555                 560

Pro Ser Val Lys Ser Leu Asn Val Thr Val Lys Thr Ile Thr Pro Glu
                565                 570                 575

Gln Gln Phe Tyr Arg Ile Leu Ile Arg Ser Glu Leu Ser Ser Leu Asp
            580                 585                 590

Phe Lys His Ile Val Lys Leu Val Arg Lys Ala His Trp Asp Asp Val
        595                 600                 605

Ala Ile Gln Lys Val Leu Phe Ser Leu Phe Ser Lys Pro His Lys Ile
610                 615                 620

Ser Tyr Gln Asn Ile Pro Leu Leu Thr Lys Val Leu Gly Gly Leu Tyr
625                 630                 635                 640

Ser Tyr Arg Arg Asp Phe Val Ile Arg Cys Ile Asp Gln Val Leu Glu
                645                 650                 655

Asn Ile Glu Arg Gly Leu Glu Ile Asn Asp Tyr Gly Gln Asn Met His
            660                 665                 670

Arg Ile Ser Asn Val Arg Tyr Leu Thr Glu Ile Phe Asn Phe Glu Met
        675                 680                 685

Ile Lys Ser Asp Val Leu Leu Asp Thr Ile Tyr His Ile Ile Arg Phe
690                 695                 700

Gly His Ile Asn Asn Gln Pro Asn Pro Phe Tyr Leu Asn Tyr Ser Asp
705                 710                 715                 720

Pro Pro Asp Asn Tyr Phe Arg Ile Gln Leu Val Thr Thr Ile Leu Leu
                725                 730                 735

Asn Ile Asn Arg Thr Pro Ala Ala Phe Thr Lys Lys Cys Lys Leu Leu
            740                 745                 750

Leu Arg Phe Phe Glu Tyr Tyr Thr Phe Ile Lys Glu Gln Pro Leu Pro
        755                 760                 765

Lys Glu Thr Glu Phe Arg Val Ser Ser Thr Phe Lys Lys Tyr Glu Asn
770                 775                 780

Ile Phe Gly Asn Thr Lys Phe Glu Arg Ser Glu Asn Leu Val Glu Ser
785                 790                 795                 800

Ala Ser Arg Leu Glu Ser Leu Leu Lys Ser Leu Asn Ala Ile Lys Ser
                805                 810                 815

Lys Asp Asp Arg Val Lys Gly Ser Ser Ala Ser Ile His Asn Gly Lys
            820                 825                 830

Glu Ser Ala Val Pro Ile Glu Ser Ile Thr Glu Asp Asp Glu Asp Glu
        835                 840                 845

Asp Asp Glu Asn Asp Asp Gly Val Asp Leu Leu Gly Glu Asp Glu Asp
850                 855                 860

Ala Glu Ile Ser Thr Pro Asn Thr Glu Ser Ala Pro Gly Lys His Gln
865                 870                 875                 880

Ala Lys Gln Asp Glu Ser Glu Asp Glu Asp Glu Asp Asp Glu
                885                 890                 895

Asp Asp Asp Asp Asp Asp Asp Asp Asp Asp Gly Glu Glu Gly
            900                 905                 910

Asp Glu Asp Asp Asp Glu Asp Asp Asp Glu Asp Asp Asp Glu
        915                 920                 925

Glu Glu Glu Asp Ser Asp Ser Asp Leu Glu Tyr Gly Gly Asp Leu Asp
930                 935                 940
```

```
Ala Asp Arg Asp Ile Glu Met Lys Arg Met Tyr Glu Glu Tyr Glu Arg
945                 950                 955                 960

Lys Leu Lys Asp Glu Glu Arg Lys Ala Glu Glu Leu Glu Arg
                965                 970                 975

Gln Phe Gln Lys Met Met Gln Glu Ser Ile Asp Ala Arg Lys Ser Glu
            980                 985                 990

Lys Val Val Ala Ser Lys Ile Pro Val Ile Ser Lys Pro Val Ser Val
                995                 1000                1005

Gln Lys Pro Leu Leu Leu Lys Lys Ser Glu Pro Ser Ser Ser Lys
        1010                1015                1020

Glu Thr Tyr Glu Glu Leu Ser Lys Pro Lys Lys Ile Ala Phe Thr Phe
1025                1030                1035                104

Leu Thr Lys Ser Gly Lys Lys Thr Gln Ser Arg Ile Leu Gln Leu Pro
                1045                1050                1055

Thr Asp Val Lys Phe Val Ser Asp Val Leu Glu Glu Glu Lys Leu
                1060                1065                1070

Lys Thr Glu Arg Asn Lys Ile Lys Lys Ile Val Leu Lys Arg Ser Phe
        1075                1080                1085

Asp (2) INFORMATION FOR SEQ ID NO:3:

(i) SEQUENCE CHARACTERISTICS:
        (A) LENGTH: 2295 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATCACGAATC AGATATTGCC ACCCAACCAA CGATTATGGG AAAATGAAGA TACAAGGAAA      60

TTTTATGAAA TCTTACCAGA TATCTCAAAA ACAGTAGAAG AATCACAATC TTCTAAAACA    120

GAAAAAGATT CAAACGTTAA CTCAAAAAAT ATCAATCTAT TCTTTACGGA TTTGGAAATG    180

GCAGATTGTA AAGATATAAT CGATGACCTT TCAAATAGAT ATTGGTCATC ATATTTGGAC    240

AACAAAGCCA CAAGAAATCG AATATTGAAA TTTTTCATGG AAACACAAGA TTGGAGCAAA    300

CTGCCAGTGT ATTCCAGATT TATTGCAACA AATAGCAAAT ATATGCCGGA AATTGTTTCT    360

GAGTTTATTA ACTACCTAGA CAATGGCTTC AGGAGTCAAT TACATTCTAA TAAGATTAAC    420

GTTAAAAACA TCATCTTCTT CAGTGAAATG ATTAAATTTC AATTAATACC ATCGTTTATG    480

ATTTTTCATA AGATTAGAAC ATTAATCATG TATATGCAAG TTCCAAATAA CGTAGAAATT    540

TTGACGGTTT TGTTGGAGCA CTCAGGGAAA TTTCTGCTAA ATAAGCCAGA ATATAAGGAA    600

TTAATGAAAA AAATGGTCCA ACTAATCAAG GATAAAAAAA ATGATAGGCA ATTGAACATG    660

AACATGAAAA GCGCCTTAGA AAACATAATT ACTTTACTTT ATCCCCCTTC TGTAAAATCA    720

TTAAATGTTA CGGTAAAAAC AATAACGCCT GAACAACAGT TTTATCGCAT ATTAATTAGA    780

AGTGAACTAA GTAGCCTAGA CTTCAAACAC ATTGTCAAGT TGGTTCGGAA AGCTCACTGG    840

GACGATGTAG CTATTCAGAA AGTGCTGTTT TCTCTGTTTT CAAAACCACA TAAGATTAGC    900

TATCAAAATA TTCCCTTATT AACAAAAGTT CTAGGCGGTC TATACAGTTA CCGCCGCGAT    960

TTCGTCATCA GATGTATAGA CCAAGTACTG GAAAACATTG AGCGAGGCTT AGAAATTAAC   1020

GATTATGGAC AAAACATGCA TAGAATATCA AATGTCAGAT ACTTAACTGA AATATTCAAC   1080
```

-continued

```
TTTGAAATGA TAAAATCCGA TGTTTTGTTA GATACTATCT ACCACATTAT TCGGTTTGGT    1140

CATATCAACA ATCAACCCAA TCCATTTTAT TTAAACTACT CAGATCCACC GGATAATTAT    1200

TTCAGGATTC AACTAGTCAC TACAATTCTG TTAAATATCA ACAGGACCCC TGCAGCTTTT    1260

ACTAAGAAAT GCAAACTTTT GCTGAGGTTT TTCGAGTATT ATACTTTTAT TAAAGAACAA    1320

CCTTTACCCA AGGAAACAGA ATTCAGAGTT TCAAGCACAT TTAAAAAATA TGAGAATATT    1380

TTCGGAAACA CTAAATTTGA AAGGTCAGAA AATTTGGTAG AAAGTGCCTC AAGGTTGGAA    1440

AGTTTACTGA AATCATTAAA CGCAATAAAA AGTAAAGACG ACAGAGTGAA GGGATCTTCT    1500

GCAAGCATTC ACAACGGTAA GGAGAGTGCT GTTCCTATCG AGTCAATCAC CGAAGATGAT    1560

GAGGATGAAG ATGATGAAAA CGACGATGGT GTCGATTTAC TAGGAGAAGA TGAAGACGCG    1620

GAGATAAGTA CACCGAACAC AGAGTCAGCG CCAGGAAAAC ATCAGGCAAA GCAAGACGAA    1680

AGTGAAGATG AAGACGATGA GGACGATGAC GAGGATGATG ACGATGACGA TGACGATGAT    1740

GATGATGATG GAGAAGAAGG CGATGAGGAT GATGATGAAG ATGATGATGA TGAGGATGAT    1800

GATGATGAAG AAGAAGAAGA CAGCGACTCT GATTTGGAGT ATGGTGGTGA TCTTGACGCA    1860

GACAGAGATA TTGAAATGAA ACGAATGTAT GAAGAGTACG AGAGAAAACT AAAGGATGAG    1920

GAAGAAAGGA AAGCGGAAGA AGAATTGGAA AGGCAATTTC AGAAAATGAT GCAAGAATCC    1980

ATAGACGCAA GGAAAAGCGA AAAGGTTGTT GCCAGTAAAA TTCCAGTAAT TTCGAAGCCA    2040

GTCAGCGTTC AAAAACCTTT ATTATTAAAA AAGAGTGAAG AACCTTCTTC AAGCAAGGAG    2100

ACCTACGAAG AGTTATCCAA GCCAAAGAAG ATTGCATTTA CGTTCTTGAC TAAAAGCGGT    2160

AAGAAGACAC AATCAAGAAT TTTACAATTA CCAACGGATG TGAAATTTGT CTCTGATGTC    2220

CTTGAAGAAG AAGAGAAACT AAAAACCGAG CGAAACAAGA TTAAAAAGAT TGTTTTAAAA    2280

CGTTCTTTCG ACTGA                                                    2295
```

(2) INFORMATION FOR SEQ ID NO:4:

(i) SEQUENCE CHARACTERISTICS:
        (A) LENGTH: 764 amino acids
        (B) TYPE: amino acid
        (D) TOPOLOGY: linear (ii) MOLECULE TYPE: peptide (xi) SEQUENCE DESCRIPTION: SEQ ID NO:4:

```
Ile Thr Asn Gln Ile Leu Pro Pro Asn Gln Arg Leu Trp Glu Asn Glu
  1               5                  10                  15

Asp Thr Arg Lys Phe Tyr Glu Ile Leu Pro Asp Ile Ser Lys Thr Val
             20                  25                  30

Glu Glu Ser Gln Ser Ser Lys Thr Glu Lys Asp Ser Asn Val Asn Ser
         35                  40                  45

Lys Asn Ile Asn Leu Phe Phe Thr Asp Leu Glu Met Ala Asp Cys Lys
     50                  55                  60

Asp Ile Ile Asp Asp Leu Ser Asn Arg Tyr Trp Ser Ser Tyr Leu Asp
 65                  70                  75                  80

Asn Lys Ala Thr Arg Asn Arg Ile Leu Lys Phe Phe Met Glu Thr Gln
                 85                  90                  95

Asp Trp Ser Lys Leu Pro Val Tyr Ser Arg Phe Ile Ala Thr Asn Ser
            100                 105                 110

Lys Tyr Met Pro Glu Ile Val Ser Glu Phe Ile Asn Tyr Leu Asp Asn
        115                 120                 125

Gly Phe Arg Ser Gln Leu His Ser Asn Lys Ile Asn Val Lys Asn Ile
```

-continued

```
            130                 135                 140
Ile Phe Phe Ser Glu Met Ile Lys Phe Gln Leu Ile Pro Ser Phe Met
145                 150                 155                 160
Ile Phe His Lys Ile Arg Thr Leu Ile Met Tyr Met Gln Val Pro Asn
                165                 170                 175
Asn Val Glu Ile Leu Thr Val Leu Leu Glu His Ser Gly Lys Phe Leu
                180                 185                 190
Leu Asn Lys Pro Glu Tyr Lys Glu Leu Met Glu Lys Met Val Gln Leu
            195                 200                 205
Ile Lys Asp Lys Lys Asn Asp Arg Gln Leu Asn Met Asn Met Lys Ser
            210                 215                 220
Ala Leu Glu Asn Ile Ile Thr Leu Leu Tyr Pro Pro Ser Val Lys Ser
225                 230                 235                 240
Leu Asn Val Thr Val Lys Thr Ile Thr Pro Glu Gln Gln Phe Tyr Arg
                245                 250                 255
Ile Leu Ile Arg Ser Glu Leu Ser Ser Leu Asp Phe Lys His Ile Val
                260                 265                 270
Lys Leu Val Arg Lys Ala His Trp Asp Asp Val Ala Ile Gln Lys Val
            275                 280                 285
Leu Phe Ser Leu Phe Ser Lys Pro His Lys Ile Ser Tyr Gln Asn Ile
            290                 295                 300
Pro Leu Leu Thr Lys Val Leu Gly Gly Leu Tyr Ser Tyr Arg Arg Asp
305                 310                 315                 320
Phe Val Ile Arg Cys Ile Asp Gln Val Leu Glu Asn Ile Glu Arg Gly
                325                 330                 335
Leu Glu Ile Asn Asp Tyr Gly Gln Asn Met His Arg Ile Ser Asn Val
                340                 345                 350
Arg Tyr Leu Thr Glu Ile Phe Asn Phe Glu Met Ile Lys Ser Asp Val
                355                 360                 365
Leu Leu Asp Thr Ile Tyr His Ile Ile Arg Phe Gly His Ile Asn Asn
            370                 375                 380
Gln Pro Asn Pro Phe Tyr Leu Asn Tyr Ser Asp Pro Pro Asp Asn Tyr
385                 390                 395                 400
Phe Arg Ile Gln Leu Val Thr Thr Ile Leu Leu Asn Ile Asn Arg Thr
                405                 410                 415
Pro Ala Ala Phe Thr Lys Lys Cys Lys Leu Leu Leu Arg Phe Phe Glu
                420                 425                 430
Tyr Tyr Thr Phe Ile Lys Glu Gln Pro Leu Pro Lys Glu Thr Glu Phe
            435                 440                 445
Arg Val Ser Ser Thr Phe Lys Lys Tyr Glu Asn Ile Phe Gly Asn Thr
            450                 455                 460
Lys Phe Glu Arg Ser Glu Asn Leu Val Glu Ser Ala Ser Arg Leu Glu
465                 470                 475                 480
Ser Leu Leu Lys Ser Leu Asn Ala Ile Lys Ser Lys Asp Asp Arg Val
                485                 490                 495
Lys Gly Ser Ser Ala Ser Ile His Asn Gly Lys Glu Ser Ala Val Pro
                500                 505                 510
Ile Glu Ser Ile Thr Glu Asp Asp Glu Asp Asp Glu Asp Glu Asn Asp
            515                 520                 525
Asp Gly Val Asp Leu Leu Gly Glu Asp Glu Asp Ala Glu Ile Ser Thr
            530                 535                 540
Pro Asn Thr Glu Ser Ala Pro Gly Lys His Gln Ala Lys Gln Asp Glu
545                 550                 555                 560
```

```
Ser Glu Asp Glu Asp Asp Glu Asp Asp Asp Glu Asp Asp Asp Asp
            565                 570                 575
Asp Asp Asp Asp Asp Asp Gly Glu Glu Gly Asp Glu Asp Asp Asp
            580                 585                 590
Glu Asp Asp Asp Glu Asp Asp Asp Glu Glu Glu Glu Asp Asp Ser
            595                 600                 605
Asp Ser Asp Leu Glu Tyr Gly Gly Asp Leu Asp Ala Asp Arg Asp Ile
            610                 615                 620
Glu Met Lys Arg Met Tyr Glu Glu Tyr Glu Arg Lys Leu Lys Asp Glu
625                 630                 635                 640
Glu Glu Arg Lys Ala Glu Glu Leu Glu Arg Gln Phe Gln Lys Met
            645                 650                 655
Met Gln Glu Ser Ile Asp Ala Arg Lys Ser Glu Lys Val Val Ala Ser
            660                 665                 670
Lys Ile Pro Val Ile Ser Lys Pro Val Ser Val Gln Lys Pro Leu Leu
            675                 680                 685
Leu Lys Lys Ser Glu Glu Pro Ser Ser Ser Lys Glu Thr Tyr Glu Glu
            690                 695                 700
Leu Ser Lys Pro Lys Lys Ile Ala Phe Thr Phe Leu Thr Lys Ser Gly
705                 710                 715                 720
Lys Lys Thr Gln Ser Arg Ile Leu Gln Leu Pro Thr Asp Val Lys Phe
            725                 730                 735
Val Ser Asp Val Leu Glu Glu Glu Lys Leu Lys Thr Glu Arg Asn
            740                 745                 750
Lys Ile Lys Lys Ile Val Leu Lys Arg Ser Phe Asp
            755                 760

(2) INFORMATION FOR SEQ ID NO:5:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:5:

CCGGAATTCA TGGTCGGTTC CGGTTCT                                        27

(2) INFORMATION FOR SEQ ID NO:6:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: oligonucleotide (xi) SEQUENCE DESCRIPTION: SEQ ID NO:6:

AGTGACTTGA GCCTC                                                     15

(2) INFORMATION FOR SEQ ID NO:7:

(i) SEQUENCE CHARACTERISTICS:
        (A) LENGTH: 3546 base pairs
        (B) TYPE: nucleic acid
        (C) STRANDEDNESS: single
        (D) TOPOLOGY: linear
```

(ii) MOLECULE TYPE: cDNA (ix) FEATURE:
    (A) NAME/KEY: Coding Sequence
    (B) LOCATION: 402...3314

(xi) SEQUENCE DESCRIPTION: SEQ ID NO:7:

```
GAATTCATGA ACGGGAAATA AGAAAAACAA AAAGAAAATA TACATAGTTA GTTACTATCC        60

ACTCAATAAT ATTAAACGAG TGAATGCTTT TACTTTTAAC TTTAGTTTAA TCTTAATTTA       120

CATTATTTTA GTATCATCAG TTTCCCTTTG CTTACTTGAT TTGGGAGGGA CACCTTTATA       180

CGCTTTCGTA CTAACTGATC AAATGAAAAG CTTACCAGAA ACTTACGATG CTATTGTGAA       240

GGAGAAAAAA AAAGCGAAAA GAGGCATCGT TTTAACGCAC ACTAACAGAA GACTCTATTT       300

CTCTTGTCAG CCAACAAACG TTGAAGATTT CATCAGGAAA GAAGGAAGGG CAGCAAGACC       360

GAATATACTT TTTATATTAC ATCAATCATT GTCATTATCA A ATG GTC GGT TCC GGT       416
                                             Met Val Gly Ser Gly
                                              1               5

TCT CAC ACT CCT TAT GAT ATA TCA AAC TCT CCA TCT GAT GTA AAT GTC         464
Ser His Thr Pro Tyr Asp Ile Ser Asn Ser Pro Ser Asp Val Asn Val
             10                  15                  20

CAA CCC GCA ACA CAA CTA AAT TCC ACC TTG GTG GAG GAT GAC GAT GTA         512
Gln Pro Ala Thr Gln Leu Asn Ser Thr Leu Val Glu Asp Asp Asp Val
         25                  30                  35

GAT AAT CAG CTA TTT GAA GAG GCT CAA GTC ACT GAG ACT GGA TTC CGT         560
Asp Asn Gln Leu Phe Glu Glu Ala Gln Val Thr Glu Thr Gly Phe Arg
     40                  45                  50

TCG CCT TCA GCT TCA GAC AAT TCA TGT GCG TAT TGT GGT ATA GAT TCT         608
Ser Pro Ser Ala Ser Asp Asn Ser Cys Ala Tyr Cys Gly Ile Asp Ser
 55                  60                  65

GCA AAG TGT GTC ATC AAA TGT AAT TCA TGT AAG AAA TGG TTT TGT AAC         656
Ala Lys Cys Val Ile Lys Cys Asn Ser Cys Lys Lys Trp Phe Cys Asn
 70                  75                  80                  85

ACT AAA AAC GGT ACA AGC AGC TCC CAC ATT GTT AAT CAC TTA GTT TTA         704
Thr Lys Asn Gly Thr Ser Ser Ser His Ile Val Asn His Leu Val Leu
             90                  95                 100

TCC CAC CAT AAC GTA GTT TCT TTA CAT CCA GAT TCT GAC TTA GGG GAT         752
Ser His His Asn Val Val Ser Leu His Pro Asp Ser Asp Leu Gly Asp
         105                 110                 115

ACC GTT TTG GAA TGT TAT AAC TGT GGA CGT AAG AAC GTG TTT TTA TTG         800
Thr Val Leu Glu Cys Tyr Asn Cys Gly Arg Lys Asn Val Phe Leu Leu
     120                 125                 130

GGA TTT GTT TCC GCT AAA AGT GAG GCC GTG GTT GTT TTA CTT TGT AGA         848
Gly Phe Val Ser Ala Lys Ser Glu Ala Val Val Val Leu Leu Cys Arg
 135                 140                 145

ATA CCT TGT GCC CAG ACG AAA AAT GCG AAC TGG GAT ACT GAT CAA TGG         896
Ile Pro Cys Ala Gln Thr Lys Asn Ala Asn Trp Asp Thr Asp Gln Trp
150                 155                 160                 165

CAA CCA TTA ATT GAA GAC AGA CAA CTT TTA TCA TGG GTC GCA GAG CAA         944
Gln Pro Leu Ile Glu Asp Arg Gln Leu Leu Ser Trp Val Ala Glu Gln
             170                 175                 180

CCA ACT GAA GAA GAA AAA TTG AAA GCT CGT TTA ATC ACT CCT AGC CAA         992
Pro Thr Glu Glu Glu Lys Leu Lys Ala Arg Leu Ile Thr Pro Ser Gln
         185                 190                 195

ATT TCC AAG TTG GAG GCA AAA TGG AGA TCC AAT AAA GAC GCT ACA ATT        1040
Ile Ser Lys Leu Glu Ala Lys Trp Arg Ser Asn Lys Asp Ala Thr Ile
     200                 205                 210

AAT GAT ATT GAC GCC CCA GAG GAA CAG GAA GCA ATC CCA CCT TTA CTA        1088
Asn Asp Ile Asp Ala Pro Glu Glu Gln Glu Ala Ile Pro Pro Leu Leu
 215                 220                 225
```

-continued

```
TTG AGA TAT CAA GAC GCC TAC GAA TAC CAA AGA TCT TAC GGG CCT TTA      1136
Leu Arg Tyr Gln Asp Ala Tyr Glu Tyr Gln Arg Ser Tyr Gly Pro Leu
230                 235                 240                 245

ATC AAA TTG GAG GCC GAC TAT GAT AAA CAA CTC AAG GAA TCT CAA GCT      1184
Ile Lys Leu Glu Ala Asp Tyr Asp Lys Gln Leu Lys Glu Ser Gln Ala
                250                 255                 260

TTA GAA CAT ATT TCT GTT TCA TGG TCC TTA GCT TTA AAT AAT AGG CAT      1232
Leu Glu His Ile Ser Val Ser Trp Ser Leu Ala Leu Asn Asn Arg His
            265                 270                 275

TTA GCA TCT TTC ACT TTA TCT ACT TTC GAA TCT AAC GAG TTG AAA GTT      1280
Leu Ala Ser Phe Thr Leu Ser Thr Phe Glu Ser Asn Glu Leu Lys Val
        280                 285                 290

GCC ATC GGT GAT GAA ATG ATA CTA TGG TAC TCT GGC ATG CAA CAT CCT      1328
Ala Ile Gly Asp Glu Met Ile Leu Trp Tyr Ser Gly Met Gln His Pro
    295                 300                 305

GAT TGG GAA GGT CGT GGT TAC ATT GTT CGG TTA CCA AAT AGC TTC CAG      1376
Asp Trp Glu Gly Arg Gly Tyr Ile Val Arg Leu Pro Asn Ser Phe Gln
310                 315                 320                 325

GAC ACA TTC ACA TTA GAG TTA AAA CCA AGT AAA ACG CCA CCT CCA ACA      1424
Asp Thr Phe Thr Leu Glu Leu Lys Pro Ser Lys Thr Pro Pro Pro Thr
                330                 335                 340

CAT TTG ACC ACT GGT TTT ACT GCT GAG TTC ATC TGG AAA GGT ACC TCT      1472
His Leu Thr Thr Gly Phe Thr Ala Glu Phe Ile Trp Lys Gly Thr Ser
            345                 350                 355

TAT GAC AGG ATG CAA GAC GCA TTG AAA AAA TTT GCC ATT GAT AAA AAA      1520
Tyr Asp Arg Met Gln Asp Ala Leu Lys Lys Phe Ala Ile Asp Lys Lys
        360                 365                 370

TCT ATT TCA GGT TAT TTG TAC TAT AAA ATT TTA GGC CAT CAA GTG GTT      1568
Ser Ile Ser Gly Tyr Leu Tyr Tyr Lys Ile Leu Gly His Gln Val Val
    375                 380                 385

GAC ATT TCA TTT GAT GTC CCA TTA CCT AAG GAG TTT TCA ATT CCG AAT      1616
Asp Ile Ser Phe Asp Val Pro Leu Pro Lys Glu Phe Ser Ile Pro Asn
390                 395                 400                 405

TTT GCA CAA TTA AAC TCA TCC CAG TCG AAC GCT GTT AGT CAT GTA TTA      1664
Phe Ala Gln Leu Asn Ser Ser Gln Ser Asn Ala Val Ser His Val Leu
                410                 415                 420

CAA CGT CCG TTA TCT TTA ATT CAA GGC CCA CCA GGC ACT GGT AAA ACA      1712
Gln Arg Pro Leu Ser Leu Ile Gln Gly Pro Pro Gly Thr Gly Lys Thr
            425                 430                 435

GTT ACT TCA GCA ACG ATT GTG TAT CAC CTT TCC AAA ATA CAC AAG GAT      1760
Val Thr Ser Ala Thr Ile Val Tyr His Leu Ser Lys Ile His Lys Asp
        440                 445                 450

AGA ATA TTG GTG TGT GCC CCA TCA AAC GTT GCT GTA GAT CAT TTG GCT      1808
Arg Ile Leu Val Cys Ala Pro Ser Asn Val Ala Val Asp His Leu Ala
    455                 460                 465

GCC AAA TTA CGT GAC TTG GGT TTA AAA GTT GTT AGA CTT ACC GCG AAA      1856
Ala Lys Leu Arg Asp Leu Gly Leu Lys Val Val Arg Leu Thr Ala Lys
470                 475                 480                 485

AGT AGA GAA GAT GTG GAG AGT TCC GTC TCC AAC TTA GCA TTG CAT AAT      1904
Ser Arg Glu Asp Val Glu Ser Ser Val Ser Asn Leu Ala Leu His Asn
                490                 495                 500

TTG GTT GGC CGT GGT GCT AAA GGG GAA TTA AAA AAC CTA TTA AAG TTA      1952
Leu Val Gly Arg Gly Ala Lys Gly Glu Leu Lys Asn Leu Leu Lys Leu
            505                 510                 515

AAG GAT GAA GTT GGC GAA TTA TCT GCT TCT GAT ACA AAA CGG TTT GTT      2000
Lys Asp Glu Val Gly Glu Leu Ser Ala Ser Asp Thr Lys Arg Phe Val
        520                 525                 530

AAA TTA GTA AGG AAA ACA GAA GCA GAA ATT CTC AAT AAG GCA GAT GTC      2048
Lys Leu Val Arg Lys Thr Glu Ala Glu Ile Leu Asn Lys Ala Asp Val
```

-continued

```
           535                 540                 545
GTA TGT TGC ACA TGT GTT GGT GCT GGT GAT AAG CGC TTA GAC ACT AAA    2096
Val Cys Cys Thr Cys Val Gly Ala Gly Asp Lys Arg Leu Asp Thr Lys
550                 555                 560                 565

TTT AGG ACT GTG TTA ATT GAT GAA AGT ACT CAA GCT TCT GAG CCG GAA    2144
Phe Arg Thr Val Leu Ile Asp Glu Ser Thr Gln Ala Ser Glu Pro Glu
                570                 575                 580

TGT TTA ATC CCA ATC GTT AAA GGT GCG AAA CAA GTT ATA CTT GTT GGT    2192
Cys Leu Ile Pro Ile Val Lys Gly Ala Lys Gln Val Ile Leu Val Gly
            585                 590                 595

GAT CAC CAG CAA CTG GGC CCA GTC ATA TTG GAA CGA AAG GCG GCA GAC    2240
Asp His Gln Gln Leu Gly Pro Val Ile Leu Glu Arg Lys Ala Ala Asp
        600                 605                 610

GCT GGT TTG AAA CAA TCT CTC TTT GAA AGA TTA ATC TCT CTA GGC CAC    2288
Ala Gly Leu Lys Gln Ser Leu Phe Glu Arg Leu Ile Ser Leu Gly His
    615                 620                 625

GTA CCG ATT CGT TTG GAA GTT CAA TAC CGT ATG AAT CCT TAT TTG AGT    2336
Val Pro Ile Arg Leu Glu Val Gln Tyr Arg Met Asn Pro Tyr Leu Ser
630                 635                 640                 645

GAG TTT CCA AGT AAC ATG TTT TAT GAA GGC AGC CTA CAA AAT GGT GTA    2384
Glu Phe Pro Ser Asn Met Phe Tyr Glu Gly Ser Leu Gln Asn Gly Val
                650                 655                 660

ACG ATT GAA CAG CGT ACC GTT CCC AAC AGC AAA TTC CCA TGG CCA ATT    2432
Thr Ile Glu Gln Arg Thr Val Pro Asn Ser Lys Phe Pro Trp Pro Ile
            665                 670                 675

CGC GGT ATA CCA ATG ATG TTT TGG GCC AAT TAC GGT AGA GAG GAG ATT    2480
Arg Gly Ile Pro Met Met Phe Trp Ala Asn Tyr Gly Arg Glu Glu Ile
        680                 685                 690

TCT GCT AAC GGT ACT TCC TTC TTA AAC AGA ATT GAA GCC ATG AAT TGT    2528
Ser Ala Asn Gly Thr Ser Phe Leu Asn Arg Ile Glu Ala Met Asn Cys
    695                 700                 705

GAA CGA ATC ATC ACT AAA CTT TTC AGA GAC GGT GTC AAG CCC GAG CAA    2576
Glu Arg Ile Ile Thr Lys Leu Phe Arg Asp Gly Val Lys Pro Glu Gln
710                 715                 720                 725

ATT GGT GTT ATC ACA CCA TAT GAG GGA CAA AGA GCT TAT ATT TTA CAA    2624
Ile Gly Val Ile Thr Pro Tyr Glu Gly Gln Arg Ala Tyr Ile Leu Gln
                730                 735                 740

TAT ATG CAA ATG AAT GGT TCA TTG GAT AAG GAT TTG TAT ATC AAA GTG    2672
Tyr Met Gln Met Asn Gly Ser Leu Asp Lys Asp Leu Tyr Ile Lys Val
            745                 750                 755

GAA GTT GCC TCA GTT GAT GCA TTC CAA GGT CGT GAA AAG GAT TAC ATA    2720
Glu Val Ala Ser Val Asp Ala Phe Gln Gly Arg Glu Lys Asp Tyr Ile
        760                 765                 770

ATC TTA TCG TGT GTT CGT GCC AAT GAA CAA CAG GCC ATT GGT TTC TTA    2768
Ile Leu Ser Cys Val Arg Ala Asn Glu Gln Gln Ala Ile Gly Phe Leu
    775                 780                 785

CGT GAT CCT CGT CGT CTA AAC GTG GGT CTA ACC CGT GCC AAA TAT GGT    2816
Arg Asp Pro Arg Arg Leu Asn Val Gly Leu Thr Arg Ala Lys Tyr Gly
790                 795                 800                 805

CTA GTT ATT CTT GGT AAT CCT AGA TCT TTG GCA AGA AAC ACA TTA TGG    2864
Leu Val Ile Leu Gly Asn Pro Arg Ser Leu Ala Arg Asn Thr Leu Trp
                810                 815                 820

AAC CAT CTG TTA ATC CAC TTC AGA GAG AAG GGT TGT TTA GTC GAA GGT    2912
Asn His Leu Leu Ile His Phe Arg Glu Lys Gly Cys Leu Val Glu Gly
            825                 830                 835

ACG TTG GAT AAC TTA CAG TTA TGC ACT GTT CAA TTA GTT CGT CCT CAG    2960
Thr Leu Asp Asn Leu Gln Leu Cys Thr Val Gln Leu Val Arg Pro Gln
        840                 845                 850

CCA AGA AAG ACT GAA CGG CCA ATG AAC GCT CAA TTT AAC GTA GAA TCT    3008
```

```
Pro Arg Lys Thr Glu Arg Pro Met Asn Ala Gln Phe Asn Val Glu Ser
    855                 860                 865

GAA ATG GGT GAC TTT CCG AAG TTC CAG GAT TTT GAT GCA CAG AGT ATG      3056
Glu Met Gly Asp Phe Pro Lys Phe Gln Asp Phe Asp Ala Gln Ser Met
870                 875                 880                 885

GTG TCA TTC AGT GGT CAA ATT GGG GAC TTT GGT AAT GCA TTT GTT GAC      3104
Val Ser Phe Ser Gly Gln Ile Gly Asp Phe Gly Asn Ala Phe Val Asp
                890                 895                 900

AAC ACA GAA CTT TCT TCT TAC ATC AAT AAT GAA TAT TGG AAT TTT GAG      3152
Asn Thr Glu Leu Ser Ser Tyr Ile Asn Asn Glu Tyr Trp Asn Phe Glu
            905                 910                 915

AAT TTT AAA AGT GCT TTT TCT CAA AAG CAA AAT CGC AAT GAA ATT GAC      3200
Asn Phe Lys Ser Ala Phe Ser Gln Lys Gln Asn Arg Asn Glu Ile Asp
        920                 925                 930

GAT AGA AAT TTG TAC CAG GAG GAG GCT TCT CAT TTG AAC TCT AAC TTC      3248
Asp Arg Asn Leu Tyr Gln Glu Glu Ala Ser His Leu Asn Ser Asn Phe
    935                 940                 945

GCG AGA GAG TTA CAG AGA GAA GAA CAA AAG CAT GAA TTG TCA AAA GAC      3296
Ala Arg Glu Leu Gln Arg Glu Glu Gln Lys His Glu Leu Ser Lys Asp
950                 955                 960                 965

TTC AGC AAT TTG GGA ATA TAATTCGGTG AACCCTGTTA AAATAAAATG             3344
Phe Ser Asn Leu Gly Ile
                970

TTAAACTTGG CTTGTGATAC AAAACGGCTC AACCGTGAAA TGAGCGCTGC AAAATTATTC    3404

GAGATAGACT CGCAATTTGC ACAATTGTAA CCTGAAAAAT TTTTTTACTT TTCCGGAGGT    3464

GCATCTATCA TTACAGTATG TGATAAAGGG GCATGGACTT GATATCCTAG CCTACTAATC    3524

TCTTTGCTAA AACATGTTGC AA                                             3546

(2) INFORMATION FOR SEQ ID NO:8:

(i) SEQUENCE CHARACTERISTICS:
        (A) LENGTH: 971 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:8:

Met Val Gly Ser Gly Ser His Thr Pro Tyr Asp Ile Ser Asn Ser Pro
 1               5                  10                  15

Ser Asp Val Asn Val Gln Pro Ala Thr Gln Leu Asn Ser Thr Leu Val
                20                  25                  30

Glu Asp Asp Val Asp Asn Gln Leu Phe Glu Glu Ala Gln Val Thr
            35                  40                  45

Glu Thr Gly Phe Arg Ser Pro Ser Ala Ser Asp Asn Ser Cys Ala Tyr
        50                  55                  60

Cys Gly Ile Asp Ser Ala Lys Cys Val Ile Lys Cys Asn Ser Cys Lys
65                  70                  75                  80

Lys Trp Phe Cys Asn Thr Lys Asn Gly Thr Ser Ser His Ile Val
                85                  90                  95

Asn His Leu Val Leu Ser His Asn Val Val Ser Leu His Pro Asp
            100                 105                 110

Ser Asp Leu Gly Asp Thr Val Leu Glu Cys Tyr Asn Cys Gly Arg Lys
        115                 120                 125

Asn Val Phe Leu Leu Gly Phe Val Ser Ala Lys Ser Glu Ala Val Val
    130                 135                 140
```

-continued

```
Val Leu Leu Cys Arg Ile Pro Cys Ala Gln Thr Lys Asn Ala Asn Trp
145                 150                 155                 160

Asp Thr Asp Gln Trp Gln Pro Leu Ile Glu Asp Arg Gln Leu Leu Ser
            165                 170                 175

Trp Val Ala Glu Gln Pro Thr Glu Glu Lys Leu Lys Ala Arg Leu
        180                 185                 190

Ile Thr Pro Ser Gln Ile Ser Lys Leu Glu Ala Lys Trp Arg Ser Asn
            195                 200                 205

Lys Asp Ala Thr Ile Asn Asp Ile Asp Ala Pro Glu Gln Glu Ala
    210                 215                 220

Ile Pro Pro Leu Leu Arg Tyr Gln Asp Ala Tyr Glu Tyr Gln Arg
225                 230                 235                 240

Ser Tyr Gly Pro Leu Ile Lys Leu Glu Ala Asp Tyr Asp Lys Gln Leu
                245                 250                 255

Lys Glu Ser Gln Ala Leu Glu His Ile Ser Val Ser Trp Ser Leu Ala
            260                 265                 270

Leu Asn Asn Arg His Leu Ala Ser Phe Thr Leu Ser Thr Phe Glu Ser
        275                 280                 285

Asn Glu Leu Lys Val Ala Ile Gly Asp Glu Met Ile Leu Trp Tyr Ser
290                 295                 300

Gly Met Gln His Pro Asp Trp Glu Gly Arg Gly Tyr Ile Val Arg Leu
305                 310                 315                 320

Pro Asn Ser Phe Gln Asp Thr Phe Thr Leu Glu Leu Lys Pro Ser Lys
                325                 330                 335

Thr Pro Pro Pro Thr His Leu Thr Thr Gly Phe Thr Ala Glu Phe Ile
            340                 345                 350

Trp Lys Gly Thr Ser Tyr Asp Arg Met Gln Asp Ala Leu Lys Lys Phe
        355                 360                 365

Ala Ile Asp Lys Lys Ser Ile Ser Gly Tyr Leu Tyr Tyr Lys Ile Leu
    370                 375                 380

Gly His Gln Val Val Asp Ile Ser Phe Asp Val Pro Leu Pro Lys Glu
385                 390                 395                 400

Phe Ser Ile Pro Asn Phe Ala Gln Leu Asn Ser Ser Gln Ser Asn Ala
                405                 410                 415

Val Ser His Val Leu Gln Arg Pro Leu Ser Leu Ile Gln Gly Pro Pro
            420                 425                 430

Gly Thr Gly Lys Thr Val Thr Ser Ala Thr Ile Val Tyr His Leu Ser
        435                 440                 445

Lys Ile His Lys Asp Arg Ile Leu Val Cys Ala Pro Ser Asn Val Ala
    450                 455                 460

Val Asp His Leu Ala Ala Lys Leu Arg Asp Leu Gly Leu Lys Val Val
465                 470                 475                 480

Arg Leu Thr Ala Lys Ser Arg Glu Asp Val Glu Ser Ser Val Ser Asn
                485                 490                 495

Leu Ala Leu His Asn Leu Val Gly Arg Gly Ala Lys Gly Glu Leu Lys
            500                 505                 510

Asn Leu Leu Lys Leu Lys Asp Glu Val Gly Glu Leu Ser Ala Ser Asp
        515                 520                 525

Thr Lys Arg Phe Val Lys Leu Val Arg Lys Thr Glu Ala Glu Ile Leu
    530                 535                 540

Asn Lys Ala Asp Val Val Cys Cys Thr Cys Val Gly Ala Gly Asp Lys
545                 550                 555                 560
```

```
Arg Leu Asp Thr Lys Phe Arg Thr Val Leu Ile Asp Glu Ser Thr Gln
            565                 570                 575
Ala Ser Glu Pro Glu Cys Leu Ile Pro Ile Val Lys Gly Ala Lys Gln
            580                 585                 590
Val Ile Leu Val Gly Asp His Gln Gln Leu Gly Pro Val Ile Leu Glu
            595                 600                 605
Arg Lys Ala Ala Asp Ala Gly Leu Lys Gln Ser Leu Phe Glu Arg Leu
610                 615                 620
Ile Ser Leu Gly His Val Pro Ile Arg Leu Glu Val Gln Tyr Arg Met
625                 630                 635                 640
Asn Pro Tyr Leu Ser Glu Phe Pro Ser Asn Met Phe Tyr Glu Gly Ser
            645                 650                 655
Leu Gln Asn Gly Val Thr Ile Glu Gln Arg Thr Val Pro Asn Ser Lys
            660                 665                 670
Phe Pro Trp Pro Ile Arg Gly Ile Pro Met Met Phe Trp Ala Asn Tyr
            675                 680                 685
Gly Arg Glu Glu Ile Ser Ala Asn Gly Thr Ser Phe Leu Asn Arg Ile
690                 695                 700
Glu Ala Met Asn Cys Glu Arg Ile Ile Thr Lys Leu Phe Arg Asp Gly
705                 710                 715                 720
Val Lys Pro Glu Gln Ile Gly Val Ile Thr Pro Tyr Glu Gly Gln Arg
            725                 730                 735
Ala Tyr Ile Leu Gln Tyr Met Gln Met Asn Gly Ser Leu Asp Lys Asp
            740                 745                 750
Leu Tyr Ile Lys Val Glu Val Ala Ser Val Asp Ala Phe Gln Gly Arg
            755                 760                 765
Glu Lys Asp Tyr Ile Ile Leu Ser Cys Val Arg Ala Asn Glu Gln Gln
770                 775                 780
Ala Ile Gly Phe Leu Arg Asp Pro Arg Arg Leu Asn Val Gly Leu Thr
785                 790                 795                 800
Arg Ala Lys Tyr Gly Leu Val Ile Leu Gly Asn Pro Arg Ser Leu Ala
            805                 810                 815
Arg Asn Thr Leu Trp Asn His Leu Leu Ile His Phe Arg Glu Lys Gly
            820                 825                 830
Cys Leu Val Glu Gly Thr Leu Asp Asn Leu Gln Leu Cys Thr Val Gln
            835                 840                 845
Leu Val Arg Pro Gln Pro Arg Lys Thr Glu Arg Pro Met Asn Ala Gln
850                 855                 860
Phe Asn Val Glu Ser Glu Met Gly Asp Phe Pro Lys Phe Gln Asp Phe
865                 870                 875                 880
Asp Ala Gln Ser Met Val Ser Phe Ser Gly Gln Ile Gly Asp Phe Gly
            885                 890                 895
Asn Ala Phe Val Asp Asn Thr Glu Leu Ser Ser Tyr Ile Asn Asn Glu
            900                 905                 910
Tyr Trp Asn Phe Glu Asn Phe Lys Ser Ala Phe Ser Gln Lys Gln Asn
            915                 920                 925
Arg Asn Glu Ile Asp Asp Arg Asn Leu Tyr Gln Glu Glu Ala Ser His
            930                 935                 940
Leu Asn Ser Asn Phe Ala Arg Glu Leu Gln Arg Glu Glu Gln Lys His
945                 950                 955                 960
Glu Leu Ser Lys Asp Phe Ser Asn Leu Gly Ile
            965                 970
```

(2) INFORMATION FOR SEQ ID NO:9:

(i) SEQUENCE CHARACTERISTICS:
        (A) LENGTH: 1960 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 428...1588

(xi) SEQUENCE DESCRIPTION: SEQ ID NO:9:

```
GAATTCTACT TGATAGGATT TTATTGCCGT CTTTTTCTAT AAGTTCTATA TCCTCAGTAT      60

CGTCTTCTTC CTCGTCTTCC TCCTCATGAC TAGTAGAGTG AGAAGATGAA TGATCAGAAT     120

TATTGATGAT TTCGTTATCT TCTAAAGTCA CCAAATCCCC ATGTAAATCA TCCAATGCAG     180

TGTTCATATT AATGATTGAG TAGATTGGTA CATATGCTAT TTCGGAAGAC TTTTGTTATT     240

CTATGGTTTA TCATCCCTTT ATTTATTTTG TGTATTGTTT GCTGATCAAA AGTTGAAAAT     300

TTTTCGCCTA AAAAGTAAGA TACAAAAGAA AATATTGTCG ATGATTATTG CATGAATATA     360

TCAGCAAAGA GGAAAGGAAA ACCTACTGAG GGACTTACAT TTCTGCTGAA ATATATAGTA     420

ATCTATC ATG AGC AAT GTG GCT GGG GAA TTG AAG AAT AGT GAG GGG AAA       469
        Met Ser Asn Val Ala Gly Glu Leu Lys Asn Ser Glu Gly Lys
         1               5                  10

AAG AAA GGC AGG GGA AAT AGG TAT CAT AAC AAG AAC AGA GGA AAA AGT       517
Lys Lys Gly Arg Gly Asn Arg Tyr His Asn Lys Asn Arg Gly Lys Ser
 15                  20                  25                  30

AAG AAT GAG ACG GTA GAT CCT AAA AAG AAT GAG AAT AAG GTT AAT AAT       565
Lys Asn Glu Thr Val Asp Pro Lys Lys Asn Glu Asn Lys Val Asn Asn
                 35                  40                  45

GCT ACT AAT GCT ACC CAC AAC AAT AGC AAA GGC AGA AGG AAT AAC AAG       613
Ala Thr Asn Ala Thr His Asn Asn Ser Lys Gly Arg Arg Asn Asn Lys
             50                  55                  60

AAA AGG AAC AGA GAG TAT TAT AAC TAT AAA AGA AAG GCT AGA TTG GGT       661
Lys Arg Asn Arg Glu Tyr Tyr Asn Tyr Lys Arg Lys Ala Arg Leu Gly
 65                  70                  75

AAA TCA ACC GAG AAT GAA GGA TTT AAG CTT GTT ATT AGA TTG CTA CCT       709
Lys Ser Thr Glu Asn Glu Gly Phe Lys Leu Val Ile Arg Leu Leu Pro
 80                  85                  90

CCA AAT TTG ACT GCA GAT GAA TTT TTT GCC ATC TTA CGA GAT AAT AAT       757
Pro Asn Leu Thr Ala Asp Glu Phe Phe Ala Ile Leu Arg Asp Asn Asn
 95                 100                 105                 110

AAC GAT GAT GGT GAT AAG CAA GAT ATC CAG GGT AAA CTC AAG TAC AGT       805
Asn Asp Asp Gly Asp Lys Gln Asp Ile Gln Gly Lys Leu Lys Tyr Ser
                115                 120                 125

GAC TGG TGT TTT TTT GAA GGT CAT TAT TCT AGT AAA GTA TTC AAA AAC       853
Asp Trp Cys Phe Phe Glu Gly His Tyr Ser Ser Lys Val Phe Lys Asn
            130                 135                 140

TCG ACA TAT TCT CGG TGC AAT TTC TTG TTC GAC AAC TTA TCA GAC TTG       901
Ser Thr Tyr Ser Arg Cys Asn Phe Leu Phe Asp Asn Leu Ser Asp Leu
            145                 150                 155

GAA AAA TGC GCA AAT TTC ATT AAA ACT TGT AAA TTC ATT GAT AAT AAG       949
Glu Lys Cys Ala Asn Phe Ile Lys Thr Cys Lys Phe Ile Asp Asn Lys
160                 165                 170

GAT AAT ATT ACA ATT CCA GAT ATG AAA CTG TCG CCC TAC GTA AAG AAA       997
Asp Asn Ile Thr Ile Pro Asp Met Lys Leu Ser Pro Tyr Val Lys Lys
175                 180                 185                 190

TTC ACT CAA ACA TCA AAA AAG GAT GCC GCG CTA GTA GGA ACA ATT GAA      1045
```

```
Phe Thr Gln Thr Ser Lys Lys Asp Ala Ala Leu Val Gly Thr Ile Glu
            195                 200                 205

GAA GAC GAA ATT TTT AAA ACA TTT ATG AAT TCA ATG AAA CAG CTG AAT      1093
Glu Asp Glu Ile Phe Lys Thr Phe Met Asn Ser Met Lys Gln Leu Asn
            210                 215                 220

GAA AAT GAC GAG TAC TCA TTC CAA GAT TTT AGC GTA TTG AAA TCT TTA      1141
Glu Asn Asp Glu Tyr Ser Phe Gln Asp Phe Ser Val Leu Lys Ser Leu
            225                 230                 235

GAA AAA GAA TTC TCA AAA AGC ATA GAG TTA GAA AAT AAA ATA GCA GAA      1189
Glu Lys Glu Phe Ser Lys Ser Ile Glu Leu Glu Asn Lys Ile Ala Glu
            240                 245                 250

AGA ACA GAA AGG GTG TTA ACA GAG CTG GTT GGA ACT GGT GAT AAG GTC      1237
Arg Thr Glu Arg Val Leu Thr Glu Leu Val Gly Thr Gly Asp Lys Val
255                 260                 265                 270

AAG AAT AAG AAC AAA AAG AAG AAA AAT AAA AAC GCC AAA AAG AAA TTC      1285
Lys Asn Lys Asn Lys Lys Lys Lys Asn Lys Asn Ala Lys Lys Lys Phe
                275                 280                 285

AAA GAA GAG GAA GCA TCC GCT AAG ATA CCA AAG AAA AAA CGG AAC AGA      1333
Lys Glu Glu Glu Ala Ser Ala Lys Ile Pro Lys Lys Lys Arg Asn Arg
                290                 295                 300

GGC AAG AAG AAG CGT GAA AAT CGT GAA AAA AGC ACC ATT TCT AAG ACC      1381
Gly Lys Lys Lys Arg Glu Asn Arg Glu Lys Ser Thr Ile Ser Lys Thr
                305                 310                 315

AAG AAC AGT AAT GTG GTT ATT ATT GAG GAA GCG GGT AAA GAG GTT TTG      1429
Lys Asn Ser Asn Val Val Ile Ile Glu Glu Ala Gly Lys Glu Val Leu
                320                 325                 330

AAA CAA AGG AAG AAG AAA ATG CTT TTG CAA GAG AAG TTA AAA ATA TCA      1477
Lys Gln Arg Lys Lys Lys Met Leu Leu Gln Glu Lys Leu Lys Ile Ser
335                 340                 345                 350

AAC TCC TCT CAG CCT CAG TCA TCA TCC GCT CAA ACC CAG CCG TCG TTC      1525
Asn Ser Ser Gln Pro Gln Ser Ser Ser Ala Gln Thr Gln Pro Ser Phe
                355                 360                 365

CAA CCT AAA GAA AAC CTT TTC GTA CCA CGG GTA AAA ATT TTG CAT CGT      1573
Gln Pro Lys Glu Asn Leu Phe Val Pro Arg Val Lys Ile Leu His Arg
                370                 375                 380

GAT GAT ACC AAG AAG TAGTAAAAGC TCATGGCTTC TTATATATTA TATATGGAAT      1628
Asp Asp Thr Lys Lys
                385

ACATTTATAA TAAAATAATA AGAATTATAT ATTTTATGAT TATATTATTA CATAAAGTAT    1688

TCCCCATTAT AAATTCTGAG TTTCGTATTT AATGATTTTT CAATGAATAT TTAAAATAAT    1748

AAAATATATG AAATGTTCAT ATACAATGAA ATTGTCATGA AGAAAGATGA CTCCAAGTAT    1808

CGTTTATAAA TCGTCGAGAA AAAGATTATG AAGTTGGTTA ACTTTTTAAA AAACGTGCGC    1868

AATGAGCAGG TTACCATAGA ACTAAAAAAC GGTACCACCG TTTGGGGTAC ACTGCAGTCG    1928

GTATCACCAC AAATGAATGC TATCTTAACT GA                                  1960

(2) INFORMATION FOR SEQ ID NO:10:

(i) SEQUENCE CHARACTERISTICS:
        (A) LENGTH: 387 amino acids
        (B) TYPE: amino acid
        (D) TOPOLOGY: linear (ii) MOLECULE TYPE: protein (v) FRAGMENT TYPE: internal (xi) SEQUENCE DESCRIPTION: SEQ ID NO:10:

Met Ser Asn Val Ala Gly Glu Leu Lys Asn Ser Glu Gly Lys Lys Lys
  1                 5                  10                  15
```

-continued

```
Gly Arg Gly Asn Arg Tyr His Asn Lys Asn Arg Gly Lys Ser Lys Asn
             20                  25                  30

Glu Thr Val Asp Pro Lys Lys Asn Glu Asn Lys Val Asn Asn Ala Thr
             35                  40                  45

Asn Ala Thr His Asn Asn Ser Lys Gly Arg Arg Asn Asn Lys Lys Arg
         50                  55                  60

Asn Arg Glu Tyr Tyr Asn Tyr Lys Arg Lys Ala Arg Leu Gly Lys Ser
 65                  70                  75                  80

Thr Glu Asn Glu Gly Phe Lys Leu Val Ile Arg Leu Leu Pro Pro Asn
                 85                  90                  95

Leu Thr Ala Asp Glu Phe Phe Ala Ile Leu Arg Asp Asn Asn Asn Asp
                100                 105                 110

Asp Gly Asp Lys Gln Asp Ile Gln Gly Lys Leu Lys Tyr Ser Asp Trp
            115                 120                 125

Cys Phe Phe Glu Gly His Tyr Ser Ser Lys Val Phe Lys Asn Ser Thr
    130                 135                 140

Tyr Ser Arg Cys Asn Phe Leu Phe Asp Asn Leu Ser Asp Leu Glu Lys
145                 150                 155                 160

Cys Ala Asn Phe Ile Lys Thr Cys Lys Phe Ile Asp Asn Lys Asp Asn
                165                 170                 175

Ile Thr Ile Pro Asp Met Lys Leu Ser Pro Tyr Val Lys Lys Phe Thr
            180                 185                 190

Gln Thr Ser Lys Lys Asp Ala Ala Leu Val Gly Thr Ile Glu Glu Asp
        195                 200                 205

Glu Ile Phe Lys Thr Phe Met Asn Ser Met Lys Gln Leu Asn Glu Asn
    210                 215                 220

Asp Glu Tyr Ser Phe Gln Asp Phe Ser Val Leu Lys Ser Leu Glu Lys
225                 230                 235                 240

Glu Phe Ser Lys Ser Ile Glu Leu Glu Asn Lys Ile Ala Glu Arg Thr
                245                 250                 255

Glu Arg Val Leu Thr Glu Leu Val Gly Thr Gly Asp Lys Val Lys Asn
            260                 265                 270

Lys Asn Lys Lys Lys Asn Lys Asn Ala Lys Lys Phe Lys Glu
        275                 280                 285

Glu Glu Ala Ser Ala Lys Ile Pro Lys Lys Arg Asn Arg Gly Lys
    290                 295                 300

Lys Lys Arg Glu Asn Arg Glu Ser Thr Ile Ser Lys Thr Lys Asn
305                 310                 315                 320

Ser Asn Val Val Ile Ile Glu Glu Ala Gly Lys Glu Val Leu Lys Gln
                325                 330                 335

Arg Lys Lys Lys Met Leu Leu Gln Glu Lys Leu Lys Ile Ser Asn Ser
            340                 345                 350

Ser Gln Pro Gln Ser Ser Ser Ala Gln Thr Gln Pro Ser Phe Gln Pro
        355                 360                 365

Lys Glu Asn Leu Phe Val Pro Arg Val Lys Ile Leu His Arg Asp Asp
    370                 375                 380

Thr Lys Lys
385
```

(2) INFORMATION FOR SEQ ID NO:11:

(i) SEQUENCE CHARACTERISTICS:
        (A) LENGTH: 30 base pairs
        (B) TYPE: nucleic acid

```
        (C) STRANDEDNESS: single
        (D) TOPOLOGY: linear (ii) MOLECULE TYPE: RNA (xi) SEQUENCE DESCRIPTION: SEQ ID NO:11:

AAUGCUUAAA UAAUCUAAUA UUGUAUCUGC                                    30

(2) INFORMATION FOR SEQ ID NO:12:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:12:

UCUGCAUUGA UAAUAUCAUU GGACAGAAAU U                                  31

(2) INFORMATION FOR SEQ ID NO:13:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:13:

GGCGGCUCGG CACUGUUACC UCUCGGUCCG                                    30

(2) INFORMATION FOR SEQ ID NO:14:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:14:

AACCGGCCCG AGGGCCCUAC CCGGAGGCAC C                                  31

(2) INFORMATION FOR SEQ ID NO:15:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: RNA (xi) SEQUENCE DESCRIPTION: SEQ ID NO:15:

AGGAUGGACG                                                          10

(2) INFORMATION FOR SEQ ID NO:16:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: RNA
```

-continued

```
       (xi) SEQUENCE DESCRIPTION: SEQ ID NO:16:

CUUGGAAUGG CGAAGAA                                                          17

(2) INFORMATION FOR SEQ ID NO:17:

(i) SEQUENCE CHARACTERISTICS:
           (A) LENGTH: 11 base pairs
           (B) TYPE: nucleic acid
           (C) STRANDEDNESS: single
           (D) TOPOLOGY: linear (ii) MOLECULE TYPE: RNA (xi) SEQUENCE DESCRIPTION: SEQ ID NO:17:

CUUUUGAGAA C                                                                11

(2) INFORMATION FOR SEQ ID NO:18:

(i) SEQUENCE CHARACTERISTICS:
           (A) LENGTH: 12 base pairs
           (B) TYPE: nucleic acid
           (C) STRANDEDNESS: single
           (D) TOPOLOGY: linear (ii) MOLECULE TYPE: RNA (xi) SEQUENCE DESCRIPTION: SEQ ID NO:18:

AUAUUUGGAC AA                                                               12
```

HETEROLOGOUS POLYPEPTIDE PRODUCTION IN THE ABSENCE OF NONSENSE-MEDIATED MRNA DECAY FUNCTIONS

This application is a Continuation-in-Part of U.S. Ser. No. 08/955,472 filed on Oct. 21, 1997, now abandoned, which is a Continuation-in-Part of of U.S. Ser. No. 08/375,300 filed on Jan. 20, 1995, U.S. Pat. No. 5,679,566 which are both incorporated herein by reference in their entirety.

STATEMENT AS TO FEDERALLY SPONSORED RESEARCH

This invention was made at least in part with funds from the Federal government under NIH grant number GM27757, and the government therefore may have certain rights in the invention.

BACKGROUND OF THE INVENTION

The invention relates to nonsense-mediated mRNA decay function.

It is well known in the field of biology that changes in the amino acid sequence of a protein can result in changes in the biological function of the protein. To optimize a target biological function, the amino acid sequence can be altered and tested for improved function. In very simple terms, this is the process of evolution by which the proteins that exist naturally today have been selected over eons. It is an advantage of modern molecular biology that such alterations can be made in a matter of days rather than a matter of centuries. Specifically, optimizing the biological function of a protein of pharmaceutical or other commercial interest can be performed by substituting one amino acid for the naturally occurring amino acid at a given site and producing a sufficient quantity of the protein for screening of biological activity.

Production of a recombinant protein in a cellular system requires the efficient translation of the mRNA transcript encoding the protein. For this to occur, the transcript must exist in the cell long enough for translation into the desired recombinant protein. mRNA transcripts vary in the length of time (transcript half-life) that they exist in a cell prior to being degraded by cellular proteins specific for that purpose. In some cases, degradation occurs rapidly such that very little protein is produced.

For example, the yeast cell, *Saccharomyces cerevisiae*, a commonly used cellular system for the production of recombinant proteins, has a biological pathway that specifically degrades mRNA transcripts containing a non-coding triplet sequence (nonsense or stop codons) in the transcript. In several genes studied thus far, the destabilizing nonsense codon occurs within the 5'-proximal portion of the transcript (reviewed in Peltz et al., Prog. Nucl. Acids Res. Mol. Biol. (1994) 47:271–297). The translation process stops at the nonsense codons prior to reaching the end of the transcript's coding sequence resulting in the production of a truncated protein that may not possess normal biological activity. Thus, the cell has developed a biochemical system to degrade transcripts containing mutations that create stop codons early in the coding sequence.

However, in a cell of a suppressor strain that suppresses nonsense codons, a nonsense codon can be a useful means of coding for an alternate amino acid when a nonsense codon is engineered into the coding sequence to produce an altered protein which is then screened for enhanced biological activity. Suppressor strains (e.g., SUF1-1) do not allow maximal expression of a nonsense codon-containing transcript (Leeds et al., (1991) Genes & Dev. 5:2303–2314).

Nonsense-mediated mRNA decay is a phenomenon in which nonsense mutations, e.g., point or frame shift mutations that create a stop codon in the reading frame, in a gene can enhance the decay rate of the mRNA transcribed from that gene. For a review, see, e.g., Peltz et al., (1994) Prog. Nuc. Acid Res. Mol. Biol. 47:271–297. The process occurs in viruses, prokaryotes, and eukaryotes (Leeds (1991), supra; Barker, G. F. and Beemon, K. (1991) Mol. Cell. Biol. 11:2760–2768; Lim, S.-K. and Maquat, L. E. (1992) EMBO J. 11:3271–3278).

In most genetic systems, 61 of the 64 possible codon triplets encode amino acids. The triplets UAA, UAG, and UGA are non-coding (nonsense codons) and promote translational termination (Osawa et al., (1992) Microbiol. Rev. 56:229–264). The polypeptide chain terminating effects of UAA, UAG, and UGA triplets have been amply documented and characterized (Craigen et al., (1990) Mol. Microbiol. 4:861–865).

Nonsense-mediated mRNA decay has been studied extensively in the yeast *Saccharomyces cerevisiae* where it has been shown that degradation of mRNA via this pathway is most likely to occur in the cytoplasm and is linked to translation. Evidence in support of these conclusions includes the following: 1) unstable, nonsense-containing mRNAs are stabilized in a strain harboring an amber suppressor tRNA (Losson and Lacroute, (1979) Proc. Nat'l. Acad. Sci. USA 76:5134–5137; Gozalbo and Hohmann, (1990) Curr. Genet. 17:77–79); 2) nonsense-containing mRNAs are ribosome-associated (Leeds et al., (1991) Genes & Dev. 5:2303–2314; He et al., (1993) Proc. Nat'l. Acad. Sci. USA 90:7034–7039) and the number of ribosomes associated with such mRNAs is a function of the relative positions of the respective nonsense codons (He et al., (1993) Proc. Nat'l. Acad. Sci. USA 90:7034–7039); and 3) treatment of cells with cycloheximide, an inhibitor of translational elongation, stabilizes nonsense-containing mRNAs, yet removal of cycloheximide leads to the immediate restoration of rapid mRNA decay (Peltz et al., (1997) RNA 3:234–244).

Previous studies of nonsense-mediated mRNA decay in yeast also have shown that the products of the UPF1 and UPF3 genes (proteins Upf1p and Upf3p, respectively) are essential components of this degradative pathway. Mutations in these genes stabilize mRNAs containing premature nonsense codons without affecting the decay rates of most wild-type transcripts (Leeds et al., (1991) Genes & Dev. 5:2303–2314, Leeds et al., (1992) Mol. Cell. Biol. 12:2165–2177; Peltz et al., (1993) Genes & Dev. 7:1737–1754; He et al., (1993) Proc. Nat'l. Acad. Sci. USA 90:7034:7039; Cui et al., (1995) Genes & Dev. 9:423–436; He and Jacobson, (1995) Genes & Dev. 9:437–454; He et al., (1997) Mol. Cell. Biol. 17:1580–1594; Lee and Culbertson, (1995) Proc. Nat'l. Acad. Sci. USA 92:10354–10358; Lee and Varmus, (1995) Proc. Nat'l. Acad. Sci. USA 92:6587–6591).

The UPF1 gene has been cloned and sequenced, (Leeds et al., (1992) Mol. Cell Biol. 12:2165–2177) and shown to be: 1) non-essential for viability; 2) capable of encoding a 109 kD protein with a so-called zinc finger, nucleotide (GTP) binding site, and RNA helicase motifs (Leeds et al., (1992) Mol. Cell. Biol. 12:2165–2177; Altamura et al., (1992) J. Mol. Biol. 224:575–587; Koonin, (1992) Trends Biochem. Sci. 17:495–497); 3) identical to NAM7, a nuclear gene that was isolated as a high copy suppressor of mitochondrial RNA splicing mutations (Altamura et al., (1992) J. Mol. Biol. 224:575–587); and 4) partially homologous to the yeast SEN1 gene (Leeds et al., (1992) Mol. Cell. Biol. 12:2165–2177). The latter encodes a noncatalytic subunit of the tRNA splicing endonuclease complex (Winey and Culbertson, (1988) Genetics 118:607–617; DeMarin et al., (1992) Mol. Cell. Biol. 12:2154–2164), suggesting that the Upf1p protein (Upf1p) may also be part of a nuclease complex targeted specifically to nonsense-containing mRNAs.

Suppression of nonsense-mediated mRNA decay in upf1 deletion strains does not appear to result simply from enhanced read-through of the termination signal (Leeds et al., (1991) Genes & Dev. 5:2303–2314), nor does it appear to be specific for a single nonsense codon. The ability of upf1⁻ mutants to suppress tyr7-1 (UAG), leu2-1 (UAA), leu2-2 (UGA), met8-1 (UAG), and his4–166 (UGA) (Leeds et al., (1992) Mol. Cell. Biol. 12:2165–2177) indicates that they can act as omnipotent suppressors. upf1⁻ mutants degrade nonsense-containing transcripts at a slower rate allowing synthesis of sufficient read-through protein to permit cells to grow under nutrient-deficient conditions that are nonpermissive for UPF1⁺ cells.

SUMMARY OF THE INVENTION

The invention relates to the discovery of a gene, NMD2, named after its role in the Nonsense-Mediated mRNA Decay pathway, and the protein, Nmd2p, encoded by the NMD2 gene. Nmd2p is shown herein to bind to Upf1p. A C-terminal fragment of the protein is also shown to bind to Upf1p and, when overexpressed in the host cell, the fragment inhibits the function of Upf1p, thereby inhibiting the nonsense-mediated mRNA decay pathway. The components of the nonsense-mediated mRNA decay pathway monitor the fidelity of translation, terminating translation and accelerating decay when a premature nonsense codon-containing mRNA is detected. Interference with the components thus alters both the decay process and the fidelity process. Inhibition of the nonsense-mediated mRNA decay pathway is a useful means of treating disorders caused by the presence of nonsense mutations.

The invention further relates to the inhibition of the nonsense-mediated mRNA pathway to produce a heterologous recombinant protein or polypeptide in a host cell or to increase the production of an endogenous protein useful to a host cell or organism. A codon of the gene encoding the recombinant protein is mutated to encode a nonsense codon. Expression of this recombinant protein is enhanced by stabilizing the nonsense codon-containing mRNA transcript in a host cell in which the nonsense-mediated mRNA decay pathway is inhibited.

The insertion of a nonsense codon into the gene of interest is useful to produce an altered heterologous protein by amino acid substitution at the nonsense codon in a suppressor host strain. Insertion of a nonsense codon further allows the controlled expression of a protein that may be toxic to the cell by controlling the timing of nonsense-mediated mRNA decay pathway inhibition. Insertion of a nonsense codon also allows the production of an N-terminal fragment of a heterologous protein in increased yield when the nonsense codon-containing transcript is expressed in a host strain that is not a suppressor of nonsense codons.

The invention further provides methods of increasing expression of nonsense codon-containing transcripts by inhibiting the nonsense-mediated mRNA decay pathway by overexpressing the C-terminal fragment of Nmd2p in the same cell that is also expressing the heterologous protein. Overexpression of the C-terminus of Nmd2p is not deleterious to the cell since its expression provides specific stabilization of transcripts having a stop codon early in the transcript and does not affect the stability of other transcripts.

The invention features a method of substantially inhibiting the nonsense-mediated mRNA decay pathway by providing a cell (such as a yeast cell) and mutating the MD2 gene such that essentially no functional Nmd2p is produced. For example, an insertional mutation which prevents synthesis of the Nmd2p results in an inhibited nonsense-mediated mRNA decay pathway without affecting the viability of the cell as described herein.

The invention also features a method of substantially inhibiting the nonsense-mediated mRNA decay pathway by providing a cell (such as a yeast cell) and mutating the UPF1 gene such that essentially no functional Upf1p is produced. For example, an insertional mutation which prevents synthesis of the Upf1p results in an inhibited nonsense-mediated mRNA decay pathway without affecting the viability of the cell as described herein.

In addition, the invention features a method of inhibiting the nonsense-mediated mRNA decay pathway by providing a cell and transforming the cell with a vector encoding NMD2 operably linked to regulatory sequences for constitutive or inducible expression of the antisense transcript. Such an antisense transcript hybridizes to essentially all of the NMD2 sense transcript preventing translation and the production of functional Nmd2p, thereby inhibiting the nonsense-mediated mRNA decay pathway. By "hybridizing to essentially all of the sense NMD2 transcript" is meant that a sufficient amount of the sense transcript is bound by antisense transcript to inhibit translation such that substantially no functional Nmd2p protein is produced.

The invention features a method of inhibiting the nonsense-mediated mRNA decay pathway by providing a cell and transforming the cell with a vector encoding UPF1 operably linked to regulatory sequences for constitutive or inducible expression of the antisense transcript. Such antisense transcript hybridizes to a sufficient portion of the UPF1 sense transcript to prevent translation production of functional Upf1p, thereby inhibiting the nonsense mediated mRNA decay pathway.

The invention also features a substantially pure DNA of the NMD2 gene, and degenerate variants thereof, involved in the nonsense-mediated mRNA pathway of a cell. The DNA of the invention is at least 90% identical to SEQ ID NO:1, and is preferably from the yeast *Saccharomyces cerevisiae*. The DNA encodes an amino acid sequence of Nmd2p (SEQ ID NO:2). The amino acid sequence of the invention is at least 90% identical to the amino acid sequence of SEQ ID NO:2.

The invention also features the substantially pure DNA sequence of the 3' terminus (SEQ ID NO:3) of NMD2. The 3' terminus encodes the carboxy terminal fragment (SEQ ID NO:4) of Nmd2p, which fragment, when overexpressed in a yeast cell, binds to Upf1p and inhibits the nonsense-mediated mRNA decay pathway.

In addition, the invention features a vector containing a DNA sequence (SEQ ID NO:1) encoding a polypeptide (SEQ ID NO:2). Preferably the coding sequence is under the transcriptional control of regulatory sequences that are activated and deactivated by an externally applied condition such as temperature, or an externally supplied chemical agent. Such control expression systems are well known to those of ordinary skill in the art. Thus, the expression of the DNA is turned on and off as necessary for the controlled (i.e., conditional) inhibition of the nonsense-mediated mRNA pathway.

The invention further features a vector containing a DNA sequence (SEQ ID NO:3) encoding a polypeptide (SEQ ID NO:4) which polypeptide, when overexpressed in a cell, inhibits the nonsense-mediated mRNA decay pathway. Preferably the coding sequence is under the transcriptional control of regulatory sequences that are activated and deactivated by an externally applied condition such as temperature or an externally supplied chemical agent. Thus, the expression of the DNA is turned on and off as necessary for the controlled (i.e., conditional) inhibition of the nonsense-mediated mRNA decay pathway.

The invention also features a host cell containing the DNA of SEQ ID NO:1 or SEQ ID NO:3 or fragments thereof. The invention also features cells harboring vectors containing the DNA of SEQ ID NO:1 or SEQ ID NO:3 or fragments thereof.

In another embodiment, the invention features substantially pure nonsense-mediated mRNA decay pathway protein, Nmd2p (SEQ ID NO:2), and fragments thereof from a yeast cell, preferably from the genus Saccharomyces.

The invention also features a substantially pure nonsense-mediated mRNA decay pathway protein Nmd2p C-terminal fragment (SEQ ID NO:4) and fragments thereof which bind to the nonsense-mediated mRNA decay pathway protein, Upf1p, and which when overexpressed in a cell, substantially inhibit the nonsense-mediated mRNA decay pathway in the cell.

The invention further features a cell containing a vector expressing a polypeptide containing the Nmd2p carboxy terminal fragment (SEQ ID NO:4), which fragment binds to the nonsense-mediated mRNA decay pathway protein, Upf1p, and, when overexpressed in the cell, substantially inhibits the nonsense-mediated mRNA decay pathway in the cell.

In addition, the invention features methods of producing a heterologous polypeptide from an mRNA transcript in which the transcript contains at least one nonsense codon within a transcript destabilizing 5' portion. The method involves providing a cell in which the nonsense-mediated mRNA decay pathway is substantially inhibited by 1) overexpression of a polypeptide containing the Nmd2p carboxy terminal fragment (SEQ ID NO:4); or 2) mutation of NMD2 or UPF1 (e.g., insertional mutagenesis) resulting in inhibition of the nonsense-mediated mRNA decay pathway of the cell; or 3) expression of NMD2 or UPF1 antisense mRNA which hybridizes to the sense transcript of NMD2 or UPF1, respectively, inhibiting translation and, thereby inhibiting the nonsense-mediated mRNA decay pathway. Expression in this cell of a nonsense codon-containing gene encoding the heterologous polypeptide provides a transcript whose stability is enhanced at least two-fold compared to a wild-type cell. Translation of the transcript produces the heterologous polypeptide.

In another embodiment, the invention features antibodies that are raised against and bind specifically to Nmd2p, a protein having the amino acid sequence of SEQ ID NO:2, or a polypeptide having the amino acid sequence of SEQ ID NO:4. The antibodies can be polyclonal or monoclonal.

The invention further features a method of screening a candidate host cell for the presence or absence of 1) Nmd2p, 2) a C-terminal fragment of Nmd2p, 3) a polypeptide of SEQ ID NO:2, or 4) a polypeptide of SEQ ID NO:4, including fragments or analogs thereof. The method also can be used to determine relative amounts of each of the proteins in a cell. The screening method is useful for isolating a host strain in which heterologous protein production is to be optimized. The method first involves lysis of a clonal population of cells suspected of containing Nmd2p or Nmd2p fragment. Antibody to Nmd2p or Nmd2p fragment is contacted with proteins of the lysate. Presence, relative abundance, or absence of Nmd2p or Nmd2p fragment in the lysate is determined by the binding of the antibody. Possible detection methods include affinity chromatography, Western blotting, or other techniques well known to those of ordinary skill in the art.

A heterologous polypeptide produced by the methods of the invention can be a particular fragment of a protein or polypeptide. A nonsense codon is incorporated into the DNA sequence encoding the protein or polypeptide at a position within a transcript destabilizing 5' portion of the sequence at a desired transcriptional stop site. Expression of the DNA in a cell having an inhibited nonsense-mediated mRNA decay pathway results in a substantially increased half-life for the nonsense codon-containing transcript. An advantage of this method is the stabilization of the transcript allowing an increased amount of the protein fragment to be produced relative to the amount produced in a wild-type host strain.

A heterologous protein that is normally toxic to a cell is produced by controllably inhibiting the nonsense-mediated mRNA decay pathway and thereby, controlling the stability of a nonsense codon-containing transcript for the toxic protein. Inhibition of the nonsense-mediated mRNA decay pathway is accomplished, for example, by the inducible expression of the C-terminus of the Nmd2p only when protein production is desired (e.g., at optimal cell density of the culture). Inhibition of the nonsense-mediated mRNA decay pathway substantially increases the half-life of the transcript containing a nonsense codon in a transcript destabilizing 5' portion of the transcript thereby increasing translation and production of the protein when desired. The cell expressing the heterologous protein can be a nonsense suppressor cell in which the suppressor mechanism is controllably expressed and substitutes the naturally occurring amino acid at the site of a nonsense codon.

An altered heterologous polypeptide is produced in a nonsense suppressor cell by substituting an amino acid at the position of a nonsense codon, which amino acid does not naturally occur at that position. An amino acid is substituted which alters a target biological activity of the protein in the cell. The nonsense-mediated mRNA pathway is inhibited to increase production of the altered heterologous polypeptide from a transcript containing a nonsense codon in a transcript destabilizing 5' portion of the transcript.

Alteration in biological activity includes increased binding affinity to a target molecule such as a receptor, antibody, or decreased toxicity of the protein to the host strain in which the protein is produced. By "substantial reduction in toxicity" is meant that expression of the altered heterologous polypeptide allows the cell growth rate to be at least two-fold greater than the growth rate in the presence of the natural toxic heterologous polypeptide, or allows sufficient cell growth for production of the altered heterologous protein.

An advantage of the invention is the ability to increase heterologous protein production and direct amino acid substitution to a desired codon position using a nonsense codon and producing the protein in a suppressor mutant such that a known amino acid is substituted in each suppressor host.

Stabilization of the mRNA transcript by inhibiting the nonsense-mediated mRNA decay pathway increases the half-life of the transcript (decreases its decay rate) thereby allowing increased translation from the transcript. Preferably the nonsense codon is present in a transcript destabilizing 5' portion of the transcript. Preferably the transcript containing the nonsense codon decays rapidly in the presence of an unaltered wild-type nonsense-mediated mRNA decay pathway, and decays at least two-fold more slowly in the presence of a nonsense-mediated mRNA decay pathway inhibited by the method of the invention.

The invention also includes a substantially pure polypeptide that specifically binds to the Upf1p protein, wherein the binding causes inhibition of the nonsense mediated mRNA decay pathway.

In another embodiment, the invention features substantially pure nucleic acids (and vectors containing them) which hybridize under stringent conditions to the nucleotide sequence of SEQ ID NO:1 or SEQ ID NO:3 or their complementary sequences, wherein the nucleic acid encode an Nmd2p polypeptide or a carboxy terminal fragment of an Nmd2p polypeptide that inhibits the nonsense-mediated mRNA decay pathway in a cell, respectively.

In yet another aspect, the invention features a method of determining whether a candidate compound, e.g., a small molecule or nucleic acid, modulates the nonsense-mediated mRNA decay pathway by a) obtaining a cell (e.g., from a mammal such as a human) containing a mutation in a specific nonsense mutation-containing gene; b) incubating the cell with the candidate compound under conditions and for a time sufficient for the cell to express nonsense-mediated mRNA decay pathway genes in the absence of the candidate compound; and c) measuring expression (e.g., RNA or protein) of the nonsense mutation-containing gene, or activity of the gene product in the presence and in the absence of the candidate compound, wherein a difference in expression or activity indicates that the compound modulates nonsense-mediated mRNA decay. The cell can be, for example, a yeast cell containing a nonsense mutation in a gene such that the ability of the cell to grow in a selective medium depends on the functionality of the nonsense-mediated decay pathway. Further, the gene containing the nonsense mutation can be selected from the group consisting of tyr7, leu2, and CAN1, and the the nonsense-mediated decay pathway gene can be NMD2, UPF1, UPF3, RENT1, HUPF1, or homologs thereof.

In another aspect, the invention features a method for treating a mammal, e.g., a human, having a disorder involving a nonsense mutation by administering to the mammal a therapeutically effective amount of a compound that inhibits the nonsense-mediated mRNA decay pathway. For example, the compound can cause decreased expression of UPF1, UPF3, NMD2, RENT1, HUPF1, or their homologs, or decreased activity of Upf1p, Upf3p, or Nmd2p or their homologs. The compound can be the C-terminal fragment of Nmd2p or an antisense oligonucleotide. The disorder can be breast cancer, polycystic kidney disease I, polycystic kidney disease II, Niemann-Pick disease, adenomatous polyposis coli, cystic fibrosis, Fanconi's anemia, hemophilia, hypercholesterolemia, neurofibromatosis, ornithine tranScarbamylase deficiency, retinoblastoma, glycogen storage disease, McArdle disease, cancer, Tay-Sachs disease, Cowden disease, Wilson disease, or β-thalassaemia.

The invention also features method for treating a patient with a disorder associated with excessive expression or activity of an NMD2 gene, the method involving administering to the patient a compound which inhibits expression of NMD2.

A "substantially pure DNA" is a DNA that is not immediately contiguous with (i.e., covalently linked to) both of the coding sequences with which it is immediately contiguous (i.e., one at the 5' end and one at the 3' end) in the naturally-occurring genome of the organism from which the DNA of the invention is derived. The term therefore includes, for example, a recombinant DNA which is incorporated into a vector, into an autonomously replicating plasmid or virus, or into the genomic DNA of a prokaryote or eukaryote; or which exists as a separate molecule (e.g., a cDNA or a genomic or cDNA fragment produced by PCR (polymerase chain reaction) or restriction endonuclease digestion) independent of other sequences. It also includes a recombinant DNA which is part of a hybrid gene encoding additional polypeptide sequences.

A "polypeptide" is any chain of amino acids, regardless of length or post-translational modification (e.g., glycosylation).

By "inhibited nonsense-mediated mRNA decay pathway" is meant decreased turnover of a nonsense codon-containing mRNA transcript in which the half-life of the nonsense codon-containing mRNA is at least two-fold greater in a nonsense-mediated mRNA decay pathway altered by the methods of the invention relative to its half-life in a wild type cell. Techniques for measuring mRNA half-life are described herein and in Parker et al. (1991) Meth. Enzymol. 194:415–423. The pathway can also be inhibited by increased read-through of nonsense codon-containing mRNAs.

A "transcript destabilizing 5' portion" is a 5' proximal region of an mRNA transcript in which region the presence of a nonsense codon results in an increased rate of transcript degradation by at least two-fold compared to the normal transcript in a wild-type organism. Determination of a transcript destabilizing 5' portion is readily performed by one of ordinary skill in the art. The half-life of the transcript from each altered DNA is compared to the wild-type transcript by standard techniques. An approximately two-fold or more decrease in half-life for the altered transcript in a cell expressing wild-type nonsense-mediated mRNA decay pathway activity indicates that the nonsense codon is in a transcript destabilizing region. The region 5' proximal of the most downstream destabilizing nonsense codon position is considered a transcript destabilizing 5' portion.

"Nmd2p" is the protein encoded by a gene, NMD2, which is involved in the nonsense-mediated mRNA decay pathway (e.g., SEQ ID NO:1 depicts the NMD2 gene of *Saccharomyces cerevisiae* which encodes the Nmd2p depicted in SEQ ID NO:2).

"Upf1p" is the protein encoded by a gene, UPF1, which is involved in the nonsense-mediated mRNA decay pathway (e.g., FIGS. 5A and 5B (SEQ ID NO:7) depicts a UPF1 nucleic acid sequence of *Saccharomyces cerevisiae* which encodes the Upf1p depicted in FIG. 6 (SEQ ID NO:8); GenBank Accession No. M76659; Leeds et al. (1992), supra).

"Upf3p" is the protein encoded by a gene, UPF3, which is involved in the nonsense-mediated mRNA decay pathway (e.g., FIG. 7 (SEQ ID NO:9) depicts a UPF3 nucleic acid sequence of *Saccharomyces cerevisiae* which encodes the Upf3p depicted in FIG. 8 (SEQ ID NO:10); GenBank Accession No. L41153; Lee and Culbertson (1995), supra).

A "substantially pure polypeptide" is a polypeptide, e.g., a nonsense-mediated mRNA decay pathway polypeptide or fragment thereof, that is at least 60%, by weight, free from the proteins and naturally-occurring organic molecules with which it is naturally associated. Preferably, the preparation is at least 75%, more preferably at least 90%, and most preferably at least 99%, by weight, nonsense-mediated mRNA decay pathway polypeptide or fragment. A substantially pure nonsense-mediated mRNA decay pathway polypeptide or fragment thereof is obtained, for example, by extraction from a natural source; by expression of a recombinant nucleic acid encoding a nonsense-mediated mRNA decay pathway polypeptide or fragment thereof; or by chemically synthesizing the polypeptide or fragment. Purity can be measured by any appropriate method, e.g., column chromatography, polyacrylamide gel electrophoresis, or HPLC analysis.

A "carboxy terminal fragment of Nmd2p" is the sequence including amino acid 326 to amino acid 1089 (SEQ ID NO:4) or a fragment thereof. The carboxyl terminus is any polypeptide including SEQ ID NO:4 or a fragment thereof that substantially inhibits nonsense-mediated mRNA decay in a cell when the fragment is expressed above endogenous level, as described herein.

By "substantially inhibit nonsense-mediated mRNA decay" is meant to cause an increase by at least two-fold in the half-life of an mRNA of interest in the presence of an inhibiting agent (e.g., a chemical agent, a polypeptide fragment, or like substance) that interferes with the functioning of the proteins of the nonsense-mediated mRNA pathway.

An "overexpressed polypeptide" is a polypeptide which, when produced by the in vivo expression of a DNA sequence to produce that polypeptide, is produced in a quantity at least two-fold greater than the quantity of the same polypeptide expressed from the endogenous transcription/translation regulatory elements of the DNA sequence of interest. In the case of the expression of a gene fragment, the endogenous regulatory elements are those of the native gene.

By "substantially increased transcript stability" is meant an increase in the half-life of an mRNA transcript by at least two-fold in the presence of an inhibited nonsense-mediated mRNA decay pathway. The half-life of an mRNA transcript can be measured by extracting at various time points total mRNA from a cell expressing the gene of interest. This is followed by determining the abundance of a transcript over time by Northern analysis using a labelled (e.g., radiolabelled probe) nucleic acid probe to visualize the transcript. Increased transcript stability can also be inferred from increased expression of a polypeptide from the gene of interest in the presence of an inhibited nonsense-mediated mRNA pathway.

By "essentially no functional protein produced" is meant that a particular protein (e.g., Nmd2p or Upf1p) is present in a cell in such low amounts that the nonsense-mediated mRNA decay pathway is inhibited, resulting in at least a two-fold increase in the stability of mRNA transcripts containing a nonsense codon in a transcript destabilizing 5' portion.

By "operably linked" is meant that a gene and a regulatory sequence(s) are connected in such a way as to permit gene expression when the appropriate molecules (e.g., transcriptional activator proteins) are bound to the regulatory sequencers).

"Inducible regulatory sequences" are regulatory sequences (e.g., transcriptional regulatory sequences) whose function is initiated by the introduction of one or more external agents to the cell culture medium and whose function is inhibited by the removal of the external agents.

By "specifically binds" is meant a molecule that binds to a particular entity, e.g., an Nmd2p polypeptide, but which does not substantially recognize or bind to other molecules in a sample, e.g., a biological sample, which includes the particular entity, e.g., Nmd2p.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference. In addition, the materials, methods, and examples are illustrative only and not intended to be limiting.

Other features and advantages of the invention will be apparent from the detailed description, and from the claims.

DESCRIPTION OF THE DRAWINGS

FIGS. 1A to 1C are a representation of the DNA sequence (SEQ ID NO:1) and the deduced amino acid sequence (SEQ ID NO:2) of NMD2. Cloning of the NMD2 gene and determination of its DNA sequence are described herein. The predicted amino acid sequence is indicated in single-letter code and shown below each line of DNA sequence. Position number 1 corresponds to the A of the ATG initiation codon. The NMD2 open reading frame is interrupted by an intron of 113 nucleotides in which the conserved 5' splice site [GUAUGU], branchpoint [UACUAAC], and 3' splice site [AG] are underlined. Transcription initiation sites at nucleotides −56, −60, −64, and −67 (relative to the initiator ATG) were determined by primer extension analysis and are indicated by vertical arrows. The putative TATA box and Abf1p binding consensus sequence, located between positions −219 to −213 and −198 to −186 in the NMD2 promoter region are respectively underlined by dashed lines. Double underlined residues fit the consensus for a bipartite nuclear localization signal (Dingwall and Laskey, (1991) Trends Biochem. Sci. 16:478–481). The positions where FLAG-or MYC-epitope tag sequences were inserted are indicated by lollipops and the position where the original GAL4-NMD2 fusion begins is indicated by an arrow with a right angle stem. The bent arrow also indicates the start of the DNA sequence from nucleotide 1089 to nucleotide 3383 (SEQ ID NO:3) encoding the carboxyl terminal amino acid sequence from amino acid 326 to amino acid 1089 (SEQ ID NO:4) of Nmd2p, a peptide fragment which, when overexpressed, binds to Upf1p and inhibits the nonsense-mediated mRNA decay pathway.

FIGS. 2A to 2C are diagrams illustrating insertion and deletion experiments performed to assess the active regions of NMD2 gene. DNA fragments associated with NMD2 function are indicated. FIG. 2A is a restriction map of the nmd2::HIS3 allele. FIG. 2B is a restriction map of the NMD2 gene. FIG. 2C is a diagram of the results of a complementation analysis to determine functional portions of Nmd2p.

FIG. 3A is reproduced from a Southern analysis of wild type and HIS3-disrupted NMD2 associated with NMD2 gene disruption. FIG. 3B is reproduced from a Northern analysis of the stability of different nonsense-containing PGK1 alleles in NMD2 and nmd2::HIS3 haploid yeast strains. FIG. 3C is reproduced from a Northern analysis of CYH2 pre-mRNA and mRNA transcript stability.

FIGS. 5A and 5B are a representation of the nucleic acid sequence of UPF1 (SEQ ID NO:7).

FIG. 6 is a representation of the deduced amino acid sequence of Upf1p (SEQ ID NO:8).

FIG. 7 is a representation of the nucleic acid sequence of UPF3 (SEQ ID NO:9).

FIG. 8 is a representation of the deduced amino acid sequence of Upf3p (SEQ ID NO:10).

DETAILED DESCRIPTION

Figure 3A:
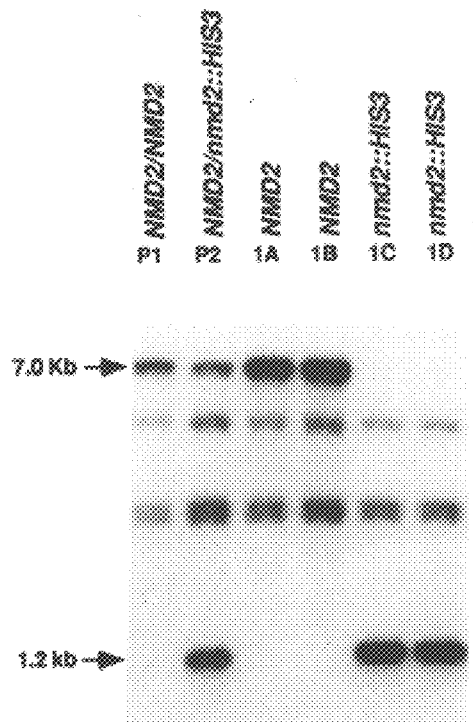
FIGS. 3A to 3C are representations of autoradiograms.

This invention relates to a DNA sequence, a protein, and methods useful in inhibiting the nonsense-mediated mRNA decay pathway in a cell, preferably in a yeast cell or a human cell, e.g., by stabilizing an mRNA transcript which contains a nonsense codon. Preferably, the nonsense codon is in a transcript destabilizing 5' portion of the transcript. Stabilization of the transcript allows increased translation and increased production of a heterologous protein of interest. The protein of interest can be a full-length protein if the nonsense codon is suppressed. The protein of interest can be a desired N-terminal fragment of a protein if the nonsense codon is not suppressed.

Inhibition of the decay of transcripts from the nonsense mutation-containing gene can ameliorate the effects of disorders caused by the presence of a nonsense codon. This can be accomplished by inhibiting a component of the nonsense-mediated decay pathway (e.g., Nmd2p, Upf1p, or Upf3p) with, for example, compounds that bind to Nmd2p, compounds that interfere with the interaction between NMD2 and other molecules in the nonsense-mediated RNA decay pathway (e.g., Upf1p or Upf3p), or compounds that inhibit the expression of nonsense-mediated mRNA decay pathway genes. Antisense therapy or ribozyme therapy are other methods of inhibiting the expression of components of the nonsense mediated decay pathway.

Antisense Constructs and Therapies

Treatment regimes based on an "antisense" approach involve the design of oligonucleotides (either DNA or RNA) that are complementary to nonsense-mediated mRNA decay pathway mRNAs (e.g., transcripts from NMD2 or UPF1). These oligonucleotides bind to the complementary mRNA transcripts and prevent translation. Absolute complementarity, although preferred, is not required. A sequence "complementary" to a portion of an RNA, as referred to herein, is a sequence sufficiently complementary to be able to hybridize with the RNA, forming a stable duplex, within the environment of a cell; in the case of double-stranded antisense nucleic acids, a single strand of the duplex DNA may be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

The invention also encompasses nucleic acid molecules (DNA and RNA) that hybridize under stringent conditions to a nucleic acid molecule encoding a nonsense-mediated decay pathway polypeptide. The cDNA sequences described herein can be used to identify these nucleic acids, which include, for example, nucleic acids that encode homologous polypeptides in other species, and splice variants of nonsense-mediated decay pathway genes (e.g., an NMD2) in humans or other mammals. Accordingly, the invention features methods of detecting and isolating these nucleic acid molecules. Using these methods, a sample (for example, a nucleic acid library, such as a cDNA or genomic library) is contacted (or "screened") with an NMD2-specific probe (for example, a fragment of SEQ ID NO:1 that is at least 25 or 50 nucleotides long). The probe will selectively hybridize to nucleic acids encoding related polypeptides (or to complementary sequences thereof). The term "selectively hybridize" is used to refer to an event in which a probe binds to nucleic acids encoding a nonsense-mediated mRNA decay pathway gene such as NMD2 (or to complementary sequences thereof) to a detectably greater extent than to nucleic acids encoding other proteins (or to complementary sequences thereof). The probe, which can contain at least 25 (for example, 25, 50, 100, or 200 nucleotides) can be produced using any of several standard methods (see, for example, Ausubel et al., "Current Protocols in Molecular Biology, Vol. I," Green Publishing Associates, Inc., and John Wiley & Sons, Inc., NY, 1989). For example, the probe can be generated using PCR amplification methods in which oligonucleotide primers are used to amplify an NMD2-specific nucleic acid sequence (for example, a nucleic acid encoding the chemokine-like domain) that can be used as a probe to screen a nucleic acid library and thereby detect nucleic acid molecules (within the library) that hybridize to the probe.

One single-stranded nucleic acid is said to hybridize to another if a duplex forms between them. This occurs when one nucleic acid contains a sequence that is the reverse and complement of the other (this same arrangement gives rise to the natural interaction between the sense and antisense strands of DNA in the genome and underlies the configuration of the "double helix"). Complete complementarity between the hybridizing regions is not required in order for a duplex to form; it is only necessary that the number of paired bases is sufficient to maintain the duplex under the hybridization conditions used.

Typically, hybridization conditions are of low to moderate stringency. These conditions favor specific interactions between completely complementary sequences, but allow some non-specific interaction between less than perfectly matched sequences to occur as well. After hybridization, the nucleic acids can be "washed" under moderate or high conditions of stringency to dissociate duplexes that are bound together by some non-specific interaction (the nucleic acids that form these duplexes are thus not completely complementary).

As is known in the art, the optimal conditions for washing are determined empirically, often by gradually increasing the stringency. The parameters that can be changed to affect stringency include, primarily, temperature and salt concentration. In general, the lower the salt concentration and the higher the temperature, the higher the stringency. Washing can be initiated at a low temperature (for example, room temperature) using a solution containing a salt concentration that is equivalent to or lower than that of the hybridization solution. Subsequent washing can be carried out using progressively warmer solutions having the same salt concentration. As alternatives, the salt concentration can be lowered and the temperature maintained in the washing step, or the salt concentration can be lowered and the temperature increased. Additional parameters can also be altered. For example, use of a destabilizing agent, such as formamide, alters the stringency conditions.

In reactions where nucleic acids are hybridized, the conditions used to achieve a given level of stringency will vary.

There is not one set of conditions, for example, that will allow duplexes to form between all nucleic acids that are 85% identical to one another; hybridization also depends on unique features of each nucleic acid. The length of the sequence, the composition of the sequence (for example, the content of purine-like nucleotides versus the content of pyrimidine-like nucleotides) and the type of nucleic acid (for example, DNA or RNA) affect hybridization. An additional consideration is whether one of the nucleic acids is immobilized (for example, on a filter).

An example of a progression from lower to higher stringency conditions is the following, where the salt content is given as the relative abundance of SSC (a salt solution containing sodium chloride and sodium citrate; 2×SSC is 10-fold more concentrated than 0.2×SSC). Nucleic acids are hybridized at 42° C. in 2×SSC/0.1% SDS (sodium dodecylsulfate; a detergent) and then washed in 0.2×SSC/0.1% SDS at room temperature (for conditions of low stringency); 0.2×SSC/0.1% SDS at 42° C. (for conditions of moderate stringency); and 0.1×SSC at 68° C. (for conditions of high stringency). Washing can be carried out using only one of the conditions given, or each of the conditions can be used (for example, washing for 10–15 minutes each in the order listed above). Any or all of the washes can be repeated. As mentioned above, optimal conditions will vary and can be determined empirically.

A second set of conditions that are considered "stringent conditions" are those in which hybridization is carried out at 50° C. in Church buffer (7% SDS, 0.5% NaHPO$_4$, 1 M EDTA, 1% BSA) and washing is carried out at 50° C. in 2×SSC.

Where a particular polypeptide or nucleic acid molecule is said to have a specific percent identity to a reference polypeptide or nucleic acid molecule of a defined length, the percent identity is relative to the reference polypeptide or nucleic acid molecule. Thus, a peptide that is 50% identical to a reference polypeptide that is 100 amino acids long can be a 50 amino acid polypeptide that is completely identical to a 50 amino acid long portion of the reference polypeptide. It might also be a 100 amino acid long polypeptide which is 50% identical to the reference polypeptide over its entire length. Of course, many other polypeptides will meet the same criteria. The same rule applies for nucleic acid molecules.

For polypeptides, the length of the reference polypeptide sequence will generally be at least 16 amino acids, preferably at least 20 amino acids, more preferably at least 25 amino acids, and most preferably 35 amino acids, 50 amino acids, or 100 amino acids. For nucleic acids, the length of the reference nucleic acid sequence will generally be at least 50 nucleotides, preferably at least 60 nucleotides, more preferably at least 75 nucleotides, and most preferably 100 nucleotides or 300 nucleotides.

In the case of polypeptide sequences which are less than 100% identical to a reference sequence, the non-identical positions are preferably, but not necessarily, conservative substitutions for the reference sequence. Conservative substitutions typically include substitutions within the following groups: glycine and alanine; valine, isoleucine, and leucine; aspartic acid and glutamic acid; asparagine and glutamine; serine and threonine; lysine and arginine; and phenylalanine and tyrosine.

Sequence identity can be measured using sequence analysis software (for example, the Sequence Analysis Software Package of the Genetics Computer Group, University of Wisconsin Biotechnology Center, 1710 University Avenue, Madison, Wis. 53705), with the default parameters as specified therein.

Oligonucleotides that are complementary to the 5' end of the message, e.g., the 5' untranslated sequence, up to and including the AUG initiation codon, are generally most efficient for inhibiting translation. However, sequences complementary to the 3' untranslated sequences of mRNAs have also been shown to be effective for inhibiting translation (Wagner, Nature, 372:333, 1984). Thus, oligonucleotides complementary to either the 5' or 3' non-translated, non-coding regions of a nonsense-mediated mRNA decay gene, e.g., the human homolog of NMD2, could be used in an antisense approach to inhibit translation of the endogenous human homolog of NMD2 mRNA. Oligonucleotides complementary to the 5' untranslated region of the mRNA should include the complement of the AUG start codon.

Antisense oligonucleotides complementary to mRNA coding regions are less efficient inhibitors of translation, but could be used in accordance with the invention. Whether designed to hybridize to the 5', 3', or coding region of a nonsense-mediated mRNA decay pathway mRNA, antisense nucleic acids should be at least six nucleotides in length, and are preferably oligonucleotides ranging from 6 to about 50 nucleotides in length. In specific aspects, the oligonucleotide is at least 10 nucleotides, or at least 50 nucleotides in length.

Regardless of the choice of target sequence, in vitro studies are usually performed first to assess the ability of an antisense oligonucleotide to inhibit gene expression. In general, these studies utilize controls that distinguish between antisense gene inhibition and nonspecific biological effects of oligonucleotides. In these studies levels of the target RNA or protein are usually compared with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide, and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule or hybridization. The oligonucleotide may include other appended groups such as peptides (e.g., for targeting host cell receptors in vivo), or agents facilitating transport across the cell membrane (as described, e.g., in Letsinger et al., Proc. Nat'l. Acad. Sci. USA 86:6553, 1989; Lemaitre et al., Proc. Nat'l. Acad. Sci. USA 84:648, 1987; PCT Publication No. WO 88/09810) or the blood-brain barrier (see, for example, PCT Publication No. WO 89/10134), or hybridization-triggered cleavage agents (see, for example, Krol et al., BioTechniques 6:958, 1988), or intercalating agents (see, for example, Zon, Pharm. Res. 5:539, 1988). To this end, the oligonucleotide can be conjugated to another molecule, e.g., a peptide, hybridization triggered cross-linking agent, transport agent, or hybridization-triggered cleavage agent.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D- galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-theouracil, 2-thiouracil, 4-thiouracil, 5-methyluracil, uracil-5-oxyacetic acid methylester, uracil-5-oxyacetic acid (v), 5-methyl-2-thiouracil, 2-(3-amino-3-N-2-carboxypropl) uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

The antisense oligonucleotide may also include at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal, or an analog of any of these backbones.

The antisense oligonucleotide can include an α-anomeric oligonucleotide. An α-anomeric oligonucleotide forms specific double-stranded hybrids with complementary RNA in which, contrary to the usual β-units, the strands run parallel to each other (Gautier et al., *Nucl. Acids. Res.* 15:6625, 1987). The oligonucleotide is a 2'-O-methylribonucleotide (Inoue et al., *Nucl. Acids Res.* 15:6131, 1987), or a chimeric RNA-DNA analog (Inoue et al., *FEBS Lett.* 215:327, 1987).

Antisense oligonucleotides of the invention can be synthesized by standard methods known in the art, e.g., by use of an automated DNA synthesizer (such as are commercially available from Biosearch, Applied Biosystems, etc.). As examples, phosphorothioate oligonucleotides can be synthesized by the method of Stein et al. (*Nucl. Acids Res.* 16:3209, 1988), and methylphosphonate oligonucleotides can be prepared by use of controlled pore glass polymer supports (Sarin et al., *Proc. Nat'l. Acad. Sci. USA* 85:7448, 1988).

While antisense nucleotides complementary to the coding region of a nonsense-mediated mRNA decay gene could be used, those complementary to the transcribed untranslated region are most preferred. These include antisense oligonucleotides, 20–30 nucleotides in length, complementary to sequences downstream of the cap site or 5' to the initiator AUG of the respective mRNAs. In yeast NMD2 mRNA, these regions include the mRNA sequences AAUGCUUAAAUAAUCUAAUAUUGUAUCUGC (SEQ ID NO:11) and UCUGCAUUGAUAAUAUCAUUGGACA-GAAAUU (SEQ ID NO:12; He and Jacobson, Genes & Dev. 9: 437–454, 1995). In the human UPF1 homologs, (RENT1; HUPF1), these regions include the sequences GGCG-GCUCGGCACUGWUACCUCUCGGUCCG (SEQ ID NO:13) and AACCGGCCCGAGGGCCCUACCCGGAGGCACC (SEQ ID NO:14);

Perlick et al., (1996) Proc. Nat. Acad. Sci. USA 93:10928–10932, 1996; Applequist et al., (1997) Nucleic Acids Res. 25:814–821).

The antisense molecules should be delivered to cells that express nonsense-mediated mRNA decay proteins in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense molecule sufficient to suppress translation of endogenous mRNAs. Therefore, an approach may be used in which a recombinant DNA construct comprises an antisense oligonucleotide placed under the control of a strong pol III or pol II promoter. The use of such a construct to transfect target cells in a patient will result in the transcription of sufficient amounts of single stranded RNAs that will form complementary base pairs with the endogenous nonsense-mediated mRNA decay pathway transcript and thereby prevent translation of that mRNA. For example, a vector can be introduced in vivo such that it is taken up by a cell and directs the transcription of an antisense RNA. Such a vector can remain episomal or become chromosomally integrated, as long as it can be transcribed to produce the desired antisense RNA.

Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Suitable promoters may include, but are not limited to: the SV40 early promoter region (Bernoist et al., *Nature* 290:304, 1981); the promoter contained in the 3' long terminal repeat of Rous sarcoma virus (Yamamoto et al., *Cell* 22:787–797, 1988); the herpes thymidine kinase promoter (Wagner et al., *Proc. Natl. Acad. Sci. USA* 78:1441, 1981); or the regulatory sequences of the metallothionein gene (Brinster et al., *Nature* 296:39, 1988). Constructs may also be contained on an artifical chromosome (Huxley, Trends. Genet. 13:345–347, 1997).

The production of an NMD2 antisense nucleic acid molecule by any gene therapeutic approach described above results in a cellular level of Nmd2p that is less than the amount present in an untreated individual.

Ribozymes

Ribozyme molecules designed to catalytically cleave nonsense-mediated mRNA decay pathway mRNAs (e.g., an NMD2 mRNA) can also be used to prevent translation of these mRNAs and expression of nonsense-mediated mRNA decay pathway mRNAs (see, e.g., PCT Publication WO 90/11364; Saraver et al., *Science* 247:1222, 1990). While various ribozymes that cleave mRNA at site-specific recognition sequences can be used to destroy specific mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art (Haseloff et al., *Nature* 334:585, 1988). Preferably, the ribozyme is engineered so that the cleavage recognition site is located near the 5' end of the nonsense-mediated mRNA decay mRNA, i.e., to increase efficiency and minimize the intracellular accumulation of non-functional mRNA transcripts.

Potential ribozyme sites in a nonsense-mediated mRNA decay pathway protein include 5'-UG-3' sites which correspond to the initiator methionine codon. UG-containing sequences are located throughout the yeast NMD2 mRNA, including those surrounding codon 3

(AGGA<u>UG</u>GACG) (SEQ ID NO:15), codons 17–18 (CU<u>UG</u>GAA <u>UG</u>GCGAAGAA)(SEQ ID NO:16), codon 121 (CUUU <u>UG</u>AGAAC) (SEQ ID NO:17), codon 203 (UAU<u>UG</u>CGA), and codon 404 (AUAUU<u>UG</u>GACAA)(SEQ ID NO:18), among others.

The ribozymes of the present invention also include RNA endoribonucleases (hereinafter "Cech-type ribozymes"), such as the one that occurs naturally in Tetrahymena Thermophila (known as the IVS or L-19 IVS RNA), and which has been extensively described by Cech and his collaborators (Zaug et al., *Science* 224:574, 1984; Zaug et al., *Science*, 231:470, 1986; Zug et al., *Nature* 324:429, 1986; PCT Application No. WO 88/04300; and Been et al., *Cell* 47:207, 1986). The Cech-type ribozymes have an eight base-pair sequence that hybridizes to a target RNA sequence, whereafter cleavage of the target RNA takes place. The invention encompasses those Cech-type ribozymes that target eight base-pair active site sequences present in nonsense-mediated mRNA decay pathway proteins.

As in the antisense approach, the ribozymes can be composed of modified oligonucleotides (e.g., for improved stability, targeting, etc.), and should be delivered to cells which express a nonsense-mediated mRNA decay pathway gene in vivo, e.g., heart, skeletal muscle, thymus, spleen, and small intestine. A preferred method of delivery involves using a DNA construct "encoding" the ribozyme under the control of a strong constitutive pol III or pol II promoter, so that transfected cells will produce sufficient quantities of the ribozyme to destroy endogenous nonsense-mediated mRNA decay pathway messages and inhibit translation. Because ribozymes, unlike antisense molecules, are catalytic, a lower intracellular concentration is required for efficiency.

For any of the above approaches, the therapeutic NMD2 antisense or ribozyme nucleic acid molecule construct is preferably applied to the site of the target area (for example, a hematopoetic stem cell in the case of β-thalassemia, delivered by injection), but can also be applied to tissue in the vicinity of the target area or even to a blood vessel supplying the target area.

For gene therapy, antisense or ribozyme NMD2 expression is directed from any suitable promoter (e.g., the human cytomegalovirus, simian virus 40, or metallothionein promoters), and its production is regulated by any desired mammalian regulatory element. For example, if desired, enhancers known to direct preferential gene expression in hematopoetic stem cells can be used to direct antisense NMD2 expression in a patient with β-thalassemia.

NMD2 antisense or ribozyme therapy is also accomplished by direct administration of an antisense NMD2 or ribozyme RNA to a target area. This mRNA can be produced and isolated by any standard technique, but is most readily produced by in vitro transcription using an antisense NMD2 DNA under the control of a high efficiency promoter (e.g., the T7 promoter). Administration of antisense NMD2 RNA to target cells is carried out by any of the methods for direct nucleic acid administration described above.

Other Methods for Reducing Nonsense-mediated mRNA Decay Pathway Expression

Endogenous nonsense-mediated mRNA decay can also be reduced by inactivating or "knocking out" the nonsense-mediated mRNA decay pathway gene or its promoter using targeted homologous recombination (see, e.g., U.S. Pat. No. 5,464,764). For example, a mutant, non-functional NMD2 nucleic acid sequence (or a completely unrelated DNA sequence) flanked by DNA homologous to the NMD2 gene (either the coding regions or regulatory regions of the NMD2 gene) can be used, with or without a selectable marker and/or a negative selectable marker, to transfect cells that express NMD2 in vivo. Insertion of the DNA construct, via targeted homologous recombination, results in inactivation of the NMD2 gene. Such approaches are particularly suited for use in the agricultural field where modifications to ES (embryonic stem) cells can be used to generate animal offspring with an inactive nonsense-mediated mRNA decay. However, this approach can be adapted for use in humans. For example, the recombinant DNA constructs may be directly administered or targeted to the pertinant cells in vivo using appropriate viral vectors.

Alternatively, endogenous nonsense-mediated mRNA decay pathway gene expression can be reduced by targeting deoxyribonucleotide sequences complementary to the regulatory region of the nonsense-mediated mRNA decay pathway gene (i.e., an NMD2 promoter and/or enhancers) to form triple helical structures that prevent transcription of an NMD2 gene in target cells in the body (Helene, *Anticancer Drug Res.* 6:569, 1981; Helene et al., *Ann. N.Y. Acad. Sci.* 660:27, 1992; and Maher, *Bioassays* 14:807, 1992).

Vectors

Vectors to be used as described above include retroviral vectors, adenoviral vectors, adeno-associated viral vectors, or other viral vectors with the appropriate tropism for Nmd2p-expressing cells (e.g., cells with activated nonsense-mediated mRNA decay pathways) can be used as a gene transfer delivery system for a therapeutic antisense nucleic acid construct or other nucleic acid construct that inhibits expression of a nonsense-mediated mRNA decay pathway gene (e.g., NMD2) expression. Numerous vectors useful for this purpose are generally known [Miller, *Human Gene Therapy* 15–14, (1990); Friedman, *Science* 244:1275–1281, (1989); Eglitis and Anderson, *BioTechniques* 6:608–614, (1988); Tolstoshev and Anderson, *Current Opinion in Biotechnology* 1:55–61, (1990); Sharp, *The Lancet* 337:1277–1278, (1991); Cornetta et al., *Nucleic Acid Research and Molecular Biology* 36:311–322, (1987); Anderson, *Science* 226:401–409, (1984); Moen, *Blood Cells* 17:407–416, (1991); and Miller and Rosman, *BioTechniques* 7:980–990, (1989); Le Gal La Salle et al., *Science* 259:988–990, (1993); and Johnson, Chest 107:77S–83S, (1995)]. Retroviral vectors are particularly well developed and have been used in clinical settings [Rosenberg et al., *N. Engl. J. Med* 323:370, (1990); Anderson et al., U.S. Pat. No. 5,399,346].

Non-viral approaches can also be employed for the introduction of therapeutic DNA into malignant cells. For example, an antisense NMD2 nucleic acid can be introduced into a carcinoma cell by the techniques of lipofection (Felgner et al., *Proc. Natl. Acad. Sci. USA* 84:7413, (1987); Ono et al., *Neurosci. Lett.* 117:259, (1990); Brigham et al., *Am. J. Med. Sci.* 298:278, (1989); Staubinger and Papahadjopoulos, *Meth. Enz.* 101:512, 1983); polylysine conjugation methods (Wu and Wu, *J. Biol. Chem.* 263:14621, 1988; Wu et al., *J. Biol. Chem.* 264:16985, 1989); or, by microinjection under surgical conditions (Wolff et al., *Science* 247:1465, 1990).

EXAMPLES

The invention will be further described in the following examples, which do not limit the scope of the invention described in the claims.

The examples illustrate the invention by describing the NMD2 gene, the Nmd2 protein, and its C-terminal fragment. Methods of substantially inhibiting the nonsense-mediated mRNA decay pathway in a cell, and methods of producing heterologous proteins and fragments of proteins are also described. These methods can inhibit the nonsense-mediated mRNA decay pathway to increase transcript stability. Other aspects the nonsense-mediated mRNA decay pathway can be affected, e.g., there can be increased read-through of nonsense codon-containing mRNAs. Inhibition of the nonsense-mediated mRNA decay pathway is useful for treating disorders involving a nonsense mutation.

Example 1

Identification of a Gene Encoding a Putative Upf1p-interacting Protein

To identify a gene or genes encoding putative Upf1p-interacting proteins, the yeast two-hybrid system was used. This method of detecting protein-protein interactions in yeast is based on the observation that the DNA binding and transcriptional activation functions of the GAL4 protein (Gal4p) can reside on two distinct chimeric polypeptides and still activate transcription from a GAL UAS (Upstream Activating Sequence), provided that the two polypeptides can interact with each other (Fields and Song, (1989) Nature 340:245–246; Chien, C.-T. et al., (1991) Proc. Natl. Acad. Sci. 88:9578–9582). As employed herein, the first hybrid was cloned into a plasmid (such as pMA424; (Ma, J. and Ptashne, M. (1988) Cell 55:443–446) in which the entire UPF1 coding region was fused in-frame to the Gal4p DNA binding domain (amino acids 1–147 of Gal4p). Construction of plasmid pMA424-UPF1 was performed by a three-fragment ligation. A fragment of 144 bp from the initial ATG codon to the 48th codon of UPF1 was amplified by the polymerase chain reaction (PCR) using UPF1-TH-5' (SEQ ID NO:5) and UPF1-TH-3' (SEQ ID NO:6) as oligonucleotide primers (Table 1).

TABLE 1

| Oligonucleotide Primers | |
| --- | --- |
| UPF-TH-5'  5'-CCGGAATTCATGGTCGGTTCCGGTTCT-3' | (SEQ ID NO:5) |
| UPF-TH-3'  5'-AGTGACTTGAGCCTC-3' | (SEQ ID NO:6) |

Amplification with these primers led to the introduction of an EcoRI site adjacent to the initiator ATG. The PCR-amplified fragment was digested with EcoRI and BstXI and ligated with a BstXI-BamHI fragment (including the rest of the UPF1 coding region and approximately 1 kb 3' distal to the translational termination site including the entire 3'UTR) into plasmid pMA424 digested by EcoRI and BamHI. DNA sequence analysis confirmed the primary structure of the construct.

Second hybrids were encoded by *S. cerevisiae* genomic DNA libraries in plasmids pGAD(1–3) (Chien et al. (1991) Proc. Nat'l. Acad. Sci USA 88:9578–9582) fused, in the three reading frames, to sequences encoding the Gal4p transcriptional activation domain (amino acids 768–881). Both were cotransformed into a *Saccharomyces cerevisiae* strain that contained an integrated GAL1-LacZ reporter construct (such as the *S. cerevisiae* strain GGY1::171 (Δgal4 Δgal80 URA3::GAL1-LacZ his3 leu2)) (Gill and Ptashne (1987) Cell 51:121–126) or equivalent strain well known to those of ordinary skill in the art of yeast genetics.

In performing the two-hybrid screening method, the GGY1::171 yeast strain was cotransformed with both pMA424-UPF1 and a library containing genomic DNA fragments fused to the GAL4 activation domain. After 3–4 days of growth on SD-His-Leu plates at 30° C., His$^+$Leu$^+$ transformants were replica-plated to SSX plates and were incubated until blue colonies appeared as described in Rose et al. (1990) *Methods in Yeast Genetics: A Laboratory Course Manual*, Cold Spring Harbor Laboratory, Cold Spring Harbor, N.Y.). False positive colonies due to cloning of the GAL4 gene into the pGAD vectors were eliminated by PCR yeast cellular DNA using the GAL4-specific primers GAL4–5' (from nucleotide 1206 to 1229 of the GAL4 gene) and GAL4–3' (from nucleotide 2552 to 2528 of the GAL4 gene) (Laughon and Gesteland, (1984) Mol. Cell Biol. 4:260–267). Cells from the remaining blue colonies were grown in SD-Leu medium and plasmids were recovered and transformed into the *E. coli* strain MH6 by electroporation. The activation domain (pGAD) plasmids from the library were identified by their ability to complement an *E. coli* leuB mutation due to the presence of the plasmid-borne LEU2 gene. According to the two-hybrid test, transcriptional activation depends interaction between the UPF1 fusion product and the test fragment fusion product. To confirm that transcriptional activation was dependent on the presence of both gene fusions, the isolated library plasmids were retransformed into the original GGY1::171 strain with either: 1) pMA424-UPF1, a GAL4 DNA-binding domain-UPF1 fusion plasmid; 2) pMA424, the GAL4 DNA binding domain vector only; 3) pMA424-CEP1, a GAL4 DNA-binding domain-CEP1 fusion plasmid; or 4) pMA424-LAM5, a GAL4 DNA-binding domain-LAM5 fusion plasmid, where CEP1 and LAM5 genes are negative control genes whose gene products are known not to bind to UPF1 gene product. Plasmids that yielded blue colonies only with the pMA424-UPF1 fusion were characterized further by restriction mapping, Southern analysis, and sequence analysis (see e.g., Sambrook et al., (1989), Molecular Cloning: A Laboratory Manual, Cold Spring Harbor Laboratory Press, Cold Spring Harbor, N.Y.). DNA sequences were compared to existing sequence databases using the FASTA program (Devereux et al., (1984) Nucleic Acids Res. 12:387–395). Colonies expressing detectable β-galactosidase activity were sought by screening approximately 400,000 transformants.

Eighty-seven colonies that demonstrated β-galactosidase activity (i.e., colonies pale blue to dark blue on X-Gal plates) on the initial screen were isolated. Because the libraries were constructed using genomic DNA from a GAL4 wild-type strain, plasmids containing the GAL4 gene, or fragments thereof, are capable of activating transcription of the GAL1-LacZ reporter gene. These false positive colonies were eliminated by use of the polymerase chain reaction (PCR; White et al., (1989) Trends Genet. 5:185–189) with GAL4 specific primers. The library plasmids from the remaining colonies were rescued and tested for specificity by retransforming them into the original strain with either: 1) the GAL4-UPF1 fusion; 2) the GAL4 DNA binding domain vector only; 3) an unrelated fusion, GAL4-CEP1; or 4) an unrelated fusion, GAL4-LAM5 (Bartel et al., (1993) Biotechniques 14:920–924). Forty-two plasmids that yielded blue colonies only with GAL4-UPF1 fusion plasmid-containing strains were characterized further by restriction mapping, Southern analysis, and partial DNA sequence analysis using standard techniques (see e.g., Sambrook et al., 1989, supra.

Blue colony formation occurred only when NMD2 and UPF1 fusion plasmids were present in the same host strain. The S. cerevisiae tester strain GGY1::171 was co-transformed with the original library isolate pGAD2-NMD2 and one of the following plasmids: 1) pMA424-UPF1, 2) pMA4242, 3) pMA424-CEP1, or 4) pMA424-LAM5 (pMA424-CEP1 was obtained from Richard Baker of the University of Massachusetts Medical Center, Worcester, Mass.; pMA424-LAMS was obtained from Stanley Fields and Paul Bartel of State University of New York, Stony Brook, N.Y.). Individual Leu$^+$ His$^+$ transformants were selected and streaked on synthetic medium plates lacking histidine and leucine. β-galactosidase activity assays were performed by replica-plating the transformants onto SSX plates containing X-Gal. Cells were incubated at 30° C. for 24–48 hours for development of blue color.

Southern blot analysis of the isolated plasmids was performed by first extracting total yeast genomic DNA according to the method of Holm et al. (1986) Gene 42:169–173. After restriction digestion, DNA was electrophoresed on 0.8% agarose gels, transferred and cross-linked to Zetaprobe membranes (BioRad, Richmond, Calif.) as described in Sambrook et al. (1989), supra. Filters were prehybridized for 2–3 hours at 42° C. in 5×SSPE, 40% formamide, 5×Denhardt's solution, 0.1% SDS, and 4 mg/ml salmon sperm DNA. A radiolabeled NMD2 probe (1.2 kb ClaI-EcoRI fragment), generated by random priming, was added and filters were hybridized overnight at 42° C. Filters were washed twice in 1×SSC, 0.1% SDS at room temperature and once in 0.1×SSC, 0.1% SDS at 58° C. before analyzing on a Betagen Blot Analyzer (Herrick, D. et al., (1991) Mol. Cell. Biol. 10:2269–2284).

DNA sequences were determined by the method of Sanger et al., (1978) Proc. Nat'l. Acad. Sci. USA 74:5463–5467. Overlapping fragments of the NMD2 gene were subcloned in Bluescript and sequenced by annealing oligonucleotide primers specific to the T3 or T7 promoter regions of the plasmid or by using oligonucleotide primers which annealed within the subcloned inserts.

Nine different genes were isolated by the following procedure. An S. cerevisiae genomic DNA library of Sau3A partial fragments constructed in YCp50 was used (Rose et al. (1987) Gene 60:237–243). Colony hybridization was performed as described in Sambrook et al., (1989), supra, using the same conditions described for the genomic DNA Southern hybridization. Approximately three genomic equivalents were screened. Disruption of the NMD2 gene was performed by transforming the diploid strain W303 (MATa/MATαade2-1/ade2-1 his3-11,15/his3-11,15 leu2-3,112/leu2-3,112 trp1-1/trp1-1 ura3-1/ura3-1 can1-100/can1-100) with a SacI-SalI fragment from Bs-nmd2::HIS3 and selecting His$^+$ transformants (the SacI and SalI sites are in the polylinker of the Bluescript KS$^+$ cloning vector, Stratagene, La Jolla, Calif.; Rothstein (1991) "Targeting, disruption, replacement, and allele rescue: integrative DNA transformation in yeast.", in *Methods in Enzymology* 194: *Guide to Yeast Genetics and Molecular Biology*, C. Guthrie and G. Fink, eds., Academic Press, pp. 281–301; Thomas and Rothstein (1989) Cell 56:619–630). The disruption event was confirmed by Southern analysis. Sporulation and tetrad analysis yielded haploid strains containing nmd2::HIS3 disruptions.

Six of the isolated genes encoded putative Upf1p-interacting proteins because their activity in the assay was dependent on fusion to the GAL4 activation domain. The remaining three genes did not require the presence of the GAL4 activation domain, were likely to possess their own activation domains and nuclear localization signals and were not examined further.

Six genes were found to encode putative Upf1p-interacting proteins; two genes are identical to previously characterized yeast genes, i.e., DBP2, a gene encoding a putative RNA helicase with homology to the mammalian p68 RNA helicase (Iggo et al., (1991) Mol. Cell. Biol. 11:1326–1333). The other four have no apparent homologues in the available data bases. One of the genes, herein named NMD2, is characterized herein, and its uses for the production of heterologous proteins in yeast are disclosed.

Example 2

Molecular Cloning of the NMD2 Gene

As defined by a qualitative β-galactosidase assay, Nmd2p showed a specific dependency on Upf1p in the two-hybrid system. Cells expressing a GAL4 activation domain-NMD2 fusion demonstrated strong β-galactosidase activity when simultaneously expressing a GAL4 DNA-binding domain-UPF1 fusion, but had no detectable β-galactosidase activity when co-transformed with plasmids encoding only the GAL4 DNA-binding domain-LAM5 fusion. Further evidence for the specificity of the interaction(s) was obtained by analyzing the effects of specific deletions within the UPF1 portion of the GAL4 DNA-binding domain-UPF1 fusion. Deletions in all but one segment of the UPF1 coding region eliminated Nmd2p-Upf1p interaction in the two-hybrid assay.

The GAL4 activation domain-NMD2 plasmid recovered in the two hybrid screen contained only a fragment of the NMD2 gene. To isolate the entire gene, a 1.2 kb ClaI-EcoRI fragment downstream of the GAL4 activation domain in the fusion plasmid was used to screen a yeast YCp50 genomic DNA library (Rose et al., (1987) supra). Two independent clones with identical restriction patterns were isolated. By restriction mapping, Southern analysis, and subsequent testing for complementation of an NMD2 chromosomal deletion, the NMD2 gene was localized to a 5.2 kb XbaI-SalI DNA fragment as shown in FIGS. 2A to 2C.

A restriction map of the nmd2::HIS3 allele is shown in FIG. 2A. The XbaI-ClaI fragment of the NMD2 gene, was deleted and replaced with the yeast HIS3 gene. The left arrow in FIG. 2A represents the HIS3 gene and indicates the direction of transcription. The right arrow of FIG. 2A represents the NMD2 open reading frame.

A restriction map of the NMD2 gene is shown in FIG. 2B. The NMD2 open reading frame and direction of transcription are indicated by an open arrow interrupted by a stippled box that indicates the position of the intron. The box labeled probe indicates the DNA fragment used for screening the genomic DNA library. In FIGS. 2A and 2B, the black box represents a segment from the cloning vector YCp50 and the restriction site abbreviations are: B, BamHI; C, ClaI; E, EcoRI; H, HindIII; P, PstI; S, SalI; Xb, XbaI.

To determine the regions of Nmd2p required for complementation of a disrupted nonsense mediated mRNA pathway in a nmd2::HIS3 strain, deletion experiments were performed. In FIG. 2C, lines represent DNA fragments which were subcloned into an appropriate vector (such as pRS315). These constructs were transformed into the yeast strain HFY1300, or equivalent, which contains a partial chromosomal deletion of NMD2 and lacks nonsense-mediated mRNA decay activity (see also, FIGS. 3A and 3B). Total RNA was isolated from these transformants and Northern analysis was performed using a radiolabeled probe derived from the CYH2 gene (He et al., (1993) Proc. Nat'l. Acad. Sci. USA 90:7034–7039). Complementing activity was scored by measuring the relative abundance of the CYH2 pre-mRNA and mRNA in each strain. (+) and (−) indicate the ability or inability, respectively, to complement the MD2 chromosomal deletion, i.e., to restore the CYH2 pre-mRNA to the marginally detectable levels characteristic of wild-type cells (He et al., (1993) Proc. Nat'l. Acad. Sci. USA 90:7034–7039).

To obtain a physical map position for the NMD2 gene, the 1.7 kb XbaI-ClaI fragment was used to probe PrimeClone blots (American Type Culture Collection, Rockville, Md.) containing characterized fragments of most of the *S. cerevisiae* genome (ATCC accession number 7155) known to lie on the right arm of chromosome VIII (Riles et al., (1993) Genetics 134:81–150). This fragment is located between the put2 and CUP1 loci at a map position approximately 260 kb from the left telomere (Riles et al., (1993) supra).

Example 3

Determining the Primary Sequence of the NMD2 Gene

Figure 1A:
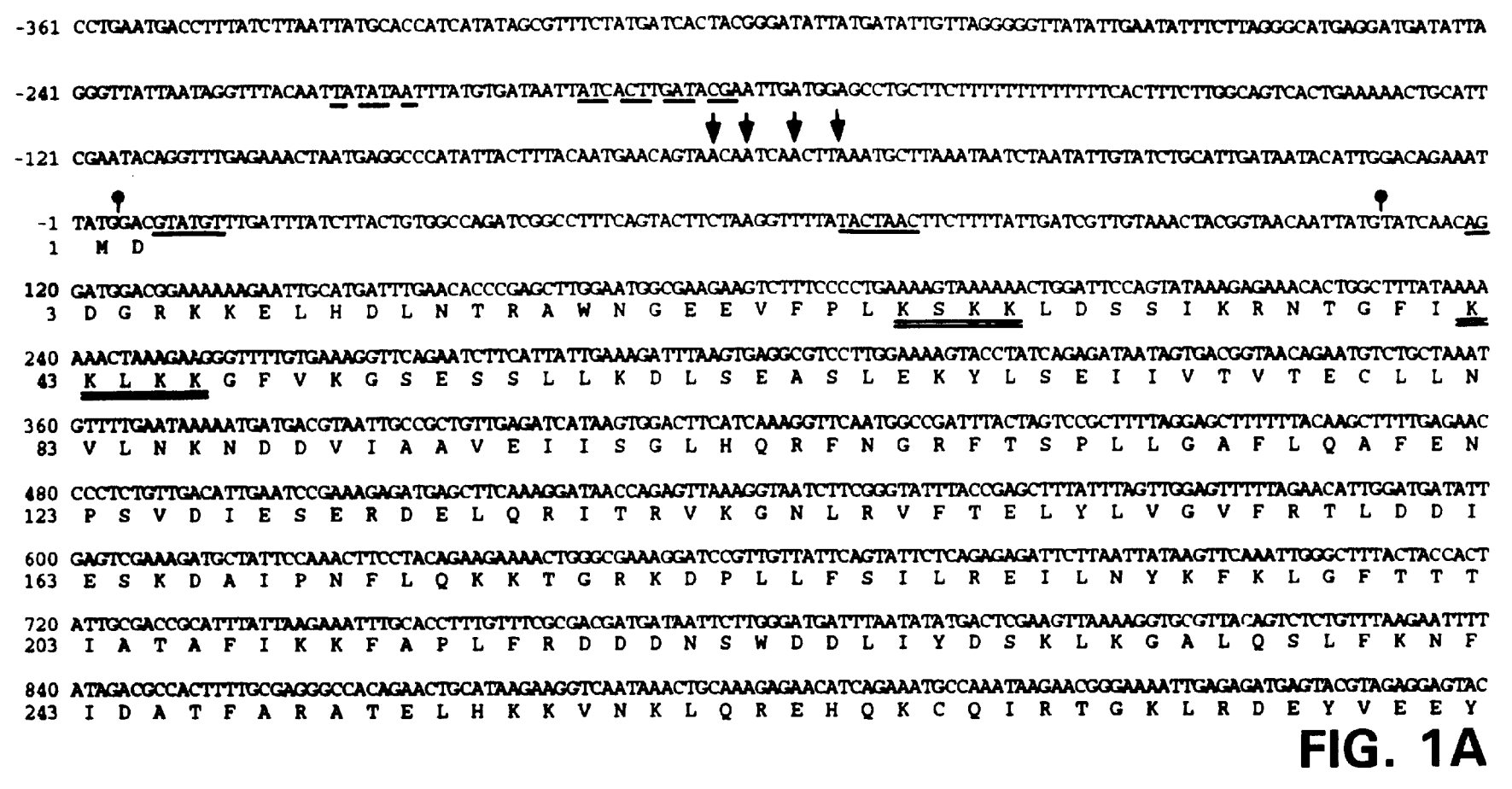
Figure 1B:
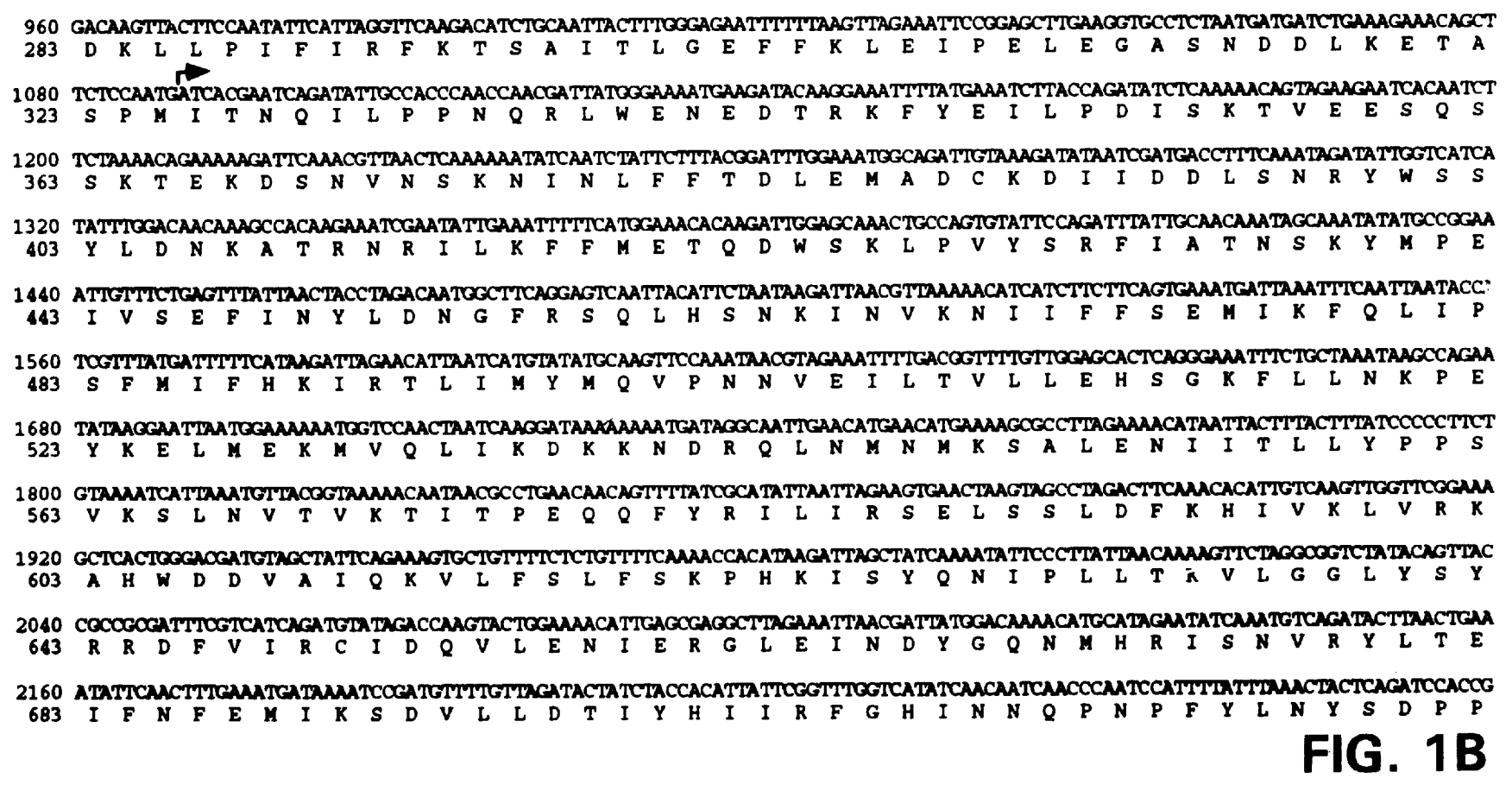
Figure 1C:
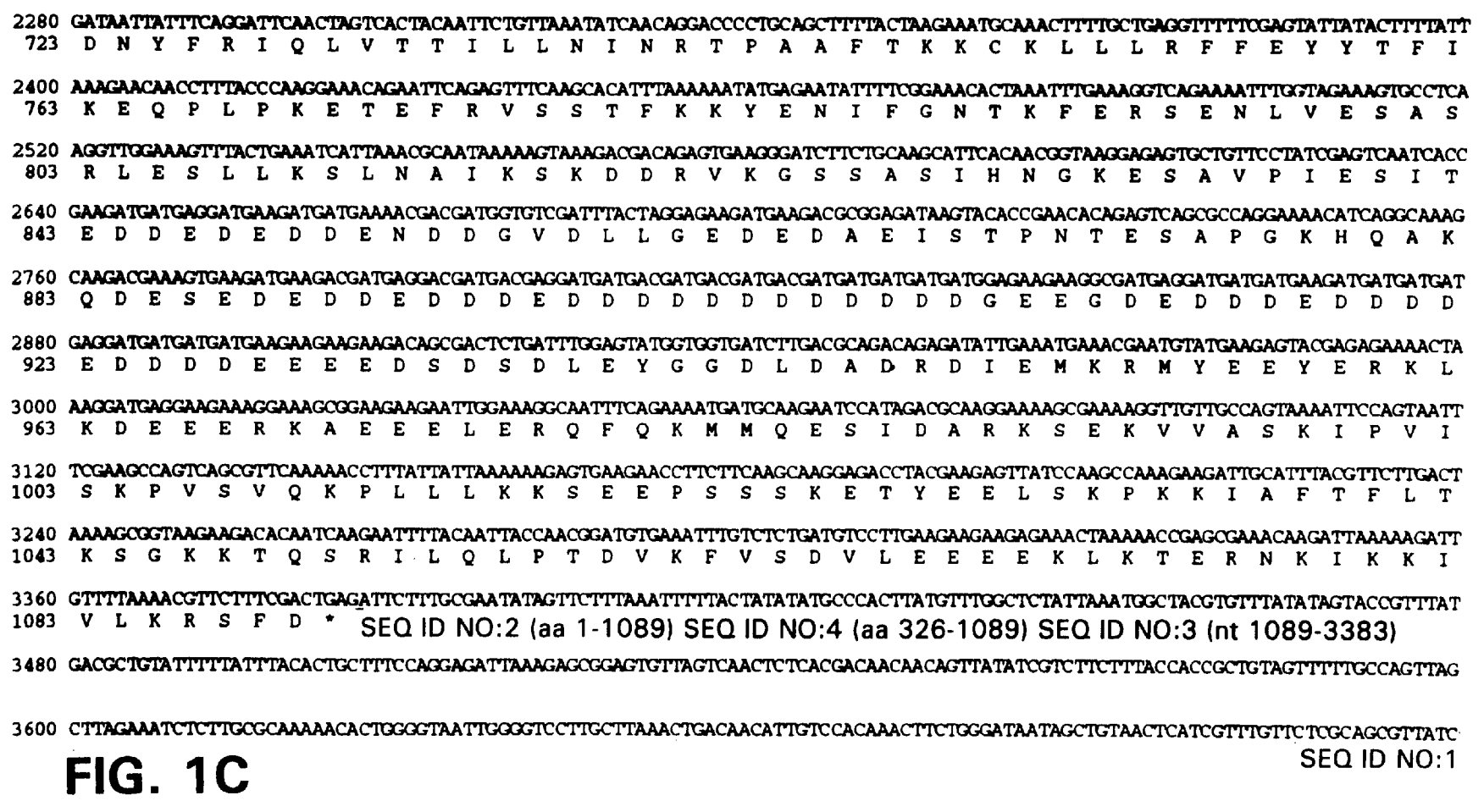

The complete sequence of the NMD2 gene was determined (SEQ ID NO:1). The NMD2 coding region is 3267 nucleotides in length, encoding an acidic (predicted pI=4.8) protein of 1089 amino acid residues (SEQ ID NO:2) with a predicted molecular weight of 127 kD. This interpretation of the NMD2 sequence relies on the prediction of a 113-nucleotide intervening sequence that commences at position +7 and divides the gene into two exons (FIGS. 1A–1C).

Four observations support the existence of this intron. First, the sequence contains all three of the standard consensus sequences expected of an intron (5' splice site [GUAUGU], branchpoint [UACUAAC], and 3' splice site [AG]) (FIGS. 1A–1C). Second, as is true for most introns in yeast (Fink (1987) Cell 49:5–6), this intron is located at the 5l end of the NMD2 gene (six nucleotides downstream from the predicted initiator ATG; FIGS. 1A–1C). Third, specific primer extension products were detected by using two different oligonucleotide primers complementary to mRNA sequences downstream of the predicted 3' splice site, but not by using a primer complementary to sequences within the intron. Finally, using the FLAG or c-MYC epitope tags (Hopp et al., (1988) Biotechnology 6:1204–1210; Prickett et al., (1989); Evan et al., (1985) Mol. Cell. Biol. 5:3610–3616) and epitope-specific monoclonal antibodies, the expression of a 127 kD polypeptide was detected when the FLAG or c-MYC sequences were inserted adjacent to the putative initiator ATG (FLAG-2-NMD2 or c-MYC-NMD2 alleles), but not when the FLAG sequence was inserted adjacent to the second ATG (FLAG-1-NMD2 allele). The second ATG is located within the putative intron, 37 nucleotides downstream of the predicted intron branchpoint, and is in frame with the major downstream open reading frame but not with the first ATG. It is important to note that both the FLAG-1-NMD2 and FLAG-2-NMD2 alleles are functional in that they both show wild-type ability to complement a chromosomal deletion of NMD2 (FIG. 2C). These results indicate that the FLAG-1 sequence inserted downstream of the second ATG has been removed by splicing out of the putative intron in the NMD2 gene.

Analysis of the NMD2 transcript was consistent with the predicted open reading frame. Northern analysis of total cellular RNA, using the NMD2 XbaI-ClaI fragment as a probe, identified a transcript of approximately 3.6 kb in size. Multiple transcription initiation sites were mapped to positions −56, −60, −64, and −67 using primer extension analysis (see e.g., Boorstein and Craig (1989) Meth. Enzymol. 180:347–369). A putative TATA box, required for most RNA polymerase II transcription (Struhl (1987) Cell. 49:295–297), lies at positions −219 to −213 in the NMD2 promoter region and another regulatory element, an Abf1p binding consensus sequence (Della Seta et al., (1990) J. Biol. Chem. 265:15168–15175), is located within positions −198 to −186 (FIGS. 1A–1C).

Structural features of the NMD2 protein (Nmd2p; SEQ ID NO:2) inferred from the sequence analysis include a highly acidic internal fragment (36.8% aspartic acid and 25.6% glutamic acid) from residues 843 to 975 near the C-terminus and a possible bipartite nuclear localization signal at the N-terminus of the protein (i.e., within residues 26 to 29 and 42 to 46) (FIGS. 1A–1C; Dingwall and Laskey, (1991) supra).

Comparison of the Nmd2p sequence with those in the Swissprot and Pir protein sequence databases using the FASTA or TFASTA comparison programs (Devereux et al., (1984) supra) did not reveal any extensive identity with known protein sequences. However, three domains of Nmd2p have substantial similarity to regions of other proteins. The first domain, spanning Nmd2p amino acids 1 to 390, has 17.7% sequence identity and 47% similarity with translational elongation factor 2 (Eft1p and Eft2p) from *S. cerevisiae* (Perentesis et al., (1992) J. Biol. Chem. 267:1190–1197). The second domain, from amino acids 400 to 810 in Nmd2p, shares 19.5% sequence identity and 42.6% similarity with the *S. cerevisiae* mitochondrial RNase P protein Rpm2p (Dang and Martin (1993) J. Biol. Chem. 268:19791–19796).

The third domain, encompassing the acidic stretch from amino acids 820 to 940, has 34% sequence identity and 63.2% similarity with human and mouse nucleoproteins (Lapeyre et al., (1987) Proc. Natl. Acad. Sci. 84:1472–1476; Bourbon et al., (1988) J. Mol. Biol. 200:27–638) and 34% identity and 65% similarity to the mammalian polymerase I transcriptional factors hUBF and mUBF (Jantzen et al., (1990) Nature 344:830–836; Hisatake et al., (1991) Nucleic Acids Res. 19:4631–4637). In hUBF and mUBF this domain has been shown to be important for interaction with other proteins (Jantzen et al., (1990) supra) and, as described below, is also true for Nmd2p.

Example 4

NMD2 Disruption Does Not Affect Cell Viability and Selectively Stabilizes Nonsense-containing mRNAs A NMD2 gene disruption experiment was performed to assess the cellular requirement for Nmd2p. The nmd2::HIS3 disruption described in FIG. 2A was constructed. Plasmid Bs-nmd2::HIS3 encodes the same NMD2 disruption and contains a 0.6 kb ClaI-XbaI fragment in the 5'-end of NMD2, a 1.7 kb XbaI-ClaI fragment of HIS3 and a 1.2 kb ClaI-EcoRI fragment in the NMD2 coding region in Bluescript. A SacI-SalI fragment carrying the nmd2::HIS3 allele was isolated from plasmid Bs-nmd2::HIS3 and used to transform the yeast diploid strain W303 for homologous recombination into one of the NMD2 alleles. His+ transformants were sporulated and tetrads were individually dissected. Four viable spores were obtained from each tetrad analyzed. Genomic DNAs from parental diploid and progeny haploid strains were isolated, digested with EcoRI. Confirmation of integration is shown by the Southern analysis of FIG. 3A in which lane P1 contains DNA isolated from the homozygous NMD2/NMD2 diploid strain W303; lane P2 contains DNA isolated from a diploid nmd2::HIS3/NMD2 His+ transformant of W303 (HFY1000); and lanes 1A to 1D contain DNA isolated from the progeny of four viable spores dissected from the same tetrad represent the wild-type and disrupted alleles of MD2, respectively. Other bands in the figure are not specific to NMD2.

Haploid strains containing the nmd2::HIS3 disruption were compared to isogenic NMD2 strains for their ability to grow on different carbon sources (glucose, galactose, and glycerol) at temperatures ranging from 18° C. to 37° C. and no differences in growth rates were detected between mutant and wild-type strains. These data indicate that NMD2 is non-essential for cell viability. Since disruption of the NMD2 gene was not lethal, the activities of the nonsense-mediated mRNA decay pathway in both NMD2 and nmd2::HIS3 strains were compared.

Figure 3B:
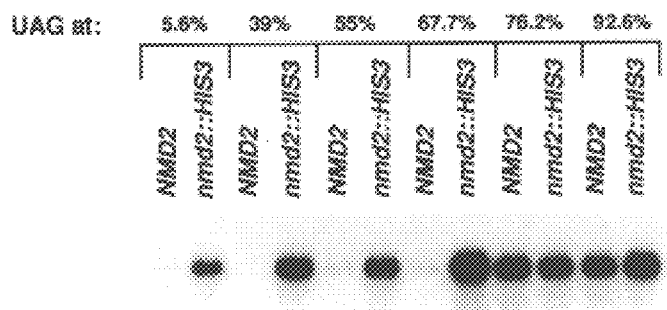

The following method was used to analyze transcript stability in strains having an NMD2 disruption, and is useful to one of ordinary skill in the art for analyzing the stability of any transcript of interest. Yeast centromere plasmids carrying six different PGK1 nonsense alleles were constructed previously (Peltz et al., (1993) supra). These plasmids were transformed into NMD2 and nmd2::HIS3 strains and the abundance of PGK1 nonsense-containing mRNAs was assessed by Northern analysis as shown in FIG. 3B. Disruption of the NMD2 gene stabilizes PGK1 mRNAs containing early nonsense mutations. Isogenic NMD2 and nmd2::HIS3 haploid yeast strains harboring different nonsense-containing PGK1 alleles (HFY1201 to HFY1206 and HFY1301 to HFY1306) were constructed by transforming HFY1200 and HFY1300 with each of the six plasmids harboring the nonsense-containing PGK1 alleles described previously (Peltz et al., (1993) Genes & Dev. 7:1737–1754) and herein incorporated by reference.

Total RNA was isolated from these strains and analyzed by Northern blotting using a radiolabeled oligonucleotide probe complementary to the tag sequence located in the 3' untranslated region of PGK1 nonsense-containing mRNAs (Peltz et al., (1993) Genes & Dev. supra). The location of the nonsense mutation in each PGK1 transcript is presented as a percentage of the PGK1 protein-coding region that is translated before the mutation is encountered (Peltz et al., (1993) supra).

Decay rates of mRNA were measured as previously described (Herrick et al., (1990) supra; Parker et al., (1991) Meth. Enzymol. 194:415–423; Peltz et al., (1993) supra). For measurement of mRNA abundance, yeast cells (20 ml) were grown to $OD_{600}$=0.5–0.7 at 24° C. for 30 minutes. An aliquot (2 ml) of concentrated cell culture was collected and frozen quickly on dry ice. Total yeast RNA was isolated as described previously (Herrick et al., (1991) supra). For both decay rate measurements and abundance measurements equal amounts (usually 20 µg) of total RNA from each sample were analyzed by Northern blotting, generally using probes labeled in random priming reactions (see, e.g., Sambrook et al., (1989) *Molecular Cloning: A Laboratory Manual*, 2nd ed., Cold Spring Harbor Laboratory Press, Cold Spring Harbor, N.Y.). Hybridization conditions for such blots were as described for genomic Southern hybridization. When oligonucleotide probes were used, the hybridization conditions were those described by Peltz et al. (1993) supra. Northern blots were quantitated with a Betagen Blot Analyzer (Herrick et al., (1990) supra).

Nonsense mutations in the 5' two-thirds of the PGK1 coding region reduced the abundance of the corresponding mRNAs 5- to 20-fold (Peltz et al., (1993) supra). The abundance of PGK1 mRNAs with nonsense mutations in the downstream third of the coding region is unaffected. Disruption of the MMD2 gene restored wild-type levels to all four of the PGK1 transcripts normally subject to nonsense-mediated mRNA decay (FIG. 3B). As a control, the abundance of the wild-type PGK1 and ACT1 mRNAs, and the half-life of the MATα1 mRNA in the same cells, was found to be unaffected by the nmd2::HIS3 disruption.

Figure 3C:
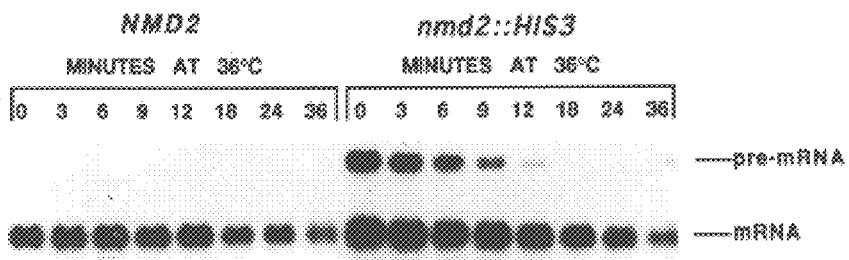

Northern analysis was also used to measure the relative abundance of the CYH2, RP51B, and MER2 pre-mRNAs in NMD2. As shown in FIG. 3C, decay rates of CYH2 pre-mRNA and mRNA were determined by Northern analysis of RNAs isolated at different time points after transcription was inhibited by shifting cultures of isogenic MD2 (HFY2206) and nmd2 (HFY2106) strains to 36° C. Samples were taken for 36 minutes and the blot was hybridized with a radiolabeled CYH2 DNA probe. To construct strains HFY2206 and HFY2106, strain HFY2000 was produced by integrative transformation; selected and tested to contain the temperature-sensitive rpb1-1 allele. Strain HFY2000 was transformed with pRS315 (or similar yeast shuttle plasmid; (Sikorski and Hieter, (1989) Genetics 122:19–27) or pRS315-NMD2(X-S) (containing a 5.2 kb XbaI-SalI fragment of NMD2 in pRS315) and a plasmid harboring a PGK1 allele with a nonsense mutation at the BglII site (Peltz et al., (1993) supra). The abundance of the inefficiently spliced CYH2 and RP51B pre-mRNAs, and the MER2 pre-mRNA (whose splicing is regulated by MER1; Engebracht et al., 1991) was markedly increased in strains carrying the nmd2::HIS3 disruption. Disruption of the NMD2 gene reduces the decay rate of the CYH2 pre-mRNA approximately four-fold, i.e., from a half-life of 1.5 min to a half-life of 6.0 min without a concomitant effect on the half-life of the CYH2 mRNA (FIG. 3C). These results are equivalent to those obtained in UPF1 knockout strains (He et al., (1993) sutra) indicating that Nmd2p is a Upf1p-interacting protein and that NMD2 is a novel component of the nonsense-mediated mRNA decay pathway.

Example 5

Overexpression of Truncated Nmd2p in the Cytoplasm Results in a Dominant-negative Nonsense-mediated mRNA Decay Phenotype The region of Nmd2p that interacts with Upf1p was determined by generating 5' and 3' deletions of the original MMD2 fragment, fusing them in-frame to the GAL4 activation domain, and assaying the resultant constructs for interaction with Upf1p using the two-hybrid system. Fusions encoding either 237 or 477 amino acids from the amino-terminus of the original fragment demonstrated no detectable β-galactosidase activity. However, fusions encoding either 526 or 286 amino acids from the carboxyl-terminus of the original fragment did demonstrate detectable β-galactosidase activity. These results indicate that the acidic C-terminal domain of Nmd2p interacts with Upf1p.

The identification of Nmd2p as a Upf1p-interacting protein in a two-hybrid screen and the observation that disruption of the NMD2 gene yielded a nonsense-mediated mRNA decay phenotype equivalent to that obtained in strains harboring upf1 mutations suggests that Upf1p and Nmd2p interact with each other in vivo and that they perform different functions in the same decay pathway. This conclusion is strengthened by the finding that double mutants in which both the UPF1 and NMD2 gene products are functionally absent produce strains that have essentially identical phenotypes with regard to the half-lives of test mRNA transcripts such as CYH2 pre-mRNA. Thus, Upf1p and Nmd2p must function in closely related steps of the nonsense-mediated mRNA decay pathway.

A truncated form of Nmd2p was expressed in both the nucleus and cytoplasm and activity was functionally localized within the cell to the cytoplasm. The original GAL4 activation domain-NMD2 fusion plasmid encodes 764 amino acids of the C-terminal segment of Nmd2p (SEQ ID NO:4). Transcription of this GAL4-activation domain-NMD2 fusion was driven by a cryptic promoter in the ADH1 terminator present in the vector and the fusion protein was targeted to the nucleus by the SV40 T antigen nuclear localization signal (Chien et al., (1991) supra. The 6.0 kb HindIII fragment encoding this fusion protein was also subcloned into pGAD2F so that transcription of the fusion protein was driven by the more potent ADH1 promoter. Since the SV40 T antigen nuclear localization signal (NLS) of the fusion protein is in a 36 bp EcoRI fragment (Benton et al., (1990) Mol. Cell. Biol. 10:353–360, we also generated deletions of the NLS in the respective constructs. Plasmids expressing the different fusion proteins were transformed into the haploid strain HFY1200 which is wild-type for both UPF1 and NMD2. HFY1200 was derived from W303 by standard techniques (see, e.g., Rothstein, R. (1991) "Targeting, disruption, replacement, and allele rescue: integrative DNA transformation in yeast.", in *Methods in Enzymology* 194: *Guide to Yeast Genetics and Molecular Biology*, C. Guthrie and G. Fink, eds., Academic Press, pp. 281–301). Control experiments, using the two hybrid assay, showed that when NMD2 plasmids lacking the T antigen NLS were co-transformed with the original plasmid encoding the GAL4 DNA binding domain-UPF1 fusion no β-galactosidase activity was detectable, i.e., nuclear localization had been eliminated. Total RNA was isolated from transformants and Northern analysis was performed using a fragment of the CYH2 gene as a probe.

Figure 4A:
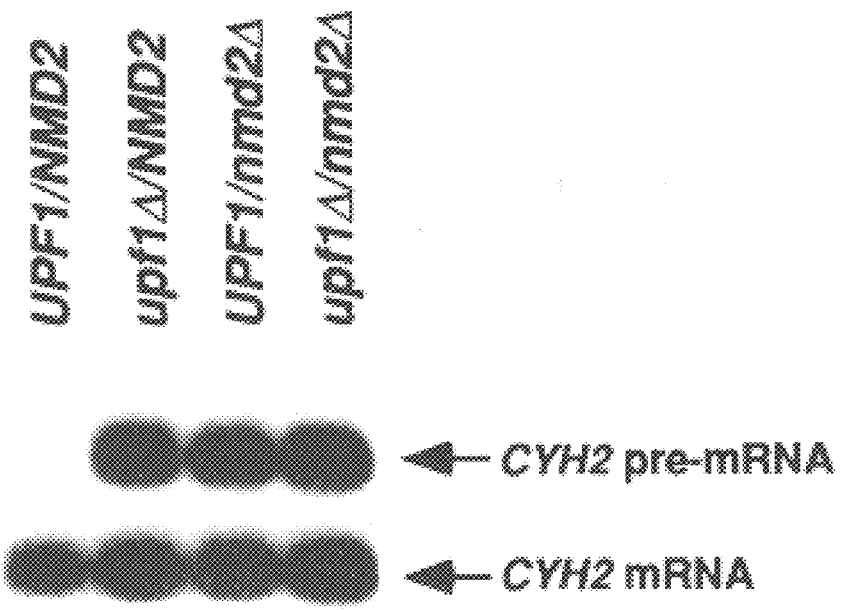
FIGS. 4A to 4B are representations of Northern analysis autoradiograms which record the CYH2 transcript stability phenotypes associated with disruption of both the NMD2 and UPF1 genes or overexpression of Nmd2p fragments.

The Northern analysis results depicted in FIG. 4A show that a double mutant containing both upf1::URA3 and nmd2::HIS3 disruptions is phenotypically identical to either upf1 or nmd2 single mutants since the CYH2 pre-mRNA is stabilized in cells containing these disruptions. Total RNAs were isolated from each of the following strains: HFY3002 (UPF1/NMD2); HFY3005 (upf1Δ/MD2); HFY3008 (UPF1Δ/nmd2Δ) and HFY3001 (upf1Δ/nmd2Δ) (see Table 2). RNAs were analyzed by Northern blotting using a radiolabeled CYH2 fragment as probe.

TABLE 2

Yeast Strains

| STRAIN | GENOTYPE |
|---|---|
| HFY1000 | MATa/MATα ade2-1/ade2-1 his3-11,15/his3-11,15 leu2-3,112/leu2-3,112 trpl-1/trp1-1 ura3-1/ura3-1 can1-100/can1-100 nmd2::HIS3/NMD2 |
| HFY1100 | MATα ade2-1 his3-11,15 leu2-3,112trp1-1 ura3-1 can1-100 NMD2 |

TABLE 2-continued

Yeast Strains

| STRAIN | GENOTYPE |
|---|---|
| HFY1200 | MATa ade2-1 his3-11,15 1eu2-3,112 trpl-1 ura3-1 can1-100 NMD2 |
| HFY1300 | MATα ade2-1 his3-11,15 leu2-3,112 trp1-1 ura3-1 can1-100 nmd2::HIS3 |
| HFY1400 | MATa ade2-1 his3-11,15 leu2-3,112 trp1-1 ura3-1 can1-100 nmd2::HIS3 |
| HFY1201 | Same as HFY1200 but containing [pRIPPGKH2 (3) UAG] |
| HFY1202 | Same as HFY1200 but containing [pRIPPGKAsp UAG] |
| HFY1203 | Same as HFY1200 but containing [pRIPPGKH2 (2) UA6] |
| HFY1204 | Same as HFY1200 but containing [pRIPPGKH2 (1) UAG] |
| HFY1205 | Same as HFY1200 but containing [pRIPPGKXba UAG] |
| HFY1206 | Same as HFY1200 but containing [pRIPPGKBg1 UAG] |
| HFY1301 | Same as HFY1300 but containing [pRIPPGKH2 (3) UAG] |
| HFY1302 | Same as HFY1300 but containing [PRIPPGKAsp UAG] |
| HFY1303 | Same as HFY1300 but containing [PRIPPGKH2 (2) UAG] |
| HFY1304 | Same as HFY1300 but containing [pRIPPGKH2 (1) UAG] |
| HFY1305 | Same as HFY1300 but containing [pRIPPGKXba UAG] |
| HFY1306 | Same as HFY1300 but containing [pRIPPGKBg1 UAG] |
| HFY2000 | MATα ade2-1 his3-11,15 leu2-3,112 trp1-1 ura3-1 can1-100 rpb1-1 nmd2::HIS3 |
| HFY2106 | Same as HFY2000 but containing [pRS315] [PRIPPGKBg1 UAG] |
| HFY2206 | Same as HFY2000 but containing [pRS315-NMD2 (X-S)] [pRIPPGKBg1 UAG] |
| HFY3000 | MATα ade2-1 his3-11,15 leu2-3,112 trp1-1 ura3-1 can1-100 nmd2::H153 upfl::URA3 |
| HFY3001 | Same as HFY3000 but containing [pRS3ls] [pRS314] |
| HFY3002 | Same as HFY3000 but containing [pRS315-NMD2 (X-S)] [pRS314-UPF1] |
| HFY3005 | Same as HFY2000 but containing [pR315-NMD2 (X-S)] [pRS314] |
| HFY3008 | Same as HFY2000 but containin9 [PRS315] [pRS314-UPF1] |

The strains listed in Table 2 were prepared in this study. See Peltz et al. (1993), supra, for a description of the "pRIPPGK__" plasmids listed above.

Figure 4B:
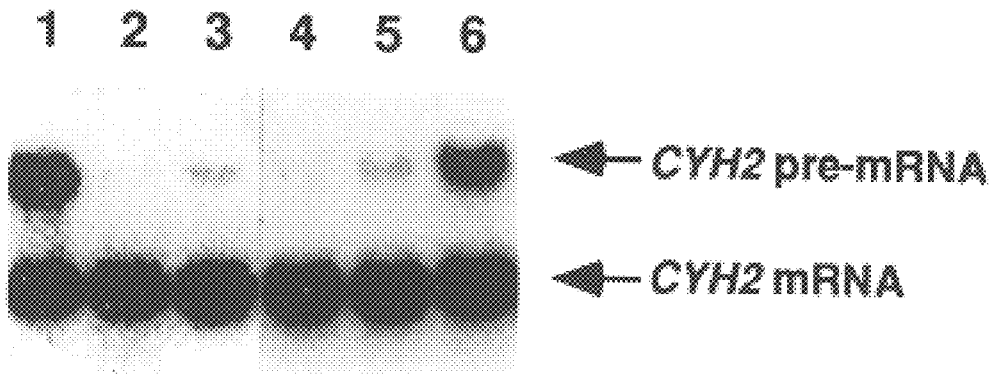

Overexpression of truncated Nmd2p in the cytoplasm results in a dominant-negative nonsense-mediated mRNA decay phenotype as shown in FIG. 4B. The yeast strain HFY1200 which is wild-type for both UPFL and NMD2 was transformed with pGAD2F-NMD2-ADHt, pGAD2F-NMD2-ADHp, pGAD2F, pGAD2F-NMD2-ADHt-ΔNLS, pGAD2NMD2-ADHp-ΔNLS, respectively (see Table 3). Total RNA was isolated from these transformants and analyzed by Northern blotting using a CYH2 DNA fragment as probe. Lane 1 contained RNA isolated from HFY1300 (control); RNA in other lanes was from transformants of HFY1200 harboring the following plasmids; lane 2, pGAD2F-NMD2-ADHt; lane 3, pGAD2F-NMD2-ADHp; lane 4, pGAD2F; lane 5, pGAD2F-NMD2-ADHt-ΔNLS; lane 6, pGAD2F-NMD2-ADHp-ΔNLS. Overexpression of truncated NMD2 fusion protein localized to the nucleus had no effect on the accumulation of the CYH2 pre-mRNA (FIG. 4B, lanes 2 and 3). Expression of the cytoplasmically localized fusion protein caused an accumulation of CYH2 pre-mRNA in a dosage dependent manner, i.e., expression of the fusion protein from the stronger promoter led to a greater accumulation of the CYH2 pre-mRNA than expression from the weaker promoter (FIG. 4B, lanes 5 and 6). This result establishes that over-expression of a truncated form of the Nmd2p C-terminus (i.e., containing up to 764 amino acids from the C-terminus (SEQ ID NO:4)) results in inhibition of the nonsense-mediated mRNA decay pathway. Shorter C-terminal fragments of Nmd2p are included in the invention as they are readily obtained by screening for inhibiting activity by the two-hybrid screening method coupled with analysis of heterologous transcript stability in the presence of overexpressed amounts of the fragment in the host strain.

TABLE 3

Plasmids

| PLASMIDS | RELEVANT YEAST SEQUENCES |
|---|---|
| pGAD2F | GAL4 activation domain-containing plasmid with 2µ and LEU2 selection markers (Chien, C.-T. et al. (1991) PNAS 88:9578–9582) |
| PGAD2F-NMD2-ADHP | 6.0-kb HindIII fragment from PGAD2-NMD2 replaced the 0.6-kb HindIII-HindIII fragment of pGAD2F such that the expression of the GAL4 activation domain -NMD2 fusion was driven by the ADH1 promoter. |
| pGAD2F-NMD2-ADHt | 6.0-kb HindIII fragment from PGAD2-NMD2 replaced the 0.6-kb HindIII-HindIII fragment of pGAD2F such that the expression of the GAL4 activation domain -NMD2 fusion was driven by the ADH1 terminator. |
| pGAD2F-NMD2-ADHP-ΔNLS | Same as pGAD2F-NMD2-ADHp except that the SV40 nuclear localization signal of the fusion protein was deleted. |
| pGAD2F-NMD2-ADHt-ΔNLS | Same as pGAD2F-NMD2-ADHt except that the SV40 nuclear localization signal of the fusion protein was deleted. |

Example 6

Expression of NMD2 Antisense Transcript Inhibits the Nonsense-Mediated mRNA Decay Pathway Nonsense-mediated mRNA decay pathway function of a host cell (i.e., a prokaryotic or eukaryotic cell such as a yeast cell) is reduced or inhibited by providing within the cell a portion of the antisense strand of the NMD2 gene introduced into cells in which NMD2 is transcribed. The antisense oligonucleotide (either RNA or DNA) can be directly introduced into the cells in a form that is capable of binding to the NMD2 sense transcripts. Alternatively, a vector containing sequence which, once within the host cells, is transcribed into the appropriate antisense mRNA, can be the species administered to the cells. An antisense nucleic acid that hybridizes to the mRNA of the target gene can decrease or inhibit production of the polypeptide product encoded by the gene by forming a double-stranded segment on the normally single-stranded mRNA transcript, thereby interfering with translation. It may be preferable to select sequences for antisense applications that do not contain nonsense codons as these may stimulate rather than inhibit the nonsense-mediated mRNA decay pathway.

A DNA sequence, such as a full or partial sequence of the NMD2 gene, is expressed as an antisense transcript. The sequence can be operably linked to appropriate expression control sequences and introduced into host cells by standard techniques well known to those of ordinary skill in the art. An effective amount of the expressed antisense transcript is produced such that translation of the NMD2 sense mRNA transcript is inhibited. By an equivalent method, UPF1 mRNA antisense transcript or a fragment thereof which binds to the UPF1 sense transcript, inhibiting translation and thereby, inhibiting the nonsense-mediated mRNA pathway. Antisense transcript production can be constitutive or controlled, as desired, according to the transcription regulatory sequences operably linked to the NMD2 or UPF1 DNA sequences for the production of antisense transcript.

Inhibition of the nonsense-mediated mRNA pathway using antisense transcripts to inhibit translation of a protein of the pathway (such as NMD2 or UPF1) is useful to enhance the stability of a nonsense codon-containing transcript which encodes a heterologous polypeptide to be produced in yeast cells or to enhance the production of a mutated endogenous polypeptides useful to the host cell or host organism.

Antisense transcripts are also useful for treating genetic disorders involving a nonsense mutation. For example, using gene therapy methods known to those in the art, a vector able to express antisense transcripts for a gene in the nonsense-mediated mRNA decay pathway (e.g., NMD2 or UPF1) is introduced into a patient harboring a disease-causing nonsense mutation.

Example 7

Production of Heterologous Protein or Polypeptide in a Yeast Cell Inhibited in the Nonsense-Mediated mRNA Pathway A protein or polypeptide of interest is produced by providing an expression vector encoding a gene for a heterologous protein. The expressed transcript of the gene encodes a nonsense codon in a transcript destabilizing 5' portion of the transcript such that the transcript is at least 2 fold less stable in a wild-type strain than in a nonsense-mediated mRNA decay-inhibited host strain. Nonsense-mediated mRNA decay is inhibited by 1) mutating the NMD2 gene such that no functional Nmd2p is produced; 2) overexpressing a C-terminal fragment of Nmd2p such that the fragment binds to UPF1 inhibiting its function; or 3) expressing sufficient NMD2 or UPF1 antisense transcript to hybridize to NMD2 or UPF1 sense transcript preventing its translation into functional Nmd2p or Upf1p, respectively. All of these methods can be carried out by standard procedures.

If it is desired that an amino acid be substituted at the nonsense codon position, then the host strain used is also an amino acid substitution suppressor strain. The suppressor strain is chosen such that a specific amino acid (dictated by the type of suppressor mutation in the host strain) is substituted at the nonsense codon. The substituted amino acid can be an amino acid encoded by the natural codon at that site. The substituted amino acid can be different from the naturally encoded amino acid if it is desired to test the effect of that amino acid on the conformation or activity of the encoded protein.

If the heterologous protein to be expressed is toxic to the host cell, inhibition of the nonsense-mediated mRNA decay pathway can be controlled by the inducible expression of, for example, Nmd2p C-terminal fragment or NMD2 antisense transcript. Controllable inhibition of the decay pathway allows transcript stabilization and translation a point in the host yeast cell culture growth such that maximum production of the toxic protein occurs prior to the death of the host cells.

Following inhibition of the nonsense-mediated mRNA pathway and translation of the stabilized nonsense codon-containing transcript into the desired heterologous protein or protein fragment, the protein or fragment is isolated from the yeast host cells by standard protein purification methods.

Example 8

Production of Antibody to Nmd2p or a C-terminal Fragment of Nmd2p

Nmd2p or Nmd2p C-terminal fragment polypeptide of the invention can be produced by first transforming a suitable host cell with the entire NMD2 gene (for the production of Nmd2p) or with a partial NMD2 sequence (encoding the C-terminal part of Nmd2p), respectively, cloned into a suitable expression vehicle followed by expression of the desired protein or polypeptide.

Those of ordinary skill in the field of molecular biology will understand that any of a wide variety of expression systems can be used to provide the protein or polypeptide. The precise host cell used is not critical to the invention. The polypeptide can be produced in a prokaryotic host (e.g., *E. coli*) or in a eukaryotic host (e.g., *Saccharomyces cerevisiae*). The method of transformation of the cells and the choice of expression vehicle will depend on the host system selected. Methods described herein provide sufficient guidance to successfully carry out the production, purification and identification of Nmd2p or THE Nmd2p C-terminal fragment.

Once the Nmd2p or Nmd2p C-terminal fragment (or fragment or analog thereof) is expressed, it is isolated, e.g., using immunoaffinity chromatography. In one example, an anti-Nmd2p or anti-(Nmd2p C-terminal fragment) antibody can be attached to a column and used to isolate Nmd2p or Nmd2p C-terminal fragment, respectively. Lysis and fractionation of Nmd2p or Nmd2p C-terminal fragment-containing host cells prior to affinity chromatography can be performed by standard methods. Once isolated, the recombinant protein can, if desired, be further purified, e.g. by high performance liquid chromatography (see e.g., Fisher, *Laboratory Techniques In Biochemistry and Molecular Biology*, eds., Work and Burdon, Elsevier, (1980).

Nmd2p or fragments thereof, particularly short fragments which inhibit the nonsense-mediated mRNA decay pathway, can also be produced by chemical synthesis, by standard solution or solid phase peptide synthesis techniques.

Substantially pure Nmd2p or Nmd2p C-terminal fragment can be used to raise antibodies. The antibodies are useful for screening, by Western blot analysis, host stains overexpressing Nmd2p or Nmd2p C-terminal fragment, thereby identifying candidate strains which produce a desired amount of Nmd2p or Nmd2p C-terminal fragment.

Antibodies directed to the polypeptide or interest, Nmd2p or NMd2p C-terminal fragment, are produced as follows. Peptides corresponding to all or part of the polypeptide of interest are produced using a peptide synthesizer by standard techniques, or are isolated and purified as described above. The peptides are coupled to KLH with M-maleimide benzoic acid N-hydroxysuccinimide ester. The KLH-peptide is mixed with Freund's adjuvant and injected into animals, e.g., guinea pigs or goats, to produce polyclonal antibodies.

Monoclonal antibodies can be prepared using the polypeptide of interest described above and standard hybridoma technology (see, e.g., Kohler et al., Nature (1975) 256: 495; Kohler et al., Eur. J. Immunol. (1976) 6:292, Kohler et al., Eur. J. Immunol. (1976) 6:511; Hammerling et al., in *Monoclonal Antibodies and T Cell Hybridomas*, Elsevier, N.Y., (1981), which are incorporated herein by reference). Antibodies are purified by peptide antigen affinity chromatography.

Once produced, antibodies are tested for specific Nmd2p or Nmd2p C-terminal fragment binding by Western blot or immunoprecipitation analysis by standard techniques.

In addition, techniques developed for the production of "chimeric antibodies" (Morrison et al., *Proc. Natl. Acad. Sci. USA*, 81:6851, 1984; Neuberger et al., *Nature*, 312–604, 1984; Takeda et al., *Nature*, 314:452, 1984) can be used. These methods involve splicing the genes from a mouse antibody molecule of appropriate antigen specificity together with genes from a human antibody molecule of appropriate biological activity. A chimeric antibody is a molecule in which different portions are derived from different animal species, such as those having a variable region derived from a murine having a variable region derived from a murine mAb and a human immunoglobulin constant region.

Example 9

Identification of Murine Homologs of Yeast NMD2

Several different approaches to identifying murine NMD2 homologs can be utilized.

In one approach, comparative genomics are used to identify murine homologs of NMD2. The sequence of the complete yeast NMD2 protein is compared to existing databases of random cDNA sequences (Bassett, D. J., et al., *Trends Genet.* 1:4372–373, 1995). Fragments with significant homology to NMD2 are used as nucleic acid probes in subsequent screens of murine genomic DNA and cDNA libraries as described herein. Full-length genes and cDNAs having substantial homology to NMD2 are then further characterized as described herein.

Two-hybrid screens can also be used to identify murine homologs of NMD2. Mouse genes enclding proteins that interact with yeast UPF1 or UPF3 proteins (He et al., *Mol. Cell. Biol.* 17:1580–1594, 1997), or human homologs of the yeast UPF1 protein (Perlick et al., Proc. Natl. Acad. Sci. USA 93:10928–10932, 1996; Applequist et al., Nucleic Acids Res. 25:814–821, 1997), are identified using the two-hybrid method (Fields and Song, Nature 340:245–246, 1989; Chien et al., Proc. Natl. Acad. Sci. USA 88:9578–9582, 1991; Fields and Sternglanz, Trends Genet. 10:286–292, 1994; Bartel and Fields, Methods Enzymol. 254:241–263, 1995). DNA encoding the UPF protein is cloned and expressed from plasmids harboring GAL4 or lexA DNA-binding domains and co-transformed into cells harboring lacZ and HIS3 reporter constructs along with libraries of cDNAs that have been cloned into plasmids harboring the GAL4 activation domain. Libraries used for such co-transformation include those made from B-cells and T-cells since such cells may have high activities of the nonsense-mediated mRNA decay pathway.

Another method for identifying murine homologs of NMD2 utilize complementation of yeast NMD2 mutants. Yeast UPF1 mutants incapable of nonsence-mediated mRNA decay suppress the growth defects of cells harboring nonsense mutations in the LEU2 or TYR7 genes (Leeds et al., Mol. Cell. Biol. 12:2165, 1992; Peltz et al., Prog. Nucleic Acids Res. Molec. Biol. 47:271–298, 1994). Comparable effects are observed with NMD2 mutants, or in cells harboring the NMD2 dominant-negative fragment. In all of these cases, cells with the leu2-3 or tyr7-1 nonsense mutations fail to grow in the absence of leucine or tyrosine, respectively, if they are wild-type for nonsense-mediated mRNA decay and will grow in the absence of these amino acids if they have defects in the nonsense-mediated mRNA decay pathway. Therefore, NMD2 mutants, or cells harboring the NMD2 dominant-negative fragment, are transformed with mammalian cDNA libraries cloned into yeast plasmid vectors. The transformants are analyzed for restoration of the wild-type pattern, i.e., failure to grow in the absence of leucine or tyrosine.

Alternatively, the transformed cells are screened for their ability to grow in the presence of 100 μg/ml of the growth inhibitor canavanine. This drug enters cells via arginine permease, a protein encoded by the CAN1 gene. Cells harboring the can1-nonsense mutation are resistant to 100 µg/ml canavanine if they are wild-type for nonsense-mediated mRNA decay, but sensitive to it if they also harbor an NMD2 mutation. Hence, restoration of NMD2 function by exogenous DNA is assessed by plating cells on canavanine. Plasmids are isolated from the cells surviving on canavanine, the plasmids are sequenced, and the sequences analyzed to confirm murine sequence that complements mutant nmd2 (e.g., the cell is not a revertant).

PCR with degernate oligonucleotides is also a method of identifying murine NMD2 homologs. Homologs of the NMD2 gene are identified in other, non-murine, species are compared to identify specific regions with a high degree of homology. These regions of high homology are selected for the design of PCR primers that maximize possible base-pairing with heterlogous genes. Construction of such primers involves the use of oligonucleotide mixtures that account for degeneracy in the genetic code, i.e., allow for the possible base changes in murine NMD2 genes that do not affect the amino acid sequence of the NMD2 protein. Such primers are used to amplify and clone possible NMD2 gene fragments from mouse DNA. The latter are sequenced and those encoding protein fragments with high degrees of homology to fragments of yeast NMD2 protein are used as nucleic acid probes in subsequent screens of murine genomic DNA and cDNA libraries. Full-length genes and cDNAs having substantial homology to yeast NMD2 are identified in these screens.

Example 10

Identification of Human Homologs of Yeast NMD2

The human homolog of the yeast NMD2 gene is useful for the elucidation of the biochemical pathways of nonsense-mediated mRNA decay in mammals as well as for the development of treatments for genetic disorder involving nonsense mutations. Several approaches can be used to isolate human NMD2 genes including a two-hybrid screen, complementation of yeast NMD2 mutants by expression libraries of cloned human cDNAs, polymerase chain reactions (PCR) primed with degenerate oligonucleotides, low stringency hybridization screens of human libraries with the yeast NMD2 gene, and database screens for homologous sequences. The human NMD2 gene can also be identified by appropriate application of the above methods based on homology with the mouse NMD2 gene homolog.

Methods of screening for and identifying human homologs of NMD2 are described above (e.g., Example 8). In addition, the murine homolog of NMD2 can be used instead of the yeast Nmd2 sequence to probe a human cDNA or genomic DNA library for homologous sequences.

To produce the human NMD2 gene product (e.g., human Nmd2p) the human ND2 gene is placed in an expression vector and the gene expressed in an appropriate cell type. Human Nmd2p is isolated from such cell lines using methods known to those in the art, and used in the assays described below.

Example 11

Methods of Screening for Molecules that Inhibit the Nonsense-mediated mRNA Decay Pathway The following assays are designed to identify compounds that are effective inhibitors of the nonsense-mediated mRNA decay pathway. Such inhibitors may act by, but are not limited to, binding to an Ndm2p (e.g., from yeast, mouse or human), binding to intracellular proteins that bind to an Nmd2p, compounds that interfere with the interaction between Nmd2p and nonsense mutation-containing mRNA, compounds that modulate the activity of an NMD2 gene, or modulate the expression of an NMD2 gene or an Nmd2p.

Assays can also be used to identify molecules that bind to nonsense-mediated mRNA decay pathway gene regulatory sequences (e.g., promoter sequences), thus modulating gene expression. See e.g., Platt, 1994. *J. Biol. Chem.* 269:28558–28562, incorporated herein in its entirety.

The compounds which may be screened by the methods described herein include, but are not limited to, peptides and other organic compounds (e.g., peptidomimetics) that bind to a nonsense-mediated mRNA decay pathway protein (e.g., that bind ton an Nmd2p), or inhibit its activity in any way.

Such compounds may include, but ar not limited to, peptides; for example, soluble peptides, including but not limited to members of random peptide libraries; (see, e.g., Lam et al., 1991. *Nature* 354:82–94; Houghten et al., 1991. *Nature* 354:84–86), and combinatorial chemistry-derived molecular libraries made of D-and/or L-amino acids, phosphopeptides (including, but not limited to, members of random or partially degenerate, directed phosphopeptide libraries; see e.g., Songyang et al., 1993. *Cell* 72:767–778), and small organic or inorganic molecules.

Organic molecules are screened to identify candidate molecules that affect expression of a nonsense-mediated mRNA decay (e.g., NMD2) gene or some other gene involved in the nonsense-mediated mRNA decay pathway (e.g., by interacting with the regulatory region or transcription factors of a gene). Compounds are also screened to identify ones that affect the activity of such proteins, (e.g., by inhibiting Nmd2p activity) or the activity of a molecule involved in the regulation of, for example, Nmd2p.

Computer modelling or searching technologies are used to identify compounds, or identify modifications of compounds that modulate the expression or activity of a nonsense-mediated mRNA decay protein. For example, compounds likely to interact with the active site of a protein (e.g., Nmd2p) are identified. The active site of an Nmd2p molecule can be identified using methods known in the art including, for example, analysis of the amino acid sequence of a molecule, from a study of complexes of Nmd2p, with its native ligand (e.g., Upf1p). Chemical or X-ray crystallographic methods can be used to identify the active site of Nmd12p by the location of a bound ligand such as Upf1p.

The three-dimensional structure of the active site is determined. This can be done using known methods, including X-ray crystallography which may be used to determine a complete molecular structure. Solid or liquid phase NMR can be used to determine certain intra-molecular distances. Other methods of structural analysis can be used to determine partial or complete geometrical structures. Geometric structure can be determined with an Nmd2p bound to a natural (e.g., Upf1p) or artificial ligand which may provide a more accurate active site structure determination.

Computer-based numerical modelling can be used to complete an incomplete or insufficiently accurate structure. Modelling methods that may be used are, for example, parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups are necessary, and can be selected from force field known in physical chemistry. Information on incomplete or less accurate structures determined as above can be incorporated as constraints on the structures computed by these modeling methods.

Having determined the structure of the active site of a nonsense-mediate mRNA protein (.e.g, Nmd2p, either experimentally, by modeling, or by a combination of methods, candidate modulating compounds can be identified by searching databases containing compounds along with information on their molecular structure. The compounds identified in such a search are those that have structures that match the active site structure, fit into the active site, or interact with groups defining the active site. The compounds identified by the search are potential nonsense-mediated mRNA decay pathway modulating compounds.

These methods may also be used to identify improved modulating compounds from an already known modulating compound or ligands. The structure of the known compound is modified and effects are determined using experimental and computer modelling methods as described above. The altered structure may be compared to the active site structure of a nonsense-mediated mRNA decay protein (e.g., an Nmd2p) to determine or predict how a particular modification to the ligand or modulating compound will affect its interaction with that protein. Systematic variations in composition, such as by varying side groups, can be evaluated to obtain modified modulating compounds or ligands of preferred specificity or activity.

Other experimental and computer modeling methods useful to identify modulating compounds based on identification of the active sites of a nonsense-mediated mRNA decay protein and related transduction and transcription factors will be apparent to those of skill in the art.

Examples of molecular modelling systems are the QUANTA programs, e.g., CHARMm, MCSS/HOOK, and X-LIGAND, (Molecular Simulations, Inc., San Diego, Calif.). QUANTA analyzes the construction, graphic modelling, and analysis of molecular structure. CHARMm analyzes energy minimization and molecular dynamics functions. MCSS/HOOK characterizes the ability of an active site to bind a ligand using energetics calculated via CHARMm. X-LIGAND fits ligand molecules to electron density of protein-ligand complexes. It also allows interactive construction, modification, visualization, and analysis of the behavior of molecules with each other.

Articles reviewing computer modelling of compounds interacting with specific protein can provide additional guidance. For example, see Rotivinen et al., 1988 *Acta Pharmaceutical Fennica* 97:159–166: Ripka, *New Scientist* 54–57 (Jun. 16, 1988); McKinaly and Rossmann, 1989, *Ann. Rev. Pharmacol. Toxicol.* 29:111–122; Perry and Davies. *OSAR Quantitative Structure-Activity Relationships in Drug Design* pp. 189–193 (Alan R. Liss, Inc., 1989); Lewis and Dean, 1989, *Proc. R. Soc. Lond.* 236:125–140, 141–152; and, regarding a model receptor for nucleic acid components, Askew et al., *Am. J. Chem. Soc.* 111:1082–1090. Computer programs designed to screen and depict chemicals are available from companies such as MSI (supra), Allelix, Inc. (Mississauga, Ontario, Canada), and Hypercube, Inc. (Gainesville, Fla.).

These applications are largely designed for drugs specific to particular proteins; however, they can be adapted to the design of drugs specific to identified regions of DNA or RNA. Chemical libraries that can be used in the protocols described herein include those available, e.g., from ArQule, Inc. (Medford, Mass.) and Oncogene Science, Inc. (Uniondale, N.Y.).

In addition to designing and generating compounds that alter binding, as described above, libraries of known compounds, including natural products, synthetic chemicals, and biologically active materials including peptides, can be screened for compounds that are inhibitors or activators of the nonsense-mediated mRNA decay pathway.

Compounds identified by methods described above can be used, for example, for elaborating the biological function of nonsense-mediated mRNA decay pathway gene products (e.g., an Nmd2p), and to treat genetic disorders involving a nonsense mutation. Assays for testing the effectiveness of compounds such as those described herein are further described below.

Example 12

In vitro Screening Assays for Compounds that Bind to Nonsense-mediated Decav Proteins and Genes In vitro systems can be used to identify compounds that interact with (e.g., bind to) nonsense-mediated decay pathway proteins or genes encoding those proteins (e.g., a UPF1, UPF3, or NMD2 gene). Such compounds are useful, for example, for modulating the activity of these entities, elaborating their biochemistry, or treating disorders involving nonsense mutations. These compounds can be used in screens for compounds that disrupt normal function, or may themselves disrupt normal function.

Assays to identify compounds that bind nonsense-mediated decay pathway proteins involve preparation of a reaction mixture of the protein and the test compound under conditions sufficient to allow the two components to interact and bind, thus forming a complex which can be removed and/or detected.

Screening assays can be performed using a number of methods. For example, a nonsense-mediated RNA decay pathway protein from an organism (e.g., UPF1 , NMD2, UPF3, NMD3, or DBP2 protein), peptide, or fusion protein can be immobilized onto a solid phase, reacted with the test compound, and complexes detected by direct or indirect labeling of the test compound. Alternatively, the test, compound can be immobilized, reacted with the nonsense-mediated decay pathway molecule, and the complexes detected. Microtiter plates may be used as the solid phase and the immobilized component anchored by covalent or noncovalent interactions. Non-covalent attachment may be achieved by coating the solid phase with a solution containing the molecule and drying. Alternatively, an antibody, for example, one specific for NMD2 or UPF1, is used to anchor the molecule to the solid surface. Such surfaces may be prepared in advance of use, and stored.

In these screening assays, the non-immobilized component is added to the coated surface containing the immobilized component under conditions sufficient to permit interaction between the two components. The unreacted components are then removed (e.g., by washing) under conditions such that any complexes formed will remain immobilized on the solid phase. The detection of the complexes may be accomplished by a number of methods known to those in the art. For example, the nonimmobilized component of the assay may be prelabeled with a radioactive or enzymatic entity and detected using appropriate means. If the non-immobilized entity was not prelabeled, an indirect method is used. For example, if the non-immobilized entity is an Nmd2p, an antibody against the Nmd2p is used to detect the bound molecule, and a secondary, labeled antibody used to detect the entire complex.

Alternatively, a reaction can be conducted in a liquid phase, the reaction products separated from unreacted components, and complexes detected (e.g., using an immobilized antibody specific for a nonsense-mediated mRNA decay pathway protein).

Cell-based assays can be used to identify compounds that interact with nonsense-mediated mRNA decay pathways proteins. Cell lines that naturally express such proteins or have been genetically engineered to express such proteins (e.g., by transfection or transduction of a UPF1 or NMD2 DNA) can be used. For example, test compounds can be administered to cell cultures and the amount of mRNA derived from a nonsense mutation-containing gene analyzed, e.g., by Northern analysis. An increase in the amount of RNA transcribed from such a gene compared to control cultures that did not contain the test compound indicates that the test compound is an inhibitor of the nonsense-mediated mRNA decay pathway. Similarly, the amount of a polypeptide encoded by a nonsense mutation-containing gene, or the activity of such a polypeptide, can be analyzed in the presence and absence of a test compound. An increase in the amount or activity of the polypeptide indicates that the test compound is an inhibitor of the nonsense-mediated mRNA decay pathway.

An alternative method of identifying small molecules that inhibit nonsense-mediated mRNA decay involves evaluating the effect of test compounds on yeast cells that contain conditional mutations. The conditional mutations permit growth in the presence (or absence) of a specific factor when the nonsense-mediated mRNA decay pathway is not functional. For example, in the absence of functional NMD2, cells harboring leu2 or tyr7 nonsense mutations gain the ability to grow in the absence of leucine or tyrosine, respectively. Therefore, administration of a test compound that effectively inhibits expression o:E the wild-type NMD2 gene in a cell harboring one or more of these mutations, permits the cell to grow under the restrictive condition (e.g., in the absence of leucine or tyrosine, or in the presence of canavanine). In such an experiment, for example, yeast cells that contain leu2-3 or tyr7-1 nonsense mutations are grown in the presence and absence of test compounds. Compounds that promote the growth of cells in the presence of leucine or tyrosine, respectively, are candidate compounds to be used as drugs that inhibit the nonsense-mediated mRNA decay pathway. This type of test can also be performed in yeast cells that lack functional NMD2 and express human NMD2 cDNA, thus restoring the nonsense-mediated mRNA decay pathway in a yeast cell with a human gene product to provide an in vitro model that can be used to identify candidate compounds that may be effective in humans.

Candidate compounds can also be screened using cells containing a nonsense mutation in the CAN1 gene. Canavanine is a growth inhibitor that requires the presence of arginine permease, a protein encoded by the CAN1 gene, to enter cells. Cells harboring the can1-100 nonsense mutation are resistant to 100 μg/ml canavanine if they are wild-type for the nonsense-mediated mRNA decay pathway, but sensitive if they harbor an NMD2 mutation. To screen for candidate compounds that inhibit the nonsense-mediated mRNA decay pathway, yeast cells that have the can1-100 mutation and are wild-type for the nonsense-mediated mRNA decay pathway are incubated in the presence and absence of 100 μg/ml canavanine. If a candidate compound inhibits cell growth in canavanine, the compound is a candidate drug for inhibiting nonsense-mediated mRNA decay.

Candidate inhibitory compounds can be tested in tissue culture cells. For example, nonsense-containing β-globin mRNAs are rapidly degraded in culture cells (Maquat et al., 1981, Cell 27:543–553; Maquat, 1995, RNA 1:453–465). Such rapid decay would be reversed by candidate drugs that are effective at inhibiting the mRNA decay pathway. Culture cells expressing nonsense mutation-containing globin genes are incubated with a candidate compound. Lysates are prepared from treated and untreated cells and Western blotted according to known methods. The blots are probed with antibodies specific for the amino or carboxy terminus of β-globin and the amount of each quantitated. An increase in the amount of carboxy-terminal β-globin in treated compared to untreated cells indicates that the candidate compound is inhibiting nonsense-mediated mRNA decay and is a candidate for a drug to treat disorders associated with nonsense mutations.

Example 13

Assays for Compounds that Interfere with Upf1p/Nmd2p or Upf3p/Nmd2p Interactions Assays for compounds that interfere with the interactions of Nmd2p with its binding partners can be based on both biochemical and genetic approaches. In one biochemical approach, interaction of a Upf1p and an Nmd2p or Upf3p, is monitored using methods described above, or by more automated methods. The latter include the use of devices such as the BIAcore® (Pharmacia Biosensor, Uppsala, Sweden), a surface plasmon resonance dectector that measures the interactions of very small amounts of proteins (Szabo et al., (1995) Curr. Opin. Struct. Biol. 1:699–705). The BIAcore provides rapid (e.g., within seconds) graphical output of data indicating whether two molecules have interacted, and the affinity and kinetics of that interaction. Thus, it provides a suitable method of screening for compounds that interfere with the interaction between the molecules of interest. To assay the ability of a candidate compound to interfere with the interaction between, for example, a Nmd2p and a Upf1p, isolated Nmd2p is covalently attached to the surface of a sensor chip. The chip is coated with carboxymethylated dextran and the protein of interest (e.g., an Nmd2p) is linked to the coating via the protein's primary amine groups using carbodiimide coupling. After washing, the chip is inserted into the sensor, and a solution containing the partner protein (in this case, a Upf1p), is pumped over the surface of the chip. Interaction, as surface plasmon resonance, is detected optically in real time (readouts may be collected at 0.1 second intervals). The kinetic rates of association and, after removing unbound free protein (in this case, Upf1p), dissociation are measured. Compounds that are candidates to interfere with the interaction between Nmd2p and Upf1p are added either with Upf1p (to test for interference with association), or after washing out the Upf1p (to test the ability of the candidate compound to enhance the rate of dissociation between Nmd2p and Upf1p). A comparison between the association and dissociation rates of Nmd2p and Upf1p in the presence and absence of the candidate compound indicates whether the compound affects either rate. Candidate compounds that decrease the rate of association or increase the rate of dissociation are compounds that are to be tested further for their ability to interfere with nonsense-mediated RNA decay. The protocol can also be performed by covalently binding Upf1p to the chip and using Nmd2p as the free partner in the assay. Compounds that interfere with the interaction between Nmd2p and Upf3p can be tested as described for Nmd2p and Upf1p.

A genetic approach using a two-hybrid assay can also be used to screen for compounds that interfere with the interaction between components of the nonsense-mediated mRNA decay pathway. The two-hybrid system is a genetic assay in yeast cells that can detect protein:protein interaction (Fields and Song (1989) Nature 340:245–246; Chien et al., (1991) Proc. Nat. Acad. Sci. USA 88:9578–9582; Fields and Sternglanz, (1994) Trends Genet. 10:286–292). The method is based on the observation that the DNA binding and transcriptional activation functions of the GAL4 protein (Gal4p) can reside on two distinct chimeric polypeptides and still activate transcription from a GAL UAS (upstream activation sequence), provided that the two polypeptides can interact with each other.

To use the two-hybrid assay to screen for candidate compounds that interfere with the interaction betweeen Nmd2p and Upf1p or Upf3p, for example, two plasmids encoding chimeric sequences are constructed. In one plasmid, the nucleic acid sequence containing the entire UPF1 (or UPF3) coding region, or fragments thereof, is fused in-frame to the Gal4p DNA binding domain or the lexa binding domain. The other plasmid contains the NMD2 gene, or fragments thereof, fused to sequences encoding the Gal4p transcriptional activation domain (amino acids 768–881). The nonsense-mediated mRNA decay pathway genes can be from a yeast or another organism. Plasmids encoding both hybrid molecules are cotransformed into a *Saccharomyces cerevisiae* strain that contains an integrated GAL1-lacZ reporter construct and an integrated GAL1-HIS3 reporter construct. The transformed yeast are plated and those colonies expressing detectable β-galactosidase activity (blue colonies on X-gal plates) and HIS3 activity (detected by resistance to 3-aminotriazole [5–80 mM]; 3-AT) are indicative of interaction. The lacZ assay is a quantitative assay for enzymatic activity. The HIS3 assay provides a colony growth assay, e.g., resistance to different concentrations of aminotriazole. Compounds to be tested for their ability to interfere with the interaction between Nmd2p and Upf1p (or Upf3p) are added to yeast containing the two plasmid constructs in either liquid or solid growth media. Interaction between the two proteins of interest is scored by expression of the lacZ gene or the HIS3 gene. In the case of the lacZ gene, compounds that specifically interfere with interaction are those that decrease the β-galactosidase activity (i.e., colonies are white, not blue, thus indicating diminished or eliminated activity). The effect of a compound on the interaction can also be detected via HIS3 activity, e.g., compounds that prevent the transformed yeast cells from growing in the presence of 3-AT are candidate compounds for interfering with the interaction between the two proteins (the product of the HIS3 gene antagonizes the latter drug).

Example 14

Assays for Compounds that Ameliorate the Effects of Nonsense-mediated mRNA Decay in Vivo Compounds identified as above, or other candidate compounds that inhibit mRNA-mediated decay pathway proteins in vitro may be useful for treating disorders caused by nonsense mutations. These compounds can be tested in in vivo assays, for example, in animal models of genetic disorders involving nonsense mutations. One such model uses mice transgenic for and that express human β-globin genes. These mice have been shown to be subject to nonsense-mediated mRNA decay (Lim et al., Mol. Cell. Biol. 12:1149–1161, 1992).

Candidate compounds predicted to inhibit the nonsense-mediated mRNA decay pathway are administered to animals containing nonsense mutations and assayed for inhibition of the nonsense-mediated mRNA decay pathway. Such assays may be indirect or inferential, for example, inhibition would be indicated by improved health or survival of the animal. Assays may also be direct. For example, inhibition would be indicated by a change in the expression of a disease gene (e.g., nonsense codon-containing gene) as measured, e.g., by Northern analysis of tissue removed from an animal treated with a candidate compound. An increase in the amount of disease gene mRNA present in the sample from treated animals compared to untreated control would indicate that the candidate compound is inhibiting the nonsense-mediated mRNA decay pathway. Similarly, the polypeptide encoded by the disease gene can be measured. For example, an increase in the amount of polypeptide indicates that the candidate compound is inhibiting the nonsense-mediated mRNA decay pathway.

Use

The nonsense-mediated mRNA decay pathway can be inhibited by overexpressing the C-terminal truncated form of an Nmd2p in a cell (such as a yeast cell). Other methods for inhibiting the nonsense-mediated mRNA decay pathway include disruption or mutation of an NMD2 gene or NMD2 antisense transcript expression. As a result, a transcript for a heterologous protein which contains at least one stop codon within a transcript-destabilizing 5' portion will be specifically stabilized when expressed in a host cell inhibited in a nonsense-mediated mRNA decay pathway. Such stabilization allows translation of the stabilized transcript in a yeast suppressor mutant to produce a full-length peptide with an amino acid inserted at the position of the nonsense codon. The inserted amino acid is specific to the suppressor mutant host in which the heterologous gene and the Nmd2p C-terminus are expressed. The relevant properties of each of the mutant heterologous proteins are compared to the properties of the wild-type protein, and altered heterologous proteins having desired properties are collected. Such properties may include, but are not limited to, protein receptor binding, antibody binding, enzymatic activity, three dimensional structure, and other biological and physical properties known to those of ordinary skill in the arts of biochemistry and protein chemistry.

The invention is also useful in the production of heterologous protein fragments by inserting into the DNA a stop codon within a transcript-destabilizing 5' portion of the coding sequence at a site at which translation is to stop thereby producing an N-terminal protein fragment. This can be done using site-directed mutagenesis. PCR or oligonucleotides containing the desired sequence are used to alter a specific codon in a gene of interest cloned into an expression plasmid using methods known in the art. Fragments useful in pharmaceutical or other applications can be isolated in large quantities if so desired by techniques well known to those of ordinary skill in the art.

Methods of Treating Disorders Involving Nonsense Mutations

The invention also encompasses the treatment of disorders, especially in mammals, caused by nonsense mutations. A broad range of genetic disorders associated with a nonsense mutation can be treated by the methods described herein. Without limiting the invention by committing to any particular theory, a substantial number of genetic disorders are attributable to the presence of a premature translational termination colon (e.g, nonsense codon) within the coding region of specific genes (e.g., certain cases of β-thalassemia, breast: cancer, polycystic kidney disease I, and Duchenne muscular dystrophy). Table 4 gives examples of specific sites of nonsense mutations associated with cancers such as breast cancer (BRCA1 and BRCA2), colorectal cancer (non-polyposis), retinoblastoma, adrenocortical carcinoma, and Li-Fraumeni syndrome. Table 4 also gives specific examples of nonsense mutations associated with other disorders: Duchenne muscular dystrophy, polycystic kidney disease I, polycystic kidney disease II, Fanconi anemia, haemophilia A, hypercholesterolemia, neurofibromatosis 1, Tay-Sachs disease, glycogen storage disease III, cystic fibrosis, adenomatous polyposis coli, and β-thalassemia. Many other examples of disorders involving nonsense mutations are known including Cowden disease (Liaw et al., (1997) Nat. Genet. 16:64), Maple syrup urine disease (Fishaer et al., (1993) Am. J. Hum. Genet. 52:414), Wilson disease (Thomas et al. (1995) Nature Genet. 9:210), Niemann-Pick disease (Schuchman et al., (1995) Hum. Mut. 6:352), Turcot syndrome (Hamilton et al., (1995) N. Engl. J. Med. 332:839), McArdle disease (Tsujino et al., (1993) N. Engl. J. Mel. 329:241), and ornithine transcarbamylase deficiency (Oppliger et al. (1997) Hum. Mutat. 9:409).

TABLE 4

| Disease | Codon | Nucleotide | Reference |
|---|---|---|---|
| Breast Cancer (BRCA1) | 1 | ATGg-ATT | Couch (1996) Hum. Mut. 8:8 |
| Breast Cancer (BRCA1) | 63 | TTA-TAA | Inoue (1995) Cancer Res. 55:3521 |
| Breast Cancer (BRCA1) | 484 | aGGA-TGA | Couch (1996) Hum. Mut. 8:8 |
| Breast Cancer (BRCA1) | 510 | TCA-TGA | Garvin (1996) J. Med. Genet. 57:1284 |
| Breast Cancer (BRCA1) | 526 | tCAA-TAA | Friedman (1995) Am. J. Hum. Genet. 57:1284 |
| Breast Cancer (BRCA1) | 563 | tCAG-TAG | Shattuck-E (1995) J. Amer. Med. Assoc. 273:535 |
| Breast Cancer (BRCA1) | 639 | TTG-TAG | Gayther (1995) Nature Genet. 11:428 |
| Breast Cancer (BRCA1) | 780 | tCAG-TAG | Hogervorst (1995) Nature Genet. 10:208 |
| Breast Cancer (BRCA1) | 908 | aGAA-TAA | Serova (1996) Am. J. Hum. Genet. 58:42 |
| Breast Cancer (BRCA1) | 1080 | TTG-TAG | Gayther (1995) Nature Genet. 11:428 |
| Breast Cancer (BRCA1) | 1203 | cCGA-TGA | Friedman (1994) Nature Genet. 8:399 |
| Breast Cancer (BRCA1) | 1250 | cGAG-TAG | Castilla (1994) Nature Genet. 8:387 |
| Breast Cancer (BRCA1) | 1281 | tCAG-TAG | Couch (1996) Hum. Mut. 8:8 |
| Breast Cancer (BRCA1) | 1313 | cCAG-TAG | Shattuck-E (1995) J. Amer. Med. Assoc. 273:535 |
| Breast Cancer (BRCA1) | 1323 | aCAA-TAA | Miki (1994) Science 266:66 |
| Breast Cancer (BRCA1) | 1395 | tCAG-TAG | Langston (1996) New Engl. J. Med. 334:137 |
| Breast Cancer (BRCA1) | 1443 | gCGA-TGA | Castilla (1994) Nature Genet. 8:387 |
| Breast Cancer (BRCA1) | 1541 | aGAG-TAG | Shattuck-E (1995) J. Amer. Med. Assoc. 273:535 |
| Breast Cancer (BRCA1) | 1563 | TACc-TAG | Serova (1996) Am. J. Hum. Genet. 58:42 |
| Breast Cancer (BRCA1) | 1725 | aGAA-TAA | Merajver (1995) Nature Genet. 9:439 |
| Breast Cancer (BRCA1) | 1727 | aAAA-TAA | Gayther (1995) Nature Genet. 11:428 |

TABLE 4-continued

| Disease | Codon | Nucleotide | Reference |
|---|---|---|---|
| Breast Cancer (BRCA1) | 1835 | cCGA-TGA | Serova (1996) Am. J. Hum. Genet. 58:42 |
| Breast Cancer (BRCA1) | 1837 | TGG-TAG | Couch (1996) Hum. Mut. 8:8 |
| Breast Cancer (BRCA2) | 194 | TGG-TAG | Couch (1996) Nature Genet. 13:123 |
| Breast Cancer (BRCA2) | 187 | gGAA-TAA | Phelan (1996) Nature Genet. 13:120 |
| Breast Cancer (BRCA2) | 1970 | TCA-TAA | Gayther (1997) Nature Genet. 15:103 |
| Breast Cancer (BRCA2) | 2984 | TCA-TGA | Gayther (1997) Nature Genet. 15:103 |
| Duchenne Muscular Dystrophy | 60 | gCAA-TAA | Roberts (1994) Hum. Mut. 4:1 |
| Duchenne Muscular Dystrophy | 85 | gCAG-TAG | Roberts (1994) Hum. Mut. 4:1 |
| Duchenne Muscular Dystrophy | 105 | tAAA-TAA | Nigro (1994) Hum. Molec. Genet. 3:1907 |
| Duchenne Muscular Dystrophy | 145 | aCGA-TGA | Roberts (1994) Hum. Mut. 4:1 |
| Duchenne Muscular Dystrophy | 242 | aCAA-TAA | Nigro (1992) Hum. Molec. Genet. 1:517 |
| Duchenne Muscular Dystrophy | 250 | gGAA-TAA | Roberts (1994) Hum. Mut. 4:1 |
| Duchenne Muscular Dystrophy | 354 | TGG-TAG | Nigro (1994) Molec. Genet. 3:1907 |
| Duchenne Muscular Dystrophy | 480 | tGGA-TGA | Roberts (1994) Hum. Mut. 4:1 |
| Duchenne Muscular Dystrophy | 491 | aCAA-TAA | Kneppers (1995) Hum. Mut. 5:235 |
| Duchenne Muscular Dystrophy | 497 | tCAA-TAA | Roberts (1994) Hum. Mut. 4:1 |
| Duchenne Muscular Dystrophy | 522 | tGGA-TGA | Prior (1994) Am. J. Med. Genet. 50:68 |
| Duchenne Muscular Dystrophy | 622 | TCA-TGA | Nigro (1994) Hum. Molec. Genet. 3:1173 |
| Duchenne Muscular Dystrophy | 651 | TGG-TAG | Roberts (1994) Hum. Mut. 4:1 |
| Duchenne Muscular Dystrophy | 673 | tCAG-TAG | Barbieri (1995) Hum. Genet. 96:343 |
| Duchenne Muscular Dystrophy | 768 | gCGA-TGA | Prior (1993) Hum. Molec. Genet. 2:311 |
| Duchenne Muscular Dystrophy | 770 | aAAA-TAA | Roberts (1994) Hum. Mut. 4:1 |
| Duchenne Muscular Dystrophy | 772 | tGAG-TAG | Prior (1993) Hum. Molec. Genet. 2:311 |
| Duchenne Muscular Dystrophy | 825 | TGGc-TGA | Prior (1995) Am. J. Hum. Genet. 57:22 |
| Duchenne Muscular Dystrophy | 838 | tCAG-TAG | Prior (1995) Am. J. Hum. Genet. 57:22 |
| Duchenne Muscular Dystrophy | 931 | aGAG-TAG | Roberts (1992) Proc. Natl. Acad. Sci. USA 89:2331 |
| Duchenne Muscular Dystrophy | 993 | aCAA-TAA | Roberts (1994) Hum. Mut. 4:1 |
| Duchenne Muscular Dystrophy | 1041 | tCAA-TAA | Roberts (1994) Hum. Mut. 4:1 |
| Duchenne Muscular Dystrophy | 1063 | TGG-TAG | Roberts (1994) Hum. Mut. 4:1 |
| Duchenne Muscular Dystrophy | 1087 | gCAG-TAG | Nigro (1994) Hum. Molec. Genet. 3:1907 |
| Duchenne Muscular Dystrophy | 1102 | tCAG-TAG | Barbieri (1996) Eur. J. Hum. Genet. 4:183 |
| Duchenne Muscular Dystrophy | 1157 | gGAG-TAG | Bulman (1991) Genomics 10:457 |
| Duchenne Muscular Dystrophy | 1405 | tCAA-TAA | Roberts (1994) Hum. Mut. 4:1 |
| Duchenne Muscular Dystrophy | 1459 | tCGA-TGA | Prior (1995) Am. J. |

TABLE 4-continued

| Disease | Codon | Nucleotide | Reference |
|---|---|---|---|
| Dystrophy | | | Hum. Genet. 57:22 |
| Duchenne Muscular Dystrophy | 1472 | aCAA-TAA | Roberts (1994) Hum. Mut. 4:1 |
| Duchenne Muscular Dystrophy | 1642 | TTG-TAG | Prior (1995) Am. J. Hum. Genet. 57:22 |
| Duchenne Muscular Dystrophy | 1851 | aCAG-TAG | Roberts (1992) Proc. Natl. Acad. Sci. USA 89:2331 |
| Duchenne Muscular Dystrophy | 1967 | tCGA-TGA | Saad (1993) Hum. Mut. 2:314 |
| Duchenne Muscular Dystrophy | 2098 | gCGA-TGA | Roberts (1994) Hum. Mut. 4:1 |
| Duchenne Muscular Dystrophy | 2125 | aCAG-TAG | Roberts (1994) Hum. Mut. 4:1 |
| Duchenne Muscular Dystrophy | 2182 | aCAG-TAG | Prior (1993) Hum. Mut. 2:192 |
| Duchenne Muscular Dystrophy | 2264 | cCAG-TAG | Roberts (1994) Hum. Mut. 4:1 |
| Duchenne Muscular Dystrophy | 2319 | tCAA-TAA | Roberts (1994) Hum. Mut. 4:1 |
| Duchenne Muscular Dystrophy | 2757 | tGAA-TAA | Prior (1995) Am. J. Hum. Genet. 57:22 |
| Duchenne Muscular Dystrophy | 2815 | gCAG-TAG | Prior (1995) Am. J. Hum. Genet. 57:22 |
| Duchenne Muscular Dystrophy | 2905 | aCGA-TGA | Prior (1995) Am. J. Hum. Genet. 57:22 |
| Duchenne Muscular Dystrophy | 2972 | cCAA-TAA | Tuffery (1996) Eur. J. Hum. Genet. 4:143 |
| Duchenne Muscular Dystrophy | 2982 | tCGA-TGA | Roberts (1992) Proc. Natl. Acad. Sci. USA 89:2331 |
| Duchenne Muscular Dystrophy | 3024 | TGGa-TGA | Prior (1995) Am. J. Hum. Genet. 57:22 |
| Duchenne Muscular Dystrophy | 3066 | TCG-TAG | Roberts (1994) Hum. Mut. 4:1 |
| Duchenne Muscular Dystrophy | 3370 | tCGA-TGA | Roberts (1992) Proc. Natl. Aaad. Sci. USA 89:2331 |
| Duchenne Muscular Dystrophy | 3381 | tCGA-TGA | Lenk (1993) Hum. Molec. Genet. 2:1877 |
| Duchenne Muscular Dystrophy | 3391 | cCGA-TGA | Barbieri (1996) Eur. J. Hum. Genet. 4:183 |
| Duchenne Muscular Dystrophy | 3493 | cCAG-TAG | Barbieri (1996) Eur. J. Hum. Genet. 4:183 |
| Duchenne Muscular Dystrophy | 3635 | tCAA-TAA | Prior (1995) Am. J. Hum. Genet. 57:22 |
| Polyaystia Kidney Disease I | 3818 | TACg-TAA | Peral (1996) Hum. Molea. Genet. 5:539 |
| Polycystic Kidney Disease I | 3837 | gCAG-TAG | Peral (1996) Am. J. Hum. Genet. 58:86 |
| Polycystic Kidney Disease I | 4020 | CCGA-TGA | Rossetti (1996) AM. J. Med. Genet. 65:155 |
| Polycystic Kidney Disease I | 4041 | cCAG-TAG | Turco (1995) Hum. Molec. Genet. 4:1331 |
| Polycystic Kidney Disease I | 4086 | TGTq-TGA | Neophytou (1996) Hum. Genet. 98:437 |
| Polycystic Kidney Disease I | 4227 | cCGA-TGA | Peral (1996) Am. J. Hum. Genet. 58:86 |
| β-Thalassaemia | 16 | TGG-TAG | Kazazian (1984) EMBO J. 3:593 |
| β-Thalassaemia | 16 | TGGg-TGA | Aelehla (1990) Hum. Genet. 84:195 |
| β-Thalassaemia | 18 | cAAG-TAG | Chang (1979) Proc. Natl. Acad. Sci. USA 76:2886 |
| β-Thalassaemia | 23 | tGAA-TAG | Ghanem (1992) Hum. Mut. 1:229 |
| β-Thalassaemia | 27 | tGAG-TAG | Baysal (1995) Hemoglobin 19:213 |
| β-Thalassaemia | 36 | TACc-TAA | Thein (1990) Am. J. Hum. Genet. 47:369 |
| β-Thalassaemia | 38 | TGG-TAG | Xu (1995) Brit. J. Haematol. 90:960 |
| β-Thalassaemia | 38 | TGGa-TGA | Boehm (1986) Blood 67:1185 |
| β-Thalassaemia | 40 | cCAG-TAG | Thecartin (1981) J. Clin. Invest. 68:1012 |
| β-Thalassaemia | 44 | tGAG-TAG | Atweh (1988) J. Clin. Invest. 82:557 |
| β-Thalassaemia | 62 | gAAG-TAG | Gonzales-R (1988) Blood 72:1007 |
| β-Thalassaemia | 91 | tGAG-TAG | Fucharoen (1990) Brit. J. Haematol. 74:101 |
| β-Thalassaemia | 113 | TGTg-TGA | Divoky (1993) Brit. J. Haematol. 83:523 |
| β-Thalassaemia | 122 | aGAA-TAA | Kazazian (1986) Am. J. Hum. Genet. 38:860 |
| β-Thalassaemia | 128 | gCAG-TAG | Hall (1991) Brit. J. Haematol. 79:342 |
| Adenomatous polyposis coli | 157 | Trp-Term | Olschwang (1993) Am. J. Hum. Genet. 52:273 |
| Adenomatous polyposis coli | 805 | tCGA-TGA | Doobie (1996) J. Med. Genet. 33:274 |
| Adenomatous polyposis coli | 1567 | TCA-TGA | Miyoshi (1992) Proc. Natl. Acad. Sci. USA 89:4452 |
| Li-Fraumeni syndrome | 213 | tCGA-TGA | Frebourg (1995) Am J. Hum. Genet. 56:608 |
| Li-Fraumeni syndrome | 306 | gCGA-TGA | Cornelis (1997) Hum. Mutat. 9:157 |
| Coloreatal cancer, non-polyposis | 233 | tCAG-TAG | Verlander (1994) Am. J. Hum. Genet. 54:595 |
| Coloreatal cancer, non-polyposis | 62 | CCAA-TAA | Tannergard (1995) Cancer. Res. 55:6092 |
| Coloreatal cancer, non-polyposis | 252 | TCA-TAA | Papadopoul (1994) Science 263:1625 |
| Coloreatal cancer, non-polyposis | 714 | TGG-TAG | Hutter (1996) J. Med. Genet. 33:636 |
| Coloreatal cancer, non-polyposis | 252 | gCAG-TAG | Liu (1995) Nat. Med. 1:348 |
| Coloreatal cancer, non-polyposis | 458 | TTA-TGA | Liu (1995) Cancer Res. 54:4590 |
| Coloreatal cancer, non-polyposis | 811 | TTA-TGA | Miyaki (1995) J. Mol. Med. 73:515 |
| Fanconi anemia | 13 | tCAG-TAG | Verlander (1994) Am. J. Hum. Genet. 54:595 |
| Fanconi anemia | 185 | aCGA-TGA | Gibson (1993) Hum. Mol. Genet. 2:797 |
| Fanconi anemia | 547 | cCGA-TGA | Marer-Orl. (1993) Lancet 342:686 |
| Retinoblastoma | 99 | TGG-TAG | Blanquet (1995) Hum. Mol. Genet. 4:383 |
| Retinoblastoma | 467 | aCGA-TGA | Blanquet (1995) Hum. Mol. Genet. 4:383 |
| Retinoblastoma | 467 | aCGA-TGA | Blanquet (1995) Hum. Mol. Genet. 4:383 |
| Cystic Fibrosis | 4 | TCG-TAG | Glavac (1993) Hum. Mol. Genet. 2:315 |
| Cystic Fibrosis | 553 | aCGA-TGA | Cutting (1990) Nature 346:366 |
| Cystic Fibrosis | 1371 | tGAA-TAA | Cutting (1992) Am. |

TABLE 4-continued

| Disease | Codon | Nucleotide | Reference |
|---|---|---|---|
| | | | J. Hum. Genet. 50:1185 |
| Glycogen storage disease III | 6 | aCAG-TAG | Shen (1996) J. Clin. Invest. 98:352 |
| Glycogen storage disease III | 680 | TGG-TAG | Shen (1996) J. Clin. Invest. 98:352 |
| Glycogen storage disease III | 1228 | tCGA-TGA | Shen (1996) J. Clin. Invest. 98:352 |
| Polycystic kidney disease 2 | 380 | TGG-TAG | Mochizuki (1996) Science 272:1339 |
| Polycystic kidney disease 2 | 405 | aCAA-TAA | Mochizuki (1996) Sdience 272:1339 |
| Polycystic kidney disease 2 | 742 | tCGA-TGA | Mochizuki (1996) Science 272:1339 |
| Tay-Sachs disease | 26 | TGGc-TGA | Triggs-Rai (1991) Am. J. Hum. Genet. 49:1041 |
| Tay-Sachs disease | 180 | TACc-TAG | Drucker (1992) Am. J. Hum. Genet. 51:371 |
| Tay-Sachs disease | 393 | gCGA-TGA | Akli (1.991) Genomics 11:124 |
| Neurofibromatosis 1 | 239 | aCAG-TAG | Horn (1996). Electrophoresis 17:1559 |
| Neurofibromatosis 1 | 1362 | tCGA-TGA | Upadhyaya (1997) Hum. Genet. 99:88 |
| Neurofibromatosis 1 | 2518 | tGGA-TGA | Heim (1995) Hum. Mol. Genet. 99:674 |
| Hypercholesterol-emia | 10 | cGAG-TAG | Cenarro (1996) Clin. Genet. 49:180 |
| Hypercholesterol-emia | 210 | TGCg-TGA | Gudnason (1993) Arterscl. Thromb. 13:56 |
| Hypercholesterol-emia | 660 | TGCc-TGA | Lehrmann (1987) J. Biol. Chem. 262:401 |
| Haemophilia A | −5 | gCGA-TGA | Pattinson (1990) Blood 76:2242 |
| Haemophilia A | 636 | TACt-TAG | Becker (1996) Am. J. Hum. Genet. 58:657 |
| Haemophilia A | 2270 | tCAG-TAG | Becker (1996) Am. J. Hum. Genet. 58:657 |

As described herein, nonsense codons not only interrupt translation, but also promote enhanced decay of transcripts from genes containing nonsense mutations. Based on the yeast paradigm in which inhibition of the nonsense-mediated mRNA decay pathway permits "read-through" and thus increased expression of genes containing nonsense mutations, inhibitors of this pathway, identified as described above are useful for treating disorders involving nonsense mutations Therapy is designed to reduce the level of endogenous nonsense-medidated mRNA decay pathway gene expression (e.g., expression of an NMD2, UPF1, UPF3, or homologs thereof) using, e.g., antisense or ribozyme approaches to inhibit or prevent translation of a nonsense-mediated mRNA decay pathway mRNA transcript; triple helix approaches to inhibit transcription of the gene; or targeted homologous recombination to inactivate or "knock out" a gene or its endogenous promoter. The antisense, ribozyme, or DNA constructs described herein can be administered directly to the site containing the target cells; e.g., heart, skeletal muscle, thymus, spleen, and small intestine.

Effective Dose

Toxicity and therapeutic efficacy of the polypeptides of the invention and the compounds that modulate their expression or activity can be determined by standard pharmaceutical procedures, using either cells in culture or experimental animals to determine the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Polypeptides or other compounds that exhibit large therapeutic indices are preferred. While compounds that exhibit toxic side effects may be used, care should be taken to design a delivery system that targets such compounds to the site of affected tissue to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (that is, the concentration of the test compound which achieves a half-maximal inhibition of symptoms) as determined in cell culture. Such information can be used to more accurately determine useful doses in humans. Levels in plasma can be measured, for example, by high performance liquid chromatography. Dosages are from about 0.1 to 500 mg per day.

Formulations and Use

Pharmaceutical compositions for use in accordance with the present invention can be formulated in a conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (for example, pregelatinised maize starch, polyvinylpyrrolidone or hydroxypropyl methylcellulose); fillers (for example, lactose, microcrystalline cellulose or calcium hydrogen phosphate); lubricants (for example, magnesium stearate, talc or silica); disintegrants (for example, potato starch or sodium starch glycolate); or wetting agents (for example, sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example, sorbitol syrup, cellulose derivatives or hydrogenated edible fats); emulsifying agents (for example, lecithin or acacia); non-aqueous vehicles (for example, almond oil, oily esters, ethyl alcohol or fractionated vegetable oils); and preservatives (for example, methyl or propyl-p-hydroxybenzoates or sorbic acid). The preparations may also contain buffer salts, flavoring, coloring and sweetening agents as appropriate. Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebulizer, with the use of a suitable propellant, for example, dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, for example, gelatin for use in an inhaler or insufflator may be formulated containing a powder mix of the compound and a suitable powder base such as lactose or starch.

The compounds may be formulated for parenteral administration by injection, for example, by bolus injection or continuous infusion. Formulations for injection may be presented in unit dosage form, for example, in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, for example, sterile pyrogen-free water, before use.

The compounds may also be formulated in rectal compositions such as suppositories or retention enemas, for example, containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

The therapeutic compositions of the invention can also contain a carrier or excipient, many of which are known to skilled artisans. Excipients which can be used include buffers (for example, citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. The nucleic acids, polypeptides, antibodies, or modulatory compounds of the invention can be administered by any standard route of administration. For example, administration can be parenteral, intravenous, subcutaneous, intramuscular, intracranial, intraorbital, opthalmic, intraventricular, intracapsular, intraspinal, intracisternal, intraperitoneal, transmucosal, or oral. The modulatory compound can be formulated in various ways, according to the corresponding route of administration. For example, liquid solutions can be made for ingestion or injection; gels or powders can be made for ingestion, inhalation, or topical application. Methods for making such formulations are well known and can be found in, for example, "Remington's Pharmaceutical Sciences." It is expected that the preferred route of administration will be intravenous.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of determining whether a candidate compound modulates the nonsense-mediated mRNA decay pathway, the method comprising
   a. obtaining a cell containing a nonsense mutation-containing gene and a gene that lacks a nonsense mutation,
   b. incubating the cell with the candidate compound under conditions and for a time sufficient for the cell to express nonsense-mediated mRNA decay pathway genes if the candidate compound is not present,
   c. measuring expression of the genes, or the activities of proteins expressed by the genes, in the presence and in the absence of the candidate compound, and
   d. comparing alterations in the level of expression or activity, wherein a difference in the expression or activity of a protein expressed by the nonsense mutation-containing gene compared to the difference in expression or activity of a protein expressed by the gene that lacks a nonsense mutation indicates that the compound modulates the activity of the nonsense-mediated mRNA decay pathway.

2. The method of claim 1, wherein the cell is a yeast cell containing a nonsense suppressor gene and a gene containing a nonsense mutation such that the ability of the cell to grow in a selective medium depends on the functionality of the nonsense-mediated decay pathway.

3. The method of claim 1, wherein the gene containing a nonsense mutation is selected from the group consisting of tyr7, leu2, and CAN1.

4. The method of claim 1, wherein the compound modulates a nonsense-mediated decay pathway gene selected from the group consisting of NMD2 and a homolog of NMD2.

5. The method of claim 1, wherein the compound modulates a nonsense-mediated decay pathway gene selected from the group consisting of UPF1 and a homolog of UPF1.

6. The method of claim 1, wherein the compound modulates a nonsense-mediated decay pathway gene selected from the group consisting of RENT1 and HUPF1.

7. The method of claim 1, wherein the compound modulates a nonsense-mediated decay pathway gene selected from the group consisting of UPF3 and a homolog of UPF1.

8. The method of claim 1, wherein the cell containing a nonsense mutation is from a mammal.

9. The method of claim 1, wherein the cell containing a nonsense mutation is from a human.

10. The method of claim 1, wherein the candidate compound is a small molecule.

11. The method of claim 1, wherein the candidate compound is a nucleic acid.

12. The method of claim 1, wherein the expression or activity of the protein expressed by the nonsense mutation-containing gene is increased relative to the expression or activity of the protein expressed by the gene that does not contain a nonsense mutation.

13. The method of claim 1, wherein the cell is a yeast cell comprising a nonsense suppressor gene and a nonessential gene containing a nonsense mutation such that the ability of the cell to grow in a selective medium depends on the functionality of the nonsense-mediated decay pathway.

14. A method of determining whether a candidate compound modulates the nonsense-mediated mRNA decay pathway, the method comprising a. obtaining a cell containing a nonsense mutation-containing gene and a cell containing a gene that lacks a nonsense mutation, b. incubating the cells with the candidate compound under conditions and for a time sufficient for the cells to express nonsense-mediated mRNA decay pathway genes if the candidate compound is not present, c. measuring expression of the genes, or the activities of proteins expressed by the genes, in the presence and in the absence of the candidate compound, and d. comparing alterations in the level of expression or activity, wherein a difference in the expression or activity of a protein expressed by the nonsense mutation-containing gene compared to the difference in expression or activity of a protein expressed by the gene that does not contain a nonsense mutation indicates that the compound modulates the activity of the nonsense-mediated mRNA decay pathway.

* * * * *

UNITED STATES PATENT AND TRADEMARK OFFICE
CERTIFICATE OF CORRECTION

PATENT NO. : 6,071,700
DATED : June 6, 2000
INVENTOR(S) : Feng He and Allan S. Jacobson It is certified that error appears in the above-identified patent and that said Letters Patent is hereby corrected as shown below:

Column 86,
Line 43, replace "UPF1" with -- UPF3 --.

Signed and Sealed this

Twenty-fourth Day of September, 2002

Attest:

JAMES E. ROGAN
Attesting Officer    Director of the United States Patent and Trademark Office